United States Patent
Bezencon et al.

(10) Patent No.: US 10,246,426 B2
(45) Date of Patent: Apr. 2, 2019

(54) TRIAZOLE COMPOUNDS AS T-TYPE CALCIUM CHANNEL BLOCKERS

(71) Applicant: IDORSIA PHARMACEUTICALS LTD, Allschwil (CH)

(72) Inventors: Olivier Bezencon, Allschwil (CH); John Gatfield, Allschwil (CH); Bibia Heidmann, Allschwil (CH); Romain Siegrist, Allschwil (CH); Simon Stamm, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 24 days.

(21) Appl. No.: 15/510,980

(22) PCT Filed: Sep. 14, 2015

(86) PCT No.: PCT/EP2015/070934
§ 371 (c)(1),
(2) Date: Mar. 13, 2017

(87) PCT Pub. No.: WO2016/041892
PCT Pub. Date: Mar. 24, 2016

(65) Prior Publication Data
US 2018/0230109 A1    Aug. 16, 2018

(30) Foreign Application Priority Data
Sep. 15, 2014  (WO) ................. PCT/EP2014/069592

(51) Int. Cl.
| | | |
|---|---|---|
| *C07D 249/04* | (2006.01) | |
| *C07D 403/12* | (2006.01) | |
| *C07D 401/12* | (2006.01) | |
| *C07D 405/12* | (2006.01) | |
| *C07D 401/10* | (2006.01) | |
| *C07D 401/14* | (2006.01) | |
| *C07D 403/06* | (2006.01) | |
| *C07D 403/10* | (2006.01) | |
| *C07D 405/06* | (2006.01) | |
| *C07D 471/04* | (2006.01) | |

(52) U.S. Cl.
CPC ......... *C07D 249/04* (2013.01); *C07D 401/10* (2013.01); *C07D 401/12* (2013.01); *C07D 401/14* (2013.01); *C07D 403/06* (2013.01); *C07D 403/10* (2013.01); *C07D 403/12* (2013.01); *C07D 405/06* (2013.01); *C07D 405/12* (2013.01); *C07D 471/04* (2013.01)

(58) Field of Classification Search
None
See application file for complete search history.

(56) References Cited

U.S. PATENT DOCUMENTS

| | | |
|---|---|---|
| 2008/0146625 A1 | 6/2008 | Berthel et al. |
| 2010/0310493 A1 | 12/2010 | Bhuniya et al. |
| 2012/0289698 A1 | 11/2012 | Ashcraft et al. |
| 2015/0329533 A1 | 11/2015 | Nam et al. |
| 2016/0106102 A1 | 4/2016 | Kuebbeler et al. |

FOREIGN PATENT DOCUMENTS

| | | |
|---|---|---|
| EP | 2 402 327 | 1/2012 |
| EP | 2 530 078 | 12/2012 |
| WO | WO 1996/000218 | 1/1996 |
| WO | WO 1998/028269 | 7/1998 |
| WO | WO 2002/000651 | 1/2002 |
| WO | WO 2002/053101 | 7/2002 |
| WO | WO 2002/053160 | 7/2002 |
| WO | WO 2003/037274 | 5/2003 |
| WO | WO 2003/051315 | 6/2003 |
| WO | WO 2003/051833 | 6/2003 |
| WO | WO 2003/101423 | 12/2003 |
| WO | WO 2004/089303 | 10/2004 |
| WO | WO 2004/089306 | 10/2004 |

(Continued)

OTHER PUBLICATIONS

Anderson et al., "Thalamic $Ca_v3.1$ T-type $C^{a2}$ channel plays a crucial role in stabilizing sleep", PNAS, vol. 102(5), p. 1743-1748, (2005).
Becker et al.,"Transcriptional Upregulation of $Ca_v3.2$ Mediates Epileptogenesis in the Pilocarpine Model of Epilepsy", J. Neurosci., vol. 28(49), p. 13341-13353, (2008).
Berg et al., "Revised terminology and concepts for organization of seizures and epilepsies: Report of the ILAE Commission on Classification and Terminology", Epilepsia, vol. 51(4), p. 676-685, (2010).
Bhave et al., "Posttranslational Mechanisms of Peripheral Sensitization", J. Neurobiol., vol. 61, p. 88-106, (2004).
Bourinet et al., "Silencing of the $Ca_v3.2$ T-type calcium channel gene in sensory neurons demonstrates its major role in nociception", The Embo Journal, vol. 24(2), p. 315-324, (2005).

(Continued)

*Primary Examiner* — Samantha L Shterengarts
(74) *Attorney, Agent, or Firm* — Hoxie & Associates LLC

(57) ABSTRACT

The invention relates to compounds of formula (I)

Formula (I)

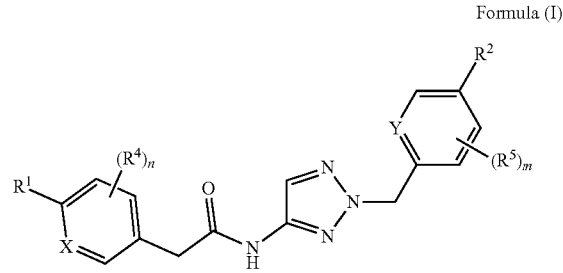

wherein
X, Y, $R^1$, $R^2$, $(R^4)_n$, and $(R^5)_m$ are as defined in the description, and to pharmaceutically acceptable salts of such compounds. These compounds are useful as calcium T-channel blockers.

13 Claims, No Drawings

(56) References Cited

FOREIGN PATENT DOCUMENTS

| WO | WO 2004/099154 | 11/2004 |
|---|---|---|
| WO | WO 2005/056532 | 6/2005 |
| WO | WO 2006/114274 | 11/2006 |
| WO | WO 2006/114313 | 11/2006 |
| WO | WO 2007/073497 | 6/2007 |
| WO | WO 2007/120729 | 10/2007 |
| WO | WO 2008/012227 | 1/2008 |
| WO | WO 2008/085888 | 7/2008 |
| WO | WO 2008/156726 | 12/2008 |
| WO | WO 2009/054982 | 4/2009 |
| WO | WO 2009/054983 | 4/2009 |
| WO | WO 2009/054984 | 4/2009 |
| WO | WO 2009/121623 | 10/2009 |
| WO | WO 2010/073011 | 7/2010 |
| WO | WO 2010/075376 | 7/2010 |
| WO | WO 2010/122088 | 10/2010 |
| WO | WO 2011/022315 | 2/2011 |
| WO | WO 2011/053542 | 5/2011 |
| WO | WO 2011/084402 | 7/2011 |
| WO | WO 2012/077932 | 6/2012 |
| WO | WO 2013/134142 | 9/2013 |
| WO | WO 2014/187928 | 11/2014 |
| WO | WO 2015/186056 | 12/2015 |
| WO | WO 2016/123533 | 8/2016 |

OTHER PUBLICATIONS

Broicher et al., "Correlation of T-Channel Coding Gene Expression, I $_T$, and the Low Threshold Ca$^{2+}$ Spike in the Thalamus of a Rat Model of Absence Epilepsy", Molecular and Cellular Neuroscience, vol. 39(3), p. 1-66, (2008).
Cavelier et al., "Participation of low-threshold Ca$^{2+}$ spike in the Pukinje cells complex spike", Neuroreport, vol. 19(3), p. 299-303, (2008).
Cheong et al., "T-type Ca$^{2+}$ channels in absence epilepsy", Eur. J. Physiol., vol. 466(4), p. 719-734, (2014).
Coderre et al., "Contribution of central neuroplasticity to pathological review of clinical and experimental evidence", Pain, vol. 52, p. 259-285, (1993).
Destexhe et al., "A Model of Spindle Rhythmicity in the Isolated Thalamic Reticular Nucleus", Journal of Neurophysiology, vol. 72(2), p. 803-818, (1994).
Flatters et al., "T-type calcium channels: a potential target for the treatment of chronic pain", Drugs of the Future, vol. 30(6), p. 573-580, (2005).
Giordanetto et al., "T-type calcium channels inhibitors: a patent review", Expert Opin. Ther. Patents, vol. 21(1), p. 85-101, (2011).
Graef et al., "An Acquired Channelopathy Involving Thalamic T-Type Ca$^{2+}$ Channels after Status Epilepticus", J. Neurosci., vol. 29(14), p. 4430-4441, (2009).
Greene et al., "Protective Groups in Organic Synthesis", P.G.M. Wuts, Wiley-Interscience, (1999).
Gutnick et al., "Low threshold calcium spikes, intrinsic neuronal oscillation and rhythm generation in the CNS", J. Neurosci., Methods, vol. 28, p. 93-99, (1989).
Hall et al., "Non-acidic pyrazole EP$_1$ receptor antagonists with in vivo analgesic efficacy", Bioorg. Med. Chem. Lett., vol. 18, p. 3392-3399, (2008).
Hall et al., "Voltage-dependent calcium currents are enhanced in dorsal root ganglion neurones from the Bio Bred/Worchester diabetic rat", J. Physiol., vol. 486(2), p. 313-322, (1995).
Heron et al., "Extended Spectrum of Idiopathic Generalized Epilepsies Associated with CACNA1H Functional Variants", Ann Neurol., vol. 62(6), p. 560-568, (2007).
Huguenard et al., "Intrathalamic Rhythmicity Studied in vitro: Nominal T-Current Modulation Causes Robust Antioscillatory Effects", The Journal of Neuroscience, vol. 14(9), p. 5485-5502, (1994).
Iftinca et al., "Neuronal T-type calcium channels: What's new?", Journal of Medicine and Life, vol. 4(2), p. 126-138, (2011).

Iftinca et al., "Regulation of neuronal T-type calcium channels", Trends Pharmacol. Sci., vol. 30(1), p. 32-40, (2009).
International Search Report of International Application No. PCT/EP2015/070934 dated Oct. 23, 2015, 3 pages.
Jagodic et al., Cell-Specific Alterations of T-Type Calcium Current in Painful Diabetic Neuropathy Enhance Excitability of Sensory Neurons, The Journal of Neuroscience, vol. 27(12), p. 3305-3316, (2007).
Jagodic et al., "Upregulation of the T-Type Calcium Current in Small Rat Sensory Neurons After Chronic Constrictive Injury of the Sciatic Nerve", J. Neurophysiol., vol. 99, p. 3151-3156, (2008).
Jeanmonod et al., "Low-threshold calcium spike bursts in the human thalamus Common physiopathology for sensory, motor and limbic positive symptoms", Brain, vol. 119, p. 363-375, (1996).
Jevtovic-Todorovic et al., "The role of peripheral T-type calcium channels in pain transmission", Cell Calcium, vol. 40, p. 197-203, (2006).
Khosravani et al., "Voltage-Gated Calcium Channels and Idiopathic Generalized Epilepsies", Physiol. Rev., vol. 86(3), p. 941-966, (2006).
Kim et al., "Lack of the Burst Firing of Thalamocortical Relay Neurons and Resistance to Absence Seizures in Mice Lacking $\alpha_{1G}$ T-Type Ca$^{2+}$ Channels", Neuron, vol. 31(1), p. 35-45, (2001).
Lambert et al., "The many faces of T-type calcium channels", Eur J Physiol, vol. 466(3), p. 415-423, (2014).
Latham et al., "Selective T-Type Calcium Channel Blockade Alleviates Hyperalgesia in ob/ob Mice Diabetes", vol. 58, p. 2656-2665, (2009).
Lee et al., "Lack of delta waves and sleep disturbances during non-rapid eye movement sleep in mice lacking a1$_G$-subunit of T-type calcium channels", PNAS, vol. 101(52), p. 18195-18199, (2004).
Llinas et al., "Oscillatory properties of guinea-pig inferior olivary neurones and their pharmacological modulation: an in vitro study", J. Physiol., vol. 376, p. 163-182, (1986).
Lory et al., "Calcium channelopathies in inherited neurological disorders: Relevance to drug screening for acquired channel disorders", IDrugs, vol. 13(7), p. 467-471, (2010).
McGivern et al., "Targeting N-type and T-type calcium channels for the treatment of pain", Drug Discovery Today, vol. 11(5-6), p. 245-53, (2006).
Messinger et al., "In vivo silencing of the Ca$_v$3.2 T-type calcium channels in sensory neurons alleviates hyperalgesia in rats with streptozocin-induced diabetic neuropathy", Pain, vol. 145, p. 1-12, (2009).
Miwa et al., "T-Type Calcium Channel as a New Therapeutic Target for Tremor", Cerebellum, vol. 10, p. 563-569, (2011).
Nelson et al., "The Role of T-Type Calcium Channels in Epilepsy and Pain", Curr. Pharm. Des., vol. 12, p. 2189-2197, (2006).
Park et al., "Supporting Information", PNAS, vol. 107, p. 1-6, (2010).
Powell et al., "ACa$_v$3.2 T-Type Calcium Channel Point Mutation Has Splice-Variant-Specific Effects on Function and Segregates with Seizure Expression in a Polygenic Rat Model of Absence Epilepsy", The Journal of Neuroscience, vol. 29(2), p. 371-380, (2009).
Reger et al., "Pyridyl amides as potent inhibitors of T-type calcium channels", Bioorganic & Medicinal Chemistry Letters, vol. 21, p. 1692-1696, (2011).
Remington, The Science and Practice of Pharmacy, 21st Edition (2005), Part 5, "Pharmaceutical Manufacturing" [published by Lippincott Williams & Wilkins].
Song et al., "Role of the a1G T-Type Calcium Channel in Spontaneous Absence Seizures in Mutant Mice", Neurobiology of Disease, vol. 24(22), p. 5249-5257, (2004).
Stahl et al., "Handbook of Pharmaceutical Salts. Properties, Selection and Use", IUPAC, (2008).
Steriade et al., "Sleep, epilepsy and thalamic reticular inhibitory neurons", Trends in Neuroscience, vol. 28(6), p. 317-324, (2005).
Su et al., "Upregulation of a T-Type Ca$^{2+}$ Channel Causes a Long-Lasting Modification of Neuronal Firing Mode after Status Epilepticus", J. Neurosci., vol. 22(9), p. 3645-3655, (2002).

(56) References Cited

OTHER PUBLICATIONS

Talley et al., "Differential Distribution of Three Members of a Gene Family Encoding Low Voltage-Activated (T-Type) Calcium Channels", J. Neurosci., vol. 19(6), p. 1895-1911, (1999).

Talley et al., "Low-voltage-activated calcium channel subunit expression in a genetic model of absence epilepsy in the rat", Molecular Brain Research, vol. 75, p. 159-165, (2000).

Todorovic et al., "Regulation of T-Type Calcium Channels in the Peripheral Pain Pathway", Channels, vol. 1(4), p. 238-245, (2007).

Todorovic et al., "T-type voltage-gated calcium channels as targets for the development of novel pain therapies", Br. J. Pharmacol., vol. 163, p. 484-495, (2011).

Tsakiridou et al., "Selective Increase in T-Type Calcium Conductance of Reticular Thalamic Neurons in a Rat Model of Absence Epilepsy", The Journal of Neuroscience, vol. 15(4), p. 3110-3117, (1995).

Uslaner et al., "T-Type Calcium Channel Antagonism Decreases Motivation for Nicotine and Blocks Nicotine- and Cue-Induced Reinstatement for a Response Previously Reinforced with Nicotine", Biological Psychiatry, vol. 68(8), p. 712-718, (2010).

Wang et al., "General Solution to the Synthesis of N-2-Substituted 1,2,3-Triazoles", Organic Letters, vol. 12(20), p. 4632-4635, (2010).

Wen et al., "Intrathecal administration of Cav3.2 and Cav3.3 antisense oligonucleotide reverses tactile allodynia and thermal hyperalgesia in rats following chronic compression of dorsal root of ganglion", Acta. Pharmacol. Sin., vol. 27(12), p. 1547-1552, (2006).

Wildburger et al., "Neuroprotective effects of blockers for T-type calcium channels", Molecular Neurodegeneration, vol. 4, p. 1-8, (2009).

Wouters et al., "Pharmaceutical Salts and Co-crystals", RSC Drug Discovery, (2012).

Xie et al., "Validation of High Throughput Screening Assays Against Three Subtypes of $Ca_v3$ T-Type Channels Using Molecular and Pharmacologic Approaches", Assay and Drug Development Technologies, vol. 5(2), p. 191-203, (2007).

Yaari et al., "Recruitment of apical dendritic T-type $Ca^{2+}$ channels by backpropagating spikes underlies de novo intrinsic bursting in hippocampal epileptogenesis", J. Physiol., vol. 580, p. 435-450, (2007).

Yang et al., "The T-type calcium channel as a new therapeutic target for Parkinson's disease", Pflugers Arch-Eur. J. Physiol., vol. 466, p. 747-755, (2014).

Yang et al., "Short-Acting T-Type Calcium Channel Antagonists Significantly Modify Sleep Architecture in Rodents", Med. Chem. Lett., vol. 1, p. 504-509, (2010).

Zamponi et al., "Role of voltage-gated calcium channels in epilepsy", Eur. J Phys., vol. 460(2), p. 395-403, (2010).

TRIAZOLE COMPOUNDS AS T-TYPE CALCIUM CHANNEL BLOCKERS

CROSS REFERENCE TO RELATED APPLICATIONS

This application is a United States Application under 35 U.S.C. 371 claiming benefit of PCT Application No. PCT/EP2015/070934, filed on Sep. 14, 2015, which claims the benefit of PCT Application No. PCT/EP2014/069592, filed on Sep. 15, 2014, the contents of each of which are incorporated herein by reference.

The present invention relates to novel triazole compounds and their use as T-type calcium channel blockers in the treatment or prevention of various diseases or disorders where calcium T channels are involved, to pharmaceutical compositions containing these derivatives, and to processes for their preparation.

Intracellular calcium concentrations control important life processes such as signal transduction pathways, hormones and neurotransmitter release, muscular contraction, gene expression and cell division. Control of calcium influx across the cellular membrane is in part regulated by a family of transmembrane proteins termed voltage-gated calcium channels (VOCs). They are activated by changes in electrical potential difference across the membrane and have been further classified into different subtypes based on biophysical and pharmacological considerations: Cav1.x (L-type for Long-lasting), Cav2.x (N-, P/Q- and R-types; N for Neuronal, P for Purkinje cells, Q (after P) and R for Remaining or Resistant) and Cav3.x (T-type for Transient). The L, N, P and Q-type channels activate at more positive potentials (high voltage activated) and display diverse kinetics and voltage-dependent properties. The T-type class (or "low voltage-activated") is characterized by fast inactivation (transient) and small conductance (tiny) and is composed of three members due to the different main pore-forming α1 subunits: Cav3.1 (α1 G), Cav3.2 (α1 H) and Cav3.3 (α1 I).

Nearly all "excitable" cells, such as neurons of the central nervous system (CNS), peripheral nerve cells and muscle cells, including those of skeletal muscles, cardiac muscles, and venous and arterial smooth muscles, have voltage-dependent calcium channels. In consequence, calcium T channels have been linked to various human diseases and disorders, such as especially epilepsy, pain, neuropathic pain, sleep disorders, sleep disturbances, schizophrenia, essential tremors, Parkinson's disease, neurodegenerative disorders, depression, anxiety, psychosis, autism, drug addiction, hypertension, cardiac arrhythmias, heart block, cancer, diabetes, infertility and sexual dysfunction (Bourinet, E.; Alloui, A.; Monteil, A.; Barrere, C.; Couette, B.; Poirot, O.; Pages, A.; McRory, J.; Snutch, T. P.; Eschalier, A.; Nargeot, J., EMBO J 2005, 24 (2), 315-324; Flatters, S. J. L., Drugs Fut. 2005, 30(6), 573-580; Giordanetto, F.; Knerr, L.; Wallberg, A., Expert Opin Ther Pat 2011, 21 (1), 85-101; Huguenard, J. R.; Prince, D. A., J Neurosci 1994, 14 (9), 5485-502; Lory, P.; Mezghrani, A., IDrugs 2010, 13 (7), 467-71; McGivern, J. G., Drug Discov Today 2006, 11 (5-6), 245-53; Uslaner, J. M.; Vardigan, J. D.; Drott, J. M.; Uebele, V. N.; Renger, J. J.; Lee, A.; Li, Z.; Le, A. D.; Hutson, P. H., Biol Psychiatry 2010, 68 (8), 712-8; Wildburger, N. C.; Lin-Ye, A.; Baird, M. A.; Lei, D.; Bao, J., Mol Neurodegener 2009, 4, 44).

In the brain, T-type calcium channels are essential for regulating neuronal excitability and burst firing, both in the central and peripheral nervous system (Lambert, R. C.; Bessaih, T.; Crunelli, V.; Leresche, N., Pflugers Arch 2014, 466 (3), 415-23.). They are linked to diseases or disorders where abnormal oscillatory activity occurs in the brain, as well as diseases or disorders where there is abnormal coupling of activity, particular through the thalamus. They are particularly linked to an increasing number of neurological disorders such as the epilepsy disorders and neuropathic pain.

T-type calcium channels play a role in regulating neuronal firing patterns under normal physiological conditions, such as during sleep rhythms (Anderson, M. P.; Mochizuki, T.; Xie, J.; Fischler, W.; Manger, J. P.; Talley, E. M.; Scammell, T. E.; Tonegawa, S., Proc Natl Acad Sci USA 2005, 102 (5), 1743-8; Destexhe, A.; Contreras, D.; Sejnowski, T. J.; Steriade, M., J Neurophysiol 1994, 72 (2), 803-18; Lee, J.; Kim, D.; Shin, H. S., Proc Natl Acad Sci USA 2004, 101 (52), 18195-9; Steriade, M., Trends Neurosci 2005, 28 (6), 317-24.). However, T-type calcium channels are also involved in pathophysiological conditions such as epilepsy, autism, hypertension, atrial fibrillation, congenital heart failure, pain, psychoses and cancer (for review, see Iftinca, M. C., J Med Life 2011, 4 (2), 126-38).

T-type calcium channels are critical players in the development of idiopathic generalized seizures in humans and animals (Cheong, E.; Shin, H. S., Pflugers Arch 2014, 466 (4), 719-34; Khosravani, H.; Zamponi, G. W., Physiol Rev 2006, 86 (3), 941-66; Zamponi, G. W.; Lory, P.; Perez-Reyes, E., Pflugers Arch 2010, 460 (2), 395-403). In animals, knockout of Cav3.1 calcium channels protects mice from absence seizures (Kim, D.; Song, I.; Keum, S.; Lee, T.; Jeong, M. J.; Kim, S. S.; McEnery, M. W.; Shin, H. S., Neuron 2001, 31 (1), 35-45; Song, I.; Kim, D.; Choi, S.; Sun, M.; Kim, Y.; Shin, H. S., J Neurosci 2004, 24 (22), 5249-57). In rat models of absence epilepsy (GAERS or WAG/Rij), a gain of function mutation of the Cav3.2 gene has been reported (Powell, K. L.; Cain, S. M.; Ng, C.; Sirdesai, S.; David, L. S.; Kyi, M.; Garcia, E.; Tyson, J. R.; Reid, C. A.; Bahlo, M.; Foote, S. J.; Snutch, T. P.; O'Brien, T. J., J Neurosci 2009, 29 (2), 371-80), as well as elevated levels of Cav3.1 and Cav3.2 mRNA and an increase in the amplitude of the T-type calcium current in comparison to normal rat strain (Broicher, T.; Kanyshkova, T.; Meuth, P.; Pape, H. C.; Budde, T., Mol Cell Neurosci 2008, 39 (3), 384-99; Talley, E. M.; Solorzano, G.; Depaulis, A.; Perez-Reyes, E.; Bayliss, D. A., Brain Res Mol Brain Res 2000, 75 (1), 159-65; Tsakiridou, E.; Bertollini, L.; de Curtis, M.; Avanzini, G.; Pape, H. C., J Neurosci 1995, 15 (4), 3110-7; Powell, K. L.; Cain, S. M.; Ng, C.; Sirdesai, S.; David, L. S.; Kyi, M.; Garcia, E.; Tyson, J. R.; Reid, C. A.; Bahlo, M.; Foote, S. J.; Snutch, T. P.; O'Brien, T. J., J Neurosci 2009, 29 (2), 371-80). In human, number of mutations have been described in Cav3.2 channels in patients with childhood absence and other forms of idiopathic generalized epilepsies (Heron, S. E.; Khosravani, H.; Varela, D.; Bladen, C.; Williams, T. C.; Newman, M. R.; Scheffer, I. E.; Berkovic, S. F.; Mulley, J. C.; Zamponi, G. W., Ann Neurol 2007, 62 (6), 560-8; Khosravani, H.; Zamponi, G. W., Physiol Rev 2006, 86 (3), 941-66; Zamponi, G. W.; Lory, P.; Perez-Reyes, E., Pflugers Arch 2010, 460 (2), 395-403). Those mutations are predicted to cause a gain of function with increase in calcium current, or can trigger an alteration of the balance between excitatory and inhibitory neuronal elements. As direct consequence, it may result in an increased spiking behavior in neurons that exhibit this rebound bursting, thereby contributing to the generation of epileptiform discharges.

In another type of epilepsy, i.e. the temporal lobe epilepsy, it has been shown in the pilocarpine rodent model that T-type calcium currents were uppregulated after status epilepticus and suggest a role of this channel in long-lasting modification of neuronal firing mode (regular to burst firing) and potential contribution to the development and expression of an epileptic condition after SE (Yaari, Y.; Yue, C.; Su, H., *J Physiol* 2007, 580 (2), 435-50; Becker, A. J.; Pitsch, J.; Sochivko, D.; Opitz, T.; Staniek, M.; Chen, C. C.; Campbell, K. P.; Schoch, S.; Yaari, Y.; Beck, H., *J Neurosci* 2008, 28 (49), 13341-53; Graef, J. D.; Nordskog, B. K.; Wiggins, W. F.; Godwin, D. W., *J Neurosci* 2009, 29 (14), 4430-41; Su, H.; Sochivko, D.; Becker, A.; Chen, J.; Jiang, Y.; Yaari, Y.; Beck, H., *J Neurosci* 2002, 22 (9), 3645-55).

Increased activity of T-type calcium channel has been associated to neuropathic and inflammatory pain states (for review, see Todorovic, S. M.; Jevtovic-Todorovic, V., *Br J Pharmacol* 2011, 163 (3), 484-95). When nociceptors are in an increased state of responsiveness, they often respond to normal sensory stimuli as if painful (allodynia) and to mildly painful stimuli as though they were acutely painful (hyperalgesia). The electrophysiological answer of these altered pain responses, include lower thresholds of activation, increased frequency of firing in response to suprathreshold stimuli and spontaneous firing (Coderre, T. J.; Katz, J.; Vaccarino, A. L.; Melzack, R., *Pain* 1993, 52 (3), 259-85; Bhave, G.; Gereau, R. W. t., *J Neurobiol* 2004, 61 (1), 88-106). T-type calcium channel are abundantly expressed in nociceptors, spinal dorsal horn and thalamic neurons (Talley, E. M.; Cribbs, L. L.; Lee, J. H.; Daud, A.; Perez-Reyes, E.; Bayliss, D. A., *J Neurosci* 1999, 19 (6), 1895-911) and increased T-type channel activity has been linked to neuropathic and inflammatory pain states in animals and humans (Jagodic, M. M.; Pathirathna, S.; Nelson, M. T.; Mancuso, S.; Joksovic, P. M.; Rosenberg, E. R.; Bayliss, D. A.; Jevtovic-Todorovic, V.; Todorovic, S. M., *J Neurosci* 2007, 27 (12), 3305-16; Todorovic, S. M.; Jevtovic-Todorovic, V., *Channels (Austin)* 2007, 1 (4), 238-45; Jagodic, M. M.; Pathirathna, S.; Joksovic, P. M.; Lee, W.; Nelson, M. T.; Naik, A. K.; Su, P.; Jevtovic-Todorovic, V.; Todorovic, S. M., *J Neurophysiol* 2008, 99 (6), 3151-6). T-channels may play a role in the decrease of the threshold for action potential firing in dorsal root ganglia (DRG) cells that express T-channels (Nelson, M. T.; Todorovic, S. M.; Perez-Reyes, E., *Curr Pharm Des* 2006, 12 (18), 2189-97; Jagodic, M. M.; Pathirathna, S.; Nelson, M. T.; Mancuso, S.; Joksovic, P. M.; Rosenberg, E. R.; Bayliss, D. A.; Jevtovic-Todorovic, V.; Todorovic, S. M., *J Neurosci* 2007, 27 (12), 3305-16). T-type calcium channels would play a role of amplifiers of peripheral pain signals. Pharmacological and molecular downregulation of the function of these channels in DRG neurons supports the notion that T-channels contribute to the chronic pain associated with peripheral axonal injury (Bourinet, E.; Alloui, A.; Monteil, A.; Barrere, C.; Couette, B.; Poirot, O.; Pages, A.; McRory, J.; Snutch, T. P.; Eschalier, A.; Nargeot, J., *EMBO J* 2005, 24 (2), 315-24; Wen, X. J.; Li, Z. J.; Chen, Z. X.; Fang, Z. Y.; Yang, C. X.; Li, H.; Zeng, Y. M., *Acta Pharmacol Sin* 2006, 27 (12), 1547-52) (or for review, see Jevtovic-Todorovic, V.; Todorovic, S. M., *Cell Calcium* 2006, 40 (2), 197-203).

In addition, T-type calcium channel activity is upregulated during diabetic neuropathy (Hall, K. E.; Sima, A. A.; Wiley, J. W., *J Physiol* 1995, 486 (2), 313-22; Jagodic, M. M.; Pathirathna, S.; Nelson, M. T.; Mancuso, S.; Joksovic, P. M.; Rosenberg, E. R.; Bayliss, D. A.; Jevtovic-Todorovic, V.; Todorovic, S. M., *J Neurosci* 2007, 27 (12), 3305-16). Selective knock-down of DRG Cav3.2 currents in vivo has effectively reversed mechanical and thermal hyperalgesia in STZ-induced diabetic neuropathy in rats (Messinger, R. B.; Naik, A. K.; Jagodic, M. M.; Nelson, M. T.; Lee, W. Y.; Choe, W. J.; Orestes, P.; Latham, J. R.; Todorovic, S. M.; Jevtovic-Todorovic, V., *Pain* 2009, 145 (1-2), 184-95). Furthermore, significant up-regulation of Cav3.2 T-channel mRNA in DRG tissue homogenates and concomitant up-regulation of Cav3.2 T-currents in nociceptive DRG cells has been reported in another model of painful diabetic neuropathy, leptin-deficient ob/ob mice (Latham, J. R.; Pathirathna, S.; Jagodic, M. M.; Choe, W. J.; Levin, M. E.; Nelson, M. T.; Lee, W. Y.; Krishnan, K.; Covey, D. F.; Todorovic, S. M.; Jevtovic-Todorovic, V., *Diabetes* 2009, 58 (11), 2656-65). In humans, extracellular recordings from the medial thalamus of patients with neurogenic pain have shown abnormalities of LTS-mediated bursts that could at least contribute to persistent pain (Jeanmonod, D.; Magnin, M.; Morel, A., *Brain* 1996, 119 (2), 363-75).

It has been shown that T-type calcium (Ca) channels in the CNS are closely associated with repetitive burst discharges or neuronal oscillations (Llinas, R.; Yarom, Y., *J Physiol* 1986, 376, 163-82; Gutnick, M. J.; Yarom, Y., *J Neurosci Methods* 1989, 28 (1-2), 93-9; Iftinca, M. C.; Zamponi, G. W., *Trends Pharmacol Sci* 2009, 30 (1), 32-40). Tremor is a common encountered involuntary movements, and it is associated with various neurological diseases or pathological conditions such as essential tremor (ET) and Parkinson's disease (PD) and its related disorders. As tremor-related neuronal activities may be closely related to repetitive or oscillatory activities in the CNS, controlling T-type Ca channels may have therapeutic effects. This hypothesis is supported by neuro-anatomical and functional expression of expression of T-type calcium channels in area involved pathophysiological mechanisms underlying harmaline-induced tremor, a pharmacological model of ET in rodents (Llinas, R.; Yarom, Y., *J Physiol* 1986, 376, 163-82; Cavelier, P.; Lohof, A. M.; Lonchamp, E.; Beekenkamp, H.; Mariani, J.; Bossu, J. L., *Neuroreport* 2008, 19 (3), 299-303). Moreover, animal data involving selective knockdown of the Cav3.1 gene or mice lacking the Cav3.1 gene showed that Cav3.1 channels play a specific role in ET (Park, Y. G.; Park, H. Y.; Lee, C. J.; Choi, S.; Jo, S.; Choi, H.; Kim, Y. H.; Shin, H. S.; Llinas, R. R.; Kim, D., *Proc Natl Acad Sci USA* 2010, 107 (23), 10731-6). On the other hand, the role of the other isoform of the T-type calcium channels (Cav3.2 and Cav 3.3) in this pathology is not known but cannot be excluded (Miwa, H.; Kondo, T., *Cerebellum* 2011, 10 (3), 563-9).

In Parkinson's disease (PD) patients, deep brain stimulation of the subthalamic nucleus has been shown to be an effective treatment for parkinsonian symptoms indicating a pivotal role of this area in the pathogenesis of PD: In patients, as well as in animal models of PD, this area seems to have an abnormal pattern of firing with an increase of the burst firing mode. And this burst firig mode has been shown to involve the T-type $Ca^{2+}$ channels (for review, see Yang, Y. C.; Tai, C. H.; Pan, M. K.; Kuo, C. C., *Pflugers Arch* 2014, 466 (4), 747-55).

The compounds of the present invention are potent calcium T channel blockers and therefore useful for the prevention or treatment of diseases or disorders where calcium T channels are involved.

1) A first aspect of the invention relates to novel compounds of the formula (I)

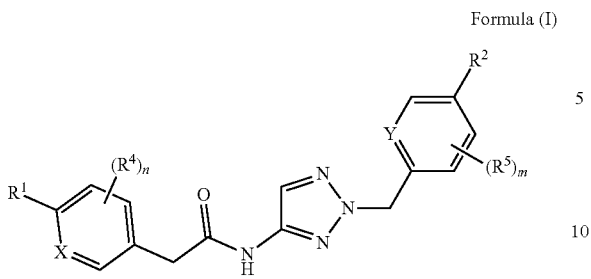

Formula (I)

wherein

X represents a ring carbon or a ring nitrogen atom;

R$^1$ represents (C$_{2-6}$)alkyl [in particular isopropyl, tert.-butyl, or isobutyl];

(C$_{2-4}$)alkyl mono-substituted with cyano, or (C$_{1-3}$) alkoxy (especially methoxy); [in particular such group is 1-methoxy-ethyl, or 1-cyano-1-methyl-ethyl];

(C$_{1-4}$)fluoroalkyl [in particular trifluoromethyl, 2,2,2-trifluoro-1,1-dimethyl-ethyl];

(C$_{1-3}$)fluoroalkoxy [in particular 2,2,2-trifluoroethoxy];

pentafluoro-sulfanyl;

(C$_{3-6}$)cycloalkyl-L$^1$- wherein said (C$_{3-6}$)cycloalkyl optionally contains one ring oxygen atom; wherein said (C$_{3-6}$)cycloalkyl is unsubstituted; or mono-substituted with fluoro, (C$_{1-3}$)alkyl (especially methyl), (C$_{1-3}$)alkoxy (especially methoxy), hydroxy, cyano, or (C$_{1-3}$)fluoroalkyl (especially trifluoromethyl); or di-substituted with fluoro, or tri-substituted with two fluoro substituents and a (C$_{1-3}$)alkyl (especially methyl) substituent; and the linker L$^1$ represents a direct bond, (C$_{1-2}$)alkylene, oxygen, or (C$_{1-2}$)alkylene-oxy (which is attached to the rest of the molecule through the oxygen atom);

[in particular such group (C$_{3-6}$)cycloalkyl-L$^1$- is cyclopropyl, oxetan-3-yl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];

5- or 6-membered heteroaryl, independently optionally mono-substituted with (C$_{1-3}$)alkyl (especially methyl);

—NR$^{11}$R$^{12}$, wherein

R$^{11}$ and R$^{12}$ independently represent hydrogen, (C$_{1-3}$)alkyl, (C$_{2-3}$)fluoroalkyl, (C$_{3-6}$)cycloalkyl, (C$_{3-6}$)cycloalkyl mono- or di-substituted with fluoro, (C$_{3-6}$)cycloalkyl-(C$_{1-3}$)alkyl, (C$_{1-3}$)alkoxy-(C$_{2-3}$)alkyl [in particular such group —NR$^{11}$R$^{12}$ is dimethylamino, ethyl-methyl-amino, diethyl-amino, cyclopropyl-methyl-amino, (2-methoxy-ethyl)-methyl-amino, (cyclopropylmethyl)-methyl-amino, or (2,2-difluoro-ethyl)-methyl-amino];

or R$^{11}$ and R$^{12}$, together with the nitrogen atom to which they are attached to, form a 4-to-6 membered ring which is optionally mono- or di-substituted with fluoro; a 2-oxo-pyrrolidinyl group; or a morpholinyl group [in particular such group —NR$^{11}$R$^{12}$ is azetidinyl, 3-fluoro-azetidinyl, 3,3-difluoro-azetidinyl, pyrrolidinyl, 3-fluoro-pyrrolidinyl, 3,3-difluoro-pyrrolidinyl, or 2-oxo-pyrrolidinyl];

and (R$^4$)$_n$ represents one or two optional substituents (i.e. n represents the integer 0, 1, or 2) independently selected from (C$_{1-4}$)alkyl (especially methyl), (C$_{1-4}$)alkoxy (especially methoxy), (C$_{1-3}$)fluoroalkyl (especially trifluoromethyl), (C$_{1-3}$)fluoroalkoxy (especially trifluoromethoxy), halogen (especially fluoro), and cyano [especially (R$^4$)$_n$ is absent (i.e. n=0); or (R$^4$)$_n$ represents one halogen or methyl substituent];

or R$^1$ together with (R$^4$)$_n$ forms a non-aromatic 5- or 6-membered ring which is fused to the phenyl/pyridine ring; wherein said 5- or 6-membered ring optionally contains one or two heteroatoms independently selected from oxygen and nitrogen; wherein said fused 5- or 6-membered non-aromatic ring independently is optionally further mono-substituted with oxo; or di-, tri-, or tetra-substituted wherein one substituent is oxo and the remaining are (C$_{1-3}$)alkyl (especially methyl); [in particular such non-aromatic 5- or 6-membered ring fused to the phenyl/pyridine ring forms, together with the phenyl/pyridine ring, a group selected from 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, or 3,3-dimethyl-2,3-dihydro-benzofuran-5-yl];

or R$^1$ together with (R$^4$)$_n$ forms an aromatic 5- or 6-membered ring which is fused to the phenyl/pyridine ring; wherein said 5- or 6-membered ring optionally contains one or two nitrogen atoms, wherein said fused 5- or 6-membered aromatic ring independently is optionally further mono- or di-substituted wherein the substituents are independently selected from (C$_{1-4}$)alkyl (notably (C$_{1-3}$)alkyl, especially methyl, propyl, isopropyl, butyl), (C$_{3-6}$)cycloalkyl (especially cyclopropyl, cyclobutyl), (C$_1$)fluoroalkyl (especially trifluoromethyl), or cyano [in particular such aromatic 5- or 6-membered ring fused to the phenyl/pyridine ring forms, together with the phenyl/pyridine ring, a group selected from 1-methyl-1H-pyrazolo[3,4-b]pyridin-5-yl, 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 1-methyl-1H-indol-6-yl, 2-methyl-1H-indol-5-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl- 1H-benzoimidazol-6-yl, 1-methyl-1H-benzoimidazol-5-yl, 1-methyl-1H-benzoimidazol-6-yl, or quinolin-7-yl];

Y represents a ring carbon or a ring nitrogen atom; and $R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, ethoxy, isopropoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy, 2,2,2-trifluoroethoxy); $(C_{1-3})$alkoxy-$(C_{2-3})$alkoxy (especially 2-methoxy-ethoxy); halogen; cyano; or —$NR^{21}R^{22}$, wherein $R^{21}$ and $R^{22}$ independently represent hydrogen, or $(C_{1-3})$alkyl, or $R^{21}$ and $R^{22}$, together with the nitrogen atom to which they are attached to, form a 4-to-6 membered ring optionally mono- or di-substituted with fluoro, or a morpholinyl group;

and $(R^5)_m$ represents one or two optional substituents (i.e. m represents the integer 0, 1, or 2) independently selected from $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen; cyano; $(C_{1-3})$fluoroalkyl (especially trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent; preferably $(R^5)_m$ is absent].

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

Furthermore, in some instances, the compounds of the present invention may be present in tautomeric forms. Any such tautomeric form is encompassed. For example, it is well understood that, in case a benzimidazole moiety is unsubstituted on the ring nitrogen having a free valency such benzimidazole moiety represents tautomeric forms. Thus, further substituents of the benzimidazole moiety may be attached in the position(s) ortho to the bridgehead atoms (i.e. attached in position(s) 4 and/or 7), and/or in the position(s) meta to the bridgehead atoms, (i.e. attached in position(s) 5 and/or 6). It is understood that the two ortho, and, respectively, the two meta positions are considered equivalent. For example, the group 4-methyl-1H-benzoimidazol-2-yl is understood to signify the same group as 7-methyl-1H-benzoimidazol-2-yl and 4-methyl-3H-benzoimidazol-2-yl and 7-methyl-3H-benzoimidazol-2-yl.

The present invention also includes isotopically labelled, especially $^2$H (deuterium) labelled compounds of formula (I) according to embodiments 1) to 18), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, variably attached bonds may be used for substituents or groups (e.g. $(R^4)_n$ and $(R^5)_m$). In such case it is meant that any such substituent or group may be attached to any carbon atom of the ring system to which the variable attached bond is drawn into, provided that said carbon atom is not already substituted.

In this patent application, a bond drawn as a dotted line shows the point of attachment of the radical drawn. For example, the radical drawn below

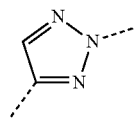

is a 2H-triazol-2,4-diyl group.

Where the plural form is used for compounds, salts, pharmaceutical compositions, diseases and the like, this is intended to mean also a single compound, salt, pharmaceutical composition, disease or the like.

Any reference to compounds of formula (I) according to embodiments 1) to 19) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 18), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, bromine, or iodine, preferably fluorine or chlorine, especially fluorine.

The term "cyano" refers to a group —CN.

The term "alkyl", used alone or in combination, refers to a saturated straight or branched chain hydrocarbon group containing one to six (especially one to four) carbon atoms. The term "$(C_{x-y})$alkyl" (x and y each being an integer), refers to an alkyl group as defined before, containing x to y carbon atoms. In case a $(C_{1-y})$alkyl group (or, in general, a $(C_{x-y})$ alkyl group) is used in combination with another substituent, the term means that said substituent is linked through a $(C_{1-y})$alkyl group (or a $(C_{x-y})$alkyl group, respectively) to the rest of the molecule. In some instances such group is also referred to as $(C_{1-y})$alkylene. For example a $(C_{1-6})$alkyl group contains from one to six carbon atoms. Examples of $(C_{1-6})$alkyl groups are the $(C_{1-4})$alkyl groups methyl, ethyl, n-propyl, isopropyl, n-butyl, sec.-butyl, tert.-butyl, and isobutyl, as well as n-pentyl, and isopentyl. Preferred are methyl, ethyl, n-propyl, and isopropyl. Most preferred is methyl. For the substituent $R^1$ preferred examples of $(C_{2-6})$ alkyl are isopropyl, tert.-butyl, and isobutyl; especially tert.-butyl.

Examples of $(C_{2-4})$alkyl groups which are mono-substituted with cyano, or $(C_{1-3})$alkoxy as used for $R^1$ are 1-methoxy-ethyl, and 1-cyano-1-methyl-ethyl.

The term "alkoxy" means a group of the formula alkyl-O— in which the term alkyl has the previously given significance. The term "$(C_{x-y})$alkoxy" (x and y being an integer) refers to a straight or branched chain alkoxy group containing x to y carbon atoms. Examples of alkoxy groups are the $(C_{1-4})$alkoxy groups methoxy, ethoxy, n-propoxy, isopropoxy, n-butoxy, isobutoxy, sec-butoxy and tert.-butoxy. Preferred is methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. A preferred example is trifluoromethyl. Examples of $(C_{2-3})$fluoroalkyl groups include 2-fluoroethyl and 2,2,2-trifluoroethyl. In the specific case of $(C_{1-4})$fluoroalkyl groups, the fluoroalkyl group contains from one to four carbon atoms in which one to nine hydrogen atoms have been replaced with fluorine. Examples of $(C_{1-4})$fluoroalkyl groups as used for $R^1$ include trifluoromethyl, 2-fluoroethyl, 2,2-difluoroethyl, 2,2,2-trifluoroethyl, and 2,2,2-trifluoro-1,1-dimethyl-ethyl; especially trifluoromethyl, and 2,2,2-trifluoro-1,1-dimethyl-ethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Preferred examples are trifluoromethoxy, difluoromethoxy and 2,2,2-trifluoroethoxy. Representative examples of fluoroalkoxy groups as used for $R^1$ include trifluoromethoxy, difluoromethoxy, 2-fluoroethoxy, 2,2-difluoroethoxy and 2,2,2-trifluoroethoxy; especially 2,2,2-trifluoroethoxy.

The term "cycloalkyl" refers to a saturated mono- or bicyclic carbocyclic ring containing three to eight carbon atoms. The term "$(C_{x-y})$cycloalkyl" (x and y each being an integer), refers to a cycloalkyl group as defined before containing x to y carbon atoms. For example a $(C_{3-6})$ cycloalkyl group refers to a saturated monocyclic carbocyclic ring containing three to six carbon atoms. Examples of cycloalkyl groups are cyclopropyl, cyclobutyl, cyclopentyl, and cyclohexyl. Preferred is cyclopropyl.

The term "$(C_{3-6})$cycloalkyl, wherein the cycloalkyl may optionally contain a ring oxygen atom", refers to a monocyclic cycloalkyl group as defined before. In addition, one ring carbon atom of said cycloalkyl may be replaced by an oxygen atom. For the substituent $R^1$, examples of such groups are especially cyclopropyl, cyclobutyl, and, in addition, oxetan-3-yl. Said groups are unsubstituted or substituted as explicitly defined.

The term "$(C_{3-6})$cycloalkyl-$(C_{1-3})$alkyl" refers to a $(C_{3-6})$cycloalkyl group as explicitly defined which group is linked to the rest of the molecule through a $(C_{1-3})$alkylene group as defined before. For the substituent $R^1$, the $(C_{1-2})$ alkylene group part of $(C_{3-6})$cycloalkyl-$(C_{1-2})$alkyl is in particular a methylene group.

The term "$(C_{3-6})$cycloalkyl-oxy" refers to a $(C_{3-6})$cycloalkyl group as explicitly defined which is linked to the rest of the molecule through an oxygen atom.

The term "$(C_{3-6})$cycloalkyl-$(C_{1-2})$alkylene-oxy" refers to a $(C_{3-6})$cycloalkyl group as explicitly defined which is linked to the rest of the molecule through a —$(CH_2)_{1-2}$—O— group. For the substituent $R^1$, the —$(C_{1-2})$alkylene-oxy group part of $(C_{3-6})$cycloalkyl-$(C_{1-2})$alkylene-oxy is in particular a —$CH_2$—O— group.

The term "$(C_{1-3})$alkoxy-$(C_{2-3})$alkoxy" refers to a $(C_{1-3})$ alkoxy-group as defined before which is attached to the rest of the molecule through a $(C_{2-3})$alkoxy group as defined before. An example is 2-methoxy-ethoxy.

The term "$(C_{1-3})$alkoxy-$(C_{2-3})$alkyl" means a $(C_{1-3})$ alkoxy-group as defined before which is attached to the rest of the molecule through a $(C_{2-3})$alkylene group as defined before. An example is 2-methoxy-ethyl.

The term "aryl", used alone or in combination, means phenyl or naphthyl, preferably phenyl. Likewise, an arylene group is an aryl group as defined before having two points of attachment to the respective rests of the molecule. The above-mentioned aryl/arylene groups are unsubstituted or substituted as explicitly defined.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are 5-membered heteroaryl such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl; 6-membered heteroaryl such as pyridinyl, pyrimidinyl, pyridazinyl, pyrazinyl; and bicyclic heteroaryl such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

In case two substituents form an aromatic 5- or 6-membered ring optionally containing one or two nitrogen atoms which ring is fused to a phenyl/pyridine ring, examples of such thus formed bicyclic heteroaryl rings are pyrrolo[2,3-b]pyridinyl, pyrazolo[3,4-b]pyridinyl, indolyl, indazolyl, quinoxalinyl, benzoimidazolyl, and quinolinyl; especially pyrazolo[3,4-b]pyridinyl, indolyl, and indazolyl. The above-mentioned groups do not carry further substituents on the phenyl/pyridine part of the ring, whereas said aromatic 5- or 6-membered ring may be unsubstituted or substituted as explicitly defined.

In case two substituents form a non-aromatic 5- or 6-membered ring optionally containing one or two heteroatoms, which ring is fused to a phenyl/pyridine ring, examples of such thus formed bicyclic partially aromatic rings are 2,3-dihydro-benzooxazolyl, 3,4-dihydro-2H-benzo[1,4]oxazinyl, 2,3-dihydro-1H-indolyl, and 2,3-dihydro-benzofuranyl; especially 2,3-dihydro-1H-indolyl. The above-mentioned groups do not carry further substituents on the phenyl/pyridine part of the ring, whereas said non-aromatic 5- or 6-membered ring may be unsubstituted or substituted as explicitly defined.

Examples of —$NR^{11}R^{12}$ groups as used for $R^1$ are especially disubstituted amino groups wherein one substituent is methyl or ethyl, and the other is $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl, $(C_{1-3})$ alkoxy-$(C_{2-3})$alkyl. Examples are dimethylamino, ethyl-methyl-amino, diethylamino, cyclopropyl-methyl-amino, (2-methoxyethyl)-methyl-amino, (cyclopropylmethyl)-methyl-amino, and (2,2-difluoro-ethyl)-methyl-amino; preferred examples are dimethylamino, diethylamino, cyclopropyl-methyl-amino, and (cyclopropylmethyl)-methyl-amino. Examples of —$NR^{11}R^{12}$ groups wherein $R^{11}$ and $R^{12}$ together with the nitrogen atom to which they are attached to form a 4-to-6 membered ring as used for $R^1$ are especially the four and five-membered rings azetidinyl, 3-fluoro-azetidinyl, 3,3-difluoro-azetidinyl, pyrrolidinyl (preferred), 3-fluoro-pyrrolidinyl, 3,3-difluoro-pyrrolidinyl (preferred).

Further embodiments of the invention are presented hereinafter:

2) A second embodiment relates to compounds according to embodiment 1), wherein
X represents a ring carbon atom.

3) A second embodiment relates to compounds according to embodiment 1), wherein
X represents a ring nitrogen atom.

4) Another embodiment relates to compounds according to any one of embodiments 1) to 3), wherein
$R^1$ represents
- $(C_{2-6})$alkyl [in particular isopropyl, tert.-butyl, or isobutyl];
- $(C_{2-4})$alkyl mono-substituted with cyano, or $(C_{1-3})$ alkoxy (especially methoxy); [in particular such group is 1-methoxy-ethyl, or 1-cyano-1-methyl-ethyl];
- $(C_{1-4})$fluoroalkyl [in particular trifluoromethyl, 2,2,2-trifluoro-1,1-dimethyl-ethyl];
- $(C_{1-3})$fluoroalkoxy [in particular 2,2,2-trifluoroethoxy]; pentafluoro-sulfanyl;
- $(C_{3-6})$cycloalkyl-$L^1$- wherein
  said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
  the linker $L^1$ represents a direct bond, $(C_{1-2})$alkylene, oxygen, or $(C_{1-2})$alkylene-oxy (which is attached to the rest of the molecule through the oxygen atom);
  [in particular such group $(C_{3-6})$cycloalkyl-$L^1$- is cyclopropyl, oxetan-3-yl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- —$NR^{11}R^{12}$, wherein
  $R^{11}$ and $R^{12}$ independently represent hydrogen, $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl [in particular such group —$NR^{11}R^{12}$ is dimethylamino, ethyl-methyl-amino, diethylamino, cyclopropyl-methyl-amino, (cyclopropylmethyl)-methyl-amino, or (2,2-difluoro-ethyl)-methyl-amino];
  or $R^{11}$ and $R^{12}$, together with the nitrogen atom to which they are attached to, form an azetidinyl or a pyrrolidinyl ring, both independently optionally mono- or di-substituted with fluoro; [in particular such group —$NR^{11}R^{12}$ is azetidinyl, 3-fluoro-azetidinyl, 3,3-difluoro-azetidinyl, pyrrolidinyl, 3-fluoro-pyrrolidinyl, or 3,3-difluoro-pyrrolidinyl];

and $(R^4)_n$ represents one optional substituent (i.e. n represents the integer 0, or 1) selected from $(C_{1-4})$alkyl (especially methyl), $(C_{1-4})$alkoxy (especially methoxy), $(C_{1-3})$fluoroalkyl (especially trifluoromethyl), $(C_{1-3})$ fluoroalkoxy (especially trifluoromethoxy), halogen (especially fluoro), and cyano [especially $(R^4)_n$ is absent (i.e. n=0); or $(R^4)_n$ represents one halogen or methyl substituent];

or $R^1$ together with $(R^4)_n$ forms a non-aromatic 5- or 6-membered ring which is fused to the phenyl/pyridine ring to form a bicyclic ring system; wherein said bicyclic ring system is selected from 2,3-dihydro-benzooxazolyl, 3,4-dihydro-2H-benzo[1,4]oxazinyl, 2,3-dihydro-1H-indolyl, and 2,3-dihydro-benzofuranyl; wherein said non-aromatic 5- or 6-membered ring part of said bicyclic ring system independently is optionally further mono-substituted with oxo; or di-, tri-, or tetra-substituted wherein one substituent is oxo and the remaining are $(C_{1-3})$alkyl (especially methyl); [in particular such bicyclic ring system is 3,3-dimethyl-2-oxo-2,3-dihydro-1H-indol-5-yl, or 1,3,3-trimethyl-2-oxo-2,3-dihydro-1H-indol-5-yl];

or $R^1$ together with $(R^4)_n$ forms an aromatic 5- or 6-membered ring which is fused to the phenyl/pyridine ring to form a bicyclic aromatic ring system selected from pyrazolo[3,4-b]pyridinyl, pyrrolo[2,3-b]pyridinyl, indolyl, indazolyl, quinoxalinyl, benzoimidazolyl, and quinolinyl (especially indolyl or indazolyl); wherein said fused 5- or 6-membered aromatic ring part of said aromatic bicyclic ring system independently is optionally further mono- or di-substituted wherein the substituents are independently selected from $(C_{1-3})$alkyl (especially methyl, propyl, isopropyl, butyl), $(C_{3-6})$ cycloalkyl (especially cyclopropyl, cyclobutyl), $(C_1)$ fluoroalkyl (especially trifluoromethyl), or cyano [in particular such aromatic part of said aromatic bicyclic ring system is a group selected from 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl- 1H-indol-5-yl, 1-methyl-1H-indol-6-yl, 2-methyl-1H-indol-5-yl, 1,3-dimethyl-1H-indol-5-yl, or 1,3-dimethyl-1H-indol-6-yl].

5) Another embodiment relates to compounds according to any one of embodiments 1) to 3), wherein
$R^1$ represents
- $(C_{2-6})$alkyl [in particular isopropyl, or tert.-butyl];
- $(C_{2-4})$alkyl mono-substituted with cyano, or $(C_{1-3})$alkoxy (especially methoxy); [in particular such group is 1-methoxy-ethyl, or 1-cyano-1-methyl-ethyl];
- $(C_{1-4})$fluoroalkyl [in particular trifluoromethyl, 2,2,2-trifluoro-1,1-dimethyl-ethyl];
- $(C_{1-3})$fluoroalkoxy [in particular 2,2,2-trifluoroethoxy];
- pentafluoro-sulfanyl;
- $(C_{3-6})$cycloalkyl-$L^1$- wherein
    said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
    the linker $L^1$ represents a direct bond, $(C_{1-2})$alkylene, oxygen, or $(C_{1-2})$alkylene-oxy (which is attached to the rest of the molecule through the oxygen atom); [in particular such group $(C_{3-6})$cycloalkyl-$L^1$- is cyclopropyl, oxetan-3-yl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, or 1-cyano-cyclopropyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- —$NR^{11}R^{12}$, wherein
    $R^{11}$ and $R^{12}$ independently represent $(C_{1-3})$alkyl, $(C_{2-3})$fluoroalkyl, $(C_{3-6})$cycloalkyl, $(C_{3-6})$cycloalkyl mono- or di-substituted with fluoro, or $(C_{3-6})$cycloalkyl-$(C_{1-3})$alkyl [in particular such group —$NR^{11}R^{12}$ is dimethylamino, diethylamino, cyclopropyl-methyl-amino, or (cyclopropylmethyl)-methyl-amino];
    or $R^{11}$ and $R^{12}$, together with the nitrogen atom to which they are attached to, form an azetidinyl or a pyrrolidinyl ring, both independently optionally mono- or di-substituted with fluoro; [in particular such group —$NR^{11}R^{12}$ is azetidinyl, 3-fluoro-azetidinyl, 3,3-difluoro-azetidinyl, pyrrolidinyl, 3-fluoro-pyrrolidinyl, or 3,3-difluoro-pyrrolidinyl];

and $(R^4)_n$ represents one optional substituent (i.e. n represents the integer 0, or 1) selected from $(C_{1-4})$alkyl (especially methyl), $(C_{1-4})$alkoxy (especially methoxy), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent];

or $R^1$ together with $(R^4)_n$ forms an aromatic 5- or 6-membered ring which is fused to the phenyl/pyridine ring to form a bicyclic aromatic ring system selected from pyrazolo[3,4-b]pyridinyl, indolyl, and indazolyl (especially indolyl or indazolyl); wherein said fused 5- or 6-membered aromatic ring part of said aromatic bicyclic ring system independently is optionally further mono- or di-substituted wherein the substituents are independently selected from $(C_{1-3})$alkyl (especially methyl, propyl, isopropyl, butyl), $(C_{3-6})$cycloalkyl (especially cyclopropyl), or $(C_1)$fluoroalkyl (especially trifluoromethyl), [in particular such aromatic part of said aromatic bicyclic ring system is a group selected from 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 1-methyl-1H-indol-6-yl, 2-methyl-1H-indol-5-yl, 1,3-dimethyl-1H-indol-5-yl, or 1,3-dimethyl-1H-indol-6-yl].

6) Another embodiment relates to compounds according to any one of embodiments 1) to 3), wherein
$R^1$ represents
- $(C_{2-6})$alkyl [in particular isopropyl, or tert.-butyl];
- $(C_{1-4})$fluoroalkyl [in particular trifluoromethyl, 2,2,2-trifluoro-1,1-dimethyl-ethyl];
- $(C_{1-3})$fluoroalkoxy [in particular 2,2,2-trifluoroethoxy];
- $(C_{3-6})$cycloalkyl-$L^1$- wherein
    said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
    the linker $L^1$ represents a direct bond, $(C_{1-2})$alkylene, oxygen, or $(C_{1-2})$alkylene-oxy (which is attached to the rest of the molecule through the oxygen atom); [in particular such group $(C_{3-6})$cycloalkyl-$L^1$- is cyclopropyl, oxetan-3-yl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, or 1-cyano-cyclopropyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- —$NR^{11}R^{12}$, wherein
    $R^{11}$ and $R^{12}$ independently represent $(C_{1-3})$alkyl, $(C_{3-6})$cycloalkyl, or $(C_{3-6})$cycloalkyl-$(C_{1-3})$alkyl [in particular such group —$NR^{11}R^{12}$ is dimethylamino, diethylamino, cyclopropyl-methyl-amino, or (cyclopropylmethyl)-methyl-amino];
    or $R^{11}$ and $R^{12}$, together with the nitrogen atom to which they are attached to, form an azetidinyl or a pyrrolidinyl ring (especially a pyrrolidinyl ring), both independently optionally mono- or di-substituted with fluoro; [in particular such group —$NR^{11}R^{12}$ is azetidinyl, 3-fluoro-azetidinyl, 3,3-difluoro-azetidinyl, pyrrolidinyl, 3-fluoro-pyrrolidinyl, or 3,3-difluoro-pyrrolidinyl];

and $(R^4)_n$ represents one optional substituent (i.e. n represents the integer 0, or 1) selected from $(C_{1-4})$alkyl (especially methyl), (C$_{1-4}$)alkoxy (especially methoxy), (C$_{1-3}$) fluoroalkyl (especially trifluoromethyl), (C$_{1-3}$)fluoroalkoxy (especially trifluoromethoxy), halogen (especially fluoro), and cyano [especially (R$^4$)$_n$ is absent (i.e. n=0); or (R$^4$)$_n$ represents one halogen or methyl substituent].

7) Another embodiment relates to compounds according to any one of embodiments 1) to 3), wherein
R$^1$ represents
- (C$_{2-6}$)alkyl [in particular isopropyl, or tert.-butyl];
- (C$_{1-4}$)fluoroalkyl [in particular trifluoromethyl, 2,2,2-trifluoro-1,1-dimethyl-ethyl];
- (C$_{1-3}$)fluoroalkoxy [in particular 2,2,2-trifluoroethoxy];
- (C$_{3-6}$)cycloalkyl wherein
  said (C$_{3-6}$)cycloalkyl optionally contains one ring oxygen atom; wherein said (C$_{3-6}$)cycloalkyl is unsubstituted, or mono-substituted with fluoro, (C$_{1-3}$)alkyl (especially methyl), (C$_{1-3}$)alkoxy (especially methoxy), cyano, or (C$_{1-3}$)fluoroalkyl (especially trifluoromethyl), or di-substituted with fluoro; [in particular cyclopropyl, oxetan-3-yl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, or 1-cyano-cyclopropyl];
- (C$_{3-6}$)cycloalkyl-oxy- wherein
  said (C$_{3-6}$)cycloalkyl optionally contains one ring oxygen atom; wherein said (C$_{3-6}$)cycloalkyl is unsubstituted, or mono- or di-substituted with fluoro; [in particular cyclopropyl-oxy, oxetan-3-yl-oxy, cyclobutyl-oxy, or 3,3-difluoro-cyclobutyl-oxy];
- (C$_{3-6}$)cycloalkyl-(C$_{1-2}$)alkylene-oxy- wherein
  said (C$_{3-6}$)cycloalkyl optionally contains one ring oxygen atom; wherein said (C$_{3-6}$)cycloalkyl is unsubstituted, or mono-substituted with fluoro, or (C$_{1-3}$)alkyl (especially methyl), or di-substituted with fluoro, or tri-substituted with two fluoro substituents and a (C$_{1-3}$)alkyl (especially methyl) substituent; [in particular oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- —NR$^{11}$R$^{12}$, wherein
  R$^{11}$ and R$^{12}$, together with the nitrogen atom to which they are attached to, form a pyrrolidinyl ring optionally di-substituted with fluoro [in particular pyrrolidinyl, 3,3-difluoro-pyrrolidinyl];

and (R$^4$)$_n$ represents one optional substituent (i.e. n represents the integer 0, or 1) selected from (C$_{1-4}$)alkyl (especially methyl), (C$_{1-4}$)alkoxy (especially methoxy), (C$_{1-3}$)fluoroalkyl (especially trifluoromethyl), (C$_{1-3}$) fluoroalkoxy (especially trifluoromethoxy), halogen (especially fluoro), and cyano [especially (R$^4$)$_n$ is absent (i.e. n=0); or (R$^4$)$_n$ represents one halogen or methyl substituent];

or R$^1$ together with (R$^4$)$_n$ forms an aromatic 5- or 6-membered ring which is fused to the phenyl/pyridine ring to form a bicyclic aromatic ring system selected from pyrazolo[3,4-b]pyridinyl, indolyl, and indazolyl (especially indolyl or indazolyl); wherein said fused 5- or 6-membered aromatic ring part of said aromatic bicyclic ring system independently is optionally further mono- or di-substituted wherein the substituents are independently selected from (C$_{1-3}$)alkyl (especially methyl, propyl, isopropyl, butyl), (C$_{3-6}$)cycloalkyl (especially cyclopropyl), or (C$_1$)fluoroalkyl (especially trifluoromethyl), [in particular such aromatic part of said aromatic bicyclic ring system is a group selected from 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 1-methyl-1H-indol-6-yl, 2-methyl-1H-indol-5-yl, 1,3-dimethyl-1H-indol-5-yl, or 1,3-dimethyl-1H-indol-6-yl].

8) Another embodiment relates to compounds according to any one of embodiments 1) to 3), wherein R$^1$ represents
- (C$_{2-6}$)alkyl [in particular isopropyl, or tert.-butyl];
- (C$_{1-4}$)fluoroalkyl [in particular trifluoromethyl, 2,2,2-trifluoro-1,1-dimethyl-ethyl];
- (C$_{1-3}$)fluoroalkoxy [in particular 2,2,2-trifluoroethoxy];
- (C$_{3-6}$)cycloalkyl wherein
  said (C$_{3-6}$)cycloalkyl optionally contains one ring oxygen atom; wherein said (C$_{3-6}$)cycloalkyl is unsubstituted, or mono-substituted with fluoro, (C$_{1-3}$)alkyl (especially methyl), (C$_{1-3}$)alkoxy (especially methoxy), cyano, or (C$_{1-3}$)fluoroalkyl (especially trifluoromethyl), or di-substituted with fluoro; [in particular cyclopropyl, oxetan-3-yl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, or 1-cyano-cyclopropyl];
- (C$_{3-6}$)cycloalkyl-oxy- wherein
  said (C$_{3-6}$)cycloalkyl optionally contains one ring oxygen atom; wherein said (C$_{3-6}$)cycloalkyl is unsubstituted, or mono- or di-substituted with fluoro; [in particular cyclopropyl-oxy, oxetan-3-yl-oxy, cyclobutyl-oxy, or 3,3-difluoro-cyclobutyl-oxy];
- (C$_{3-6}$)cycloalkyl-(C$_{1-2}$)alkylene-oxy- wherein
  said (C$_{3-6}$)cycloalkyl optionally contains one ring oxygen atom; wherein said (C$_{3-6}$)cycloalkyl is unsubstituted, or mono-substituted with fluoro, or (C$_{1-3}$)alkyl (especially methyl), or di-substituted with fluoro, or tri-substituted with two fluoro substituents and a (C$_{1-3}$)alkyl (especially methyl) substituent; [in particular oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- —NR$^{11}$R$^{12}$, wherein
  R$^{11}$ and R$^{12}$, together with the nitrogen atom to which they are attached to, form a pyrrolidinyl ring optionally di-substituted with fluoro [in particular pyrrolidinyl, 3,3-difluoro-pyrrolidinyl];

and (R$^4$)$_n$ represents one optional substituent (i.e. n represents the integer 0, or 1) selected from (C$_{1-4}$)alkyl (especially methyl), (C$_{1-4}$)alkoxy (especially methoxy), (C$_{1-3}$)fluoroalkyl (especially trifluoromethyl), (C$_{1-3}$) fluoroalkoxy (especially trifluoromethoxy), halogen (especially fluoro), and cyano [especially (R$^4$)$_n$ is absent (i.e. n=0); or (R$^4$)$_n$ represents one halogen or methyl substituent].

9) Another embodiment relates to compounds according to any one of embodiments 1) to 3), wherein R$^1$ represents
- (C$_{2-6}$)alkyl [in particular isopropyl, or tert.-butyl, preferably tert.-butyl];

($C_{1-4}$)fluoroalkyl [in particular trifluoromethyl, 2,2,2-trifluoro-1,1-dimethyl-ethyl; preferably 2,2,2-trifluoro-1,1-dimethyl-ethyl];
($C_{1-3}$)fluoroalkoxy [in particular 2,2,2-trifluoroethoxy];
($C_{3-6}$)cycloalkyl wherein
said ($C_{3-6}$)cycloalkyl optionally contains one ring oxygen atom; wherein said ($C_{3-6}$)cycloalkyl is mono-substituted with fluoro or ($C_{1-3}$)fluoroalkyl (especially trifluoromethyl), or di-substituted with fluoro; [in particular 3-fluoro-oxetan-3-yl, 3,3-difluoro-cyclobutyl, 1-trifluoromethyl-cyclopropyl, or 2-trifluoromethyl-cyclopropyl; especially 3-fluoro-oxetan-3-yl, 3,3-difluoro-cyclobutyl, or 1-trifluoromethyl-cyclopropyl; preferably 1-trifluoromethyl-cyclopropyl]; or
($C_{3-6}$)cycloalkyl-oxy- wherein
said ($C_{3-6}$)cycloalkyl optionally contains one ring oxygen atom; wherein said ($C_{3-6}$)cycloalkyl is unsubstituted, or di-substituted with fluoro; [in particular cyclopropyl-oxy, oxetan-3-yl-oxy, cyclobutyl-oxy, or 3,3-difluoro-cyclobutyl-oxy, especially 3,3-difluoro-cyclobutyl-oxy];
and $(R^4)_n$ represents one optional substituent (i.e. n represents the integer 0, or 1) selected from ($C_{1-4}$)alkyl (especially methyl), or halogen (especially fluoro) [especially $(R^4)_n$ is absent (i.e. n=0); or $(R^4)_n$ represents one halogen or methyl substituent].

10) Another embodiment relates to compounds according to any one of embodiments 1) to 3), wherein
$R^1$ together with $(R^4)_n$ forms a non-aromatic 5- or 6-membered ring which is fused to the phenyl/pyridine ring to form a bicyclic ring system; wherein said bicyclic ring system is selected from 2,3-dihydro-benzooxazolyl, 3,4-dihydro-2H-benzo[1,4]oxazinyl, 2,3-dihydro-1H-indolyl, and 2,3-dihydro-benzofuranyl; wherein said non-aromatic 5- or 6-membered ring part of said bicyclic ring system independently is optionally further mono-substituted with oxo; or di-, tri-, or tetra-substituted wherein one substituent is oxo and the remaining are ($C_{1-3}$)alkyl (especially methyl); [in particular such bicyclic ring system is a group selected from 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, or 3,3-dimethyl-2,3-dihydro-benzofuran-5-yl];
or (notably) $R^1$ together with $(R^4)_n$ forms an aromatic 5- or 6-membered ring which is fused to the phenyl/pyridine ring to form a bicyclic aromatic ring system selected from pyrazolo[3,4-b]pyridinyl, pyrrolo[2,3-b]pyridinyl, indolyl, indazolyl, quinoxalinyl, benzoimidazolyl, and quinolinyl; wherein said fused 5- or 6-membered aromatic ring part of said aromatic bicyclic ring system independently is optionally further mono- or di-substituted wherein the substituents are independently selected from ($C_{1-3}$)alkyl (especially methyl, propyl, isopropyl, butyl), ($C_{3-6}$)cycloalkyl (especially cyclopropyl, cyclobutyl), ($C_1$)fluoroalkyl (especially trifluoromethyl), or cyano [especially such aromatic bicyclic ring system is indolyl or indazolyl, both mono-substituted with methyl; in particular such aromatic bicyclic ring system is a group selected from 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 1-methyl-1H-indol-6-yl, 2-methyl-1H-indol-5-yl, 1,3-dimethyl-1H-indol-5-yl, or 1,3-dimethyl-1H-indol-6-yl].

11) Another embodiment relates to compounds according to any one of embodiments 1) to 3), wherein the fragment

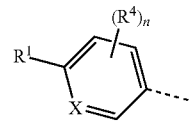

represents 4-isopropyl-phenyl, 4-dimethylamino-phenyl, 4-trifluoromethyl-phenyl, 4-tert.-butyl-phenyl, 4-(1-methoxy-ethyl)-phenyl, 4-(cyclopropyl-oxy)-phenyl, 4-(oxetan-3-yl)-phenyl, 4-(3-fluoro-oxetan-3-yl)-phenyl, 4-(cyclobutyl-oxy)-phenyl, 4-(3-methyl-oxetan-3-yl)-phenyl, 4-(1-cyano-cyclopropyl)-phenyl, 4-(1-cyano-1-methyl-ethyl)-phenyl, 4-(pentafluoro-sulfanyl)-phenyl, 3-methyl-4-(2,2,2-trifluoroethoxy)-phenyl, 4-(3-methoxy-oxetan-3-yl)-phenyl, 4-(oxetan-3-yl-methoxy)-phenyl, 4-(2-trifluoromethyl-cyclopropyl)-phenyl, 4-(1-trifluoromethyl-cyclopropyl)-phenyl, 4-((3-fluoro-oxetan-3-yl)-methoxy)-phenyl, 4-((3-methyl-oxetan-3-yl)-methoxy)-phenyl, 4-(3,3-difluoro-cyclobutyl-oxy)-phenyl, 4-(2,2,2-trifluoro-1,1-dimethyl-ethyl)-phenyl, 4-((3,3-difluoro-cyclobutyl)-methoxy)-phenyl, 4-((3,3-difluoro-1-methyl-cyclobutyl)-methoxy)-phenyl; 2-(pyrrolidin-1-yl)-pyridin-5-yl, 2-(cyclopropyl(methyl)amino)-pyridin-5-yl, 2-(diethylamino)-pyridin-5-yl, 3-fluoro-2-(pyrrolidin-1-yl)-pyridin-5-yl, 2-((cyclopropylmethyl)-methyl-amino)-pyridin-5-yl, 2-(3,3-difluoro-pyrrolidin-1-yl)-pyridin-5-yl; 3,3-dimethyl-2-oxo-2,3-dihydro-1H-indol-5-yl, 1,3,3-trimethyl-2-oxo-2,3-dihydro-1H-indol-5-yl, 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 2-methyl-1H-indol-5-yl, 1,3-dimethyl-1H-indol-5-yl, or 1,3-dimethyl-1H-indol-6-yl.

12) Another embodiment relates to compounds according to any one of embodiments 1) to 11), wherein
Y represents a ring carbon or a ring nitrogen atom;
$R^2$ represents ($C_{1-4}$)alkyl (especially methyl, ethyl, isopropyl, isobutyl, tert.-butyl); ($C_{1-4}$)alkoxy (especially methoxy, ethoxy); ($C_{1-3}$)fluoroalkyl (especially trifluoromethyl); ($C_{1-3}$)fluoroalkoxy (especially difluoromethoxy, trifluoromethoxy); ($C_{1-3}$)alkoxy-($C_{2-3}$)alkoxy (especially 2-methoxy-ethoxy); halogen (especially fluoro); or cyano; and
$(R^5)_m$ represents one or two optional substituents (i.e. m represents the integer 0, 1, or 2) independently selected from ($C_{1-4}$)alkyl (especially methyl); ($C_{1-4}$)alkoxy (especially methoxy); halogen (especially fluoro); cyano; ($C_{1-3}$)fluoroalkyl (especially trifluoromethyl); and ($C_{1-3}$)fluoroalkoxy (especially trifluoromethoxy); [especially $(R^5)_m$ is absent (i.e. m=0), or $(R^5)_m$ represents one halogen (especially fluoro) substituent; preferably $(R^5)_m$ is absent].

13) Another embodiment relates to compounds according to any one of embodiments 1) to 11), wherein
Y represents a ring nitrogen atom; and
$R^2$ represents $(C_{1-4})$alkyl (especially methyl); $(C_{1-4})$alkoxy (especially methoxy); $(C_{1-3})$fluoroalkyl (especially trifluoromethyl); $(C_{1-3})$fluoroalkoxy (especially difluoromethoxy, trifluoromethoxy); halogen (especially fluoro); or cyano; and
$(R^5)_m$ represents one or two optional substituents (i.e. m represents the integer 0, 1, or 2) independently selected from $(C_{1-4})$alkyl (especially methyl); $(C_{1-4})$alkoxy (especially methoxy); halogen (especially fluoro); cyano; $(C_{1-3})$fluoroalkyl (especially trifluoromethyl); and $(C_{1-3})$fluoroalkoxy (especially trifluoromethoxy); [especially $(R^5)_m$ is absent (i.e. m=0), or $(R^5)_m$ represents one halogen (especially fluoro) substituent; preferably $(R^5)_m$ is absent]; or
Y represents a ring carbon atom; and
$R^2$ represents $(C_{1-4})$alkyl (especially methyl); $(C_{1-4})$alkoxy (especially methoxy, ethoxy); $(C_{1-3})$fluoroalkyl (especially trifluoromethyl); $(C_{1-3})$fluoroalkoxy (especially difluoromethoxy, trifluoromethoxy); $(C_{1-3})$alkoxy-$(C_{2-3})$alkoxy (especially 2-methoxy-ethoxy); halogen (especially fluoro); or cyano; and
$(R^5)_m$ represents one or two optional substituents (i.e. m represents the integer 0, 1, or 2) independently selected from $(C_{1-4})$alkyl (especially methyl); $(C_{1-4})$alkoxy (especially methoxy); halogen (especially fluoro); cyano; $(C_{1-3})$fluoroalkyl (especially trifluoromethyl); and $(C_{1-3})$fluoroalkoxy (especially trifluoromethoxy); [especially $(R^5)_m$ is absent (i.e. m=0), or $(R^5)_m$ represents one halogen (especially fluoro) substituent; preferably $(R^5)_m$ is absent].

14) Another embodiment relates to compounds according to any one of embodiments 1) to 11), wherein
Y represents a ring nitrogen atom; and
$R^2$ represents cyano; and
$(R^5)_m$ is absent (i.e. n=0); or
Y represents a ring carbon atom; and
$R^2$ represents $(C_{1-4})$alkyl (especially methyl); $(C_{1-4})$alkoxy (especially methoxy, ethoxy); $(C_{1-3})$fluoroalkoxy (especially difluoromethoxy, trifluoromethoxy); $(C_{1-3})$alkoxy-$(C_{2-3})$alkoxy (especially 2-methoxy-ethoxy); halogen (especially fluoro); or cyano; and
$(R^5)_m$ represents one or two optional substituents (i.e. m represents the integer 0, 1, or 2) independently selected from $(C_{1-4})$alkyl (especially methyl); $(C_{1-4})$alkoxy (especially methoxy); halogen; and cyano; [especially $(R^5)_m$ is absent (i.e. m=0), or $(R^5)_m$ represents one halogen substituent; preferably $(R^5)_m$ is absent].

15) Another embodiment relates to compounds according to any one of embodiments 1) to 11), wherein the fragment

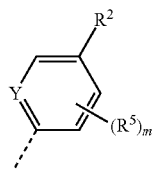

represents 4-fluorophenyl, 4-methylphenyl, 4-fluoro-3-cyano-phenyl, 3,4-difluorophenyl, 3,5-difluoro-4-methoxy-phenyl, 3-fluoro-4-methoxy-phenyl, 4-cyano-3-fluoro-phenyl, 4-cyano-3-methyl-phenyl, 3-cyano-4-methyl-phenyl, 4-methoxyphenyl, 4-ethoxyphenyl, 3,4-dimethoxyphenyl, 4-fluoro-3-methoxy-phenyl; 3,4-difluoro-5-methoxy-phenyl, 3-cyano-4-methoxy-phenyl, 4-cyano-3-methoxy-phenyl, 4-cyano-3-fluoro-5-methoxy-phenyl, 4-cyanophenyl, 4-(2-methoxy-ethoxy)-phenyl, 4-difluoromethoxy-phenyl, 4-trifluoromethoxy-phenyl, 3-fluoro-4-difluoromethoxy-phenyl; 3-fluoro-4-trifluoromethoxy-phenyl; or 5-cyano-pyridin-2-yl.

16) Another embodiment relates to compounds according to embodiment 1), wherein
X represents a ring carbon or a ring nitrogen atom; and $R^1$ represents
$(C_{2-6})$alkyl [in particular isopropyl, or tert.-butyl];
$(C_{2-4})$alkyl mono-substituted with cyano, or $(C_{1-3})$ alkoxy (especially methoxy); [in particular such group is 1-methoxy-ethyl, or 1-cyano-1-methyl-ethyl];
$(C_{1-4})$fluoroalkyl [in particular trifluoromethyl, 2,2,2-trifluoro-1,1-dimethyl-ethyl];
$(C_{1-3})$fluoroalkoxy [in particular 2,2,2-trifluoroethoxy];
pentafluoro-sulfanyl;
$(C_{3-6})$cycloalkyl-$L^1$- wherein
said $(C_{3-6})$cycloalkyl optionally contains one ring oxygen atom; wherein said $(C_{3-6})$cycloalkyl is unsubstituted; or mono-substituted with fluoro, $(C_{1-3})$alkyl (especially methyl), $(C_{1-3})$alkoxy (especially methoxy), cyano, or $(C_{1-3})$fluoroalkyl (especially trifluoromethyl); or di-substituted with fluoro, or tri-substituted with two fluoro substituents and a $(C_{1-3})$alkyl (especially methyl) substituent; and
the linker $L^1$ represents a direct bond, oxygen, or $(C_{1-2})$alkylene-oxy (which is attached to the rest of the molecule through the oxygen atom);
[in particular such group $(C_{3-6})$cycloalkyl-$L^1$- is oxetan-3-yl, 3-fluoro-oxetan-3-yl, 3-methoxy-oxetan-3-yl, 3-methyl-oxetan-3-yl, 1-trifluoromethyl-cyclopropyl, 2-trifluoromethyl-cyclopropyl, or 1-cyano-cyclopropyl; or it is cyclopropyl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
—$NR^{11}R^{12}$, wherein
$R^{11}$ and $R^{12}$ independently represent $(C_{1-3})$alkyl, $(C_{3-6})$cycloalkyl, or $(C_{3-6})$cycloalkyl-$(C_{1-3})$alkyl [in particular such group —$NR^{11}R^{12}$ is dimethylamino, diethylamino, cyclopropyl-methyl-amino, or (cyclopropylmethyl)-methyl-amino];
or $R^{11}$ and $R^{12}$, together with the nitrogen atom to which they are attached to, form a 4-to-6 membered ring which is optionally mono- or di-substituted with fluoro [in particular such group —$NR^{11}R^{12}$ is pyrrolidinyl, or 3,3-difluoro-pyrrolidinyl];
and $(R^4)_n$ represents one optional substituent (i.e. n represents the integer 0, or 1) selected from $(C_{1-4})$alkyl (especially methyl), and halogen (especially fluoro) [especially $(R^4)_n$ is absent (i.e. n=0); or $(R^4)_n$ represents one halogen or methyl substituent];
or X represents a ring carbon atom; and $R^1$ together with $(R^4)_n$ forms a non-aromatic 5-membered ring which is fused to the phenyl ring; wherein said 5-membered ring contains one nitrogen atom; wherein said fused 5-membered non-aromatic ring independently is di-, tri-, or tetra-substituted wherein one substituent is oxo and the remaining are $(C_{1-3})$alkyl (especially methyl); [in particular such non-aromatic 5-membered ring fused to the phenyl ring forms, together with the phenyl ring, a group selected from 3,3-dimethyl-2-oxo-2,3-dihydro-1H-indol-5-yl, or 1,3,3-trimethyl-2-oxo-2,3-dihydro-1H-indol-5-yl];

or X represents a ring carbon or a ring nitrogen atom; and $R^1$ together with $(R^4)_n$ forms an aromatic 5-membered ring which is fused to the phenyl/pyridine ring; wherein said 5-membered ring contains one or two nitrogen atoms, wherein said fused 5-membered aromatic ring independently is optionally further mono- or di-substituted wherein the substituents are independently selected from $(C_{1-4})$alkyl (especially methyl, ethyl, propyl, isopropyl, butyl), $(C_{3-6})$cycloalkyl (especially cyclopropyl), or $(C_1)$fluoroalkyl (especially trifluoromethyl) [in particular such aromatic 5-membered ring fused to the phenyl/pyridine ring forms, together with the phenyl/pyridine ring, a group selected from 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 2-methyl-1H-indol-5-yl, 1,3-dimethyl-1H-indol-5-yl, or 1,3-dimethyl-1H-indol-6-yl];

Y represents a ring carbon or a ring nitrogen atom; and $R^2$ represents $(C_{1-4})$alkyl (especially methyl); $(C_{1-4})$alkoxy (especially methoxy, or ethoxy); $(C_{1-3})$fluoroalkoxy (especially difluoromethoxy, or trifluoromethoxy); $(C_{1-3})$alkoxy-$(C_{2-3})$alkoxy (especially 2-methoxy-ethoxy); halogen (especially fluoro); or cyano; and $(R^5)_m$ represents one or two optional substituents (i.e. m represents the integer 0, 1, or 2) independently selected from $(C_{1-4})$alkyl (especially methyl); $(C_{1-4})$alkoxy (especially methoxy); halogen (especially fluoro); or cyano; [especially $(R^5)_m$ is absent (i.e. m=0), or $(R^5)_m$ represents one halogen substituent; preferably $(R^5)_m$ is absent].

17) Another embodiment relates to compounds according to embodiment 1), wherein
X represents a ring carbon or a ring nitrogen atom; and $R^1$ represents
$(C_{2-6})$alkyl [in particular isopropyl, or tert.-butyl];
$(C_{2-4})$alkyl mono-substituted with cyano, or $(C_{1-3})$alkoxy (especially methoxy); [in particular such group is 1-methoxy-ethyl, or 1-cyano-1-methyl-ethyl];
$(C_{1-3})$fluoroalkoxy [in particular 2,2,2-trifluoroethoxy];
$(C_{3-6})$cycloalkyl-$L^1$- wherein
said $(C_{3-6})$cycloalkyl optionally contains one ring oxygen atom; wherein said $(C_{3-6})$cycloalkyl is unsubstituted; or mono-substituted with fluoro, $(C_{1-3})$alkyl (especially methyl), $(C_{1-3})$alkoxy (especially methoxy), cyano, or $(C_{1-3})$fluoroalkyl (especially trifluoromethyl); or di-substituted with fluoro; and
the linker $L^1$ represents a direct bond, oxygen, or methylenoxy (which is attached to the rest of the molecule through the oxygen atom);
[in particular such group $(C_{3-6})$cycloalkyl-$L^1$- is oxetan-3-yl, 3-fluoro-oxetan-3-yl, 3-methoxy-oxetan-3-yl, 3-methyl-oxetan-3-yl, 1-trifluoromethyl-cyclopropyl, 2-trifluoromethyl-cyclopropyl, or 1-cyano-cyclopropyl; or it is cyclopropyl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, or (3-methyl-oxetan-3-yl)-methoxy];

—$NR^{11}R^{12}$, wherein
$R^{11}$ and $R^{12}$ independently represent $(C_{1-3})$alkyl, $(C_{3-6})$cycloalkyl, or $(C_{3-6})$cycloalkyl-$(C_{1-3})$alkyl [in particular such group —$NR^{11}R^{12}$ is dimethylamino, diethylamino, cyclopropyl-methyl-amino, or (cyclopropylmethyl)-methyl-amino];
or $R^{11}$ and $R^{12}$, together with the nitrogen atom to which they are attached to, form a 4-to-6 membered ring which is optionally mono- or di-substituted with fluoro [in particular such group —$NR^{11}R^{12}$ is pyrrolidinyl, or 3,3-difluoro-pyrrolidinyl];

and $(R^4)_n$ represents one optional substituent (i.e. n represents the integer 0, or 1) selected from $(C_{1-4})$alkyl (especially methyl), and halogen (especially fluoro) [especially $(R^4)_n$ is absent (i.e. n=0); or $(R^4)_n$ represents one halogen or methyl substituent];

or X represents a ring carbon atom; and $R^1$ together with $(R^4)_n$ forms an aromatic 5-membered ring which is fused to the phenyl ring; wherein said 5-membered ring contains one or two nitrogen atoms, wherein said fused 5-membered aromatic ring independently is optionally further mono- or di-substituted wherein the substituents are independently selected from $(C_{1-4})$alkyl (especially methyl, ethyl, propyl, isopropyl, butyl), $(C_{3-6})$cycloalkyl (especially cyclopropyl), or $(C_1)$fluoroalkyl (especially trifluoromethyl) [in particular such aromatic 5-membered ring fused to the phenyl ring forms, together with the phenyl ring, a group selected from 1H-indol-5-yl, 1H-indol-6-yl, 1-methyl-1H-indazol-5-yl, 1-methyl-1H-indazol-6-yl, 1-ethyl-1H-indazol-5-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 2-methyl-1H-indol-5-yl, 1,3-dimethyl-1H-indol-5-yl, or 1,3-dimethyl-1H-indol-6-yl];

Y represents a ring carbon or a ring nitrogen atom; and $R^2$ represents $(C_{1-4})$alkyl (especially methyl); $(C_{1-4})$alkoxy (especially methoxy, or ethoxy); $(C_{1-3})$fluoroalkoxy (especially difluoromethoxy, or trifluoromethoxy); halogen (especially fluoro); or cyano; and $(R^5)_m$ represents one or two optional substituents (i.e. m represents the integer 0, 1, or 2) independently selected from $(C_{1-4})$alkyl (especially methyl); $(C_{1-4})$alkoxy (especially methoxy); halogen (especially fluoro); or cyano; [especially $(R^5)_m$ is absent (i.e. m=0), or $(R^5)_m$ represents one halogen substituent; preferably $(R^5)_m$ is absent].

18) The invention, thus, relates to compounds of the formula (I) as defined in embodiment 1), or to such compounds further limited by the characteristics of any one of embodiments 2) to 15), under consideration of their respective dependencies; to pharmaceutically acceptable salts thereof; and to the use of such compounds as medicaments especially in the treatment of diseases or disorders where calcium T channels are involved as described herein below. For avoidance of any doubt, especially the following embodiments relating to the compounds of formula (I) are thus possible and intended and herewith specifically disclosed in individualized form:

1, 2+1, 3+1, 4+1, 4+2+1, 4+3+1, 5+1, 5+2+1, 5+3+1, 6+1, 6+2+1, 6+3+1, 7+1, 7+2+1, 7+3+1, 8+1, 8+2+1, 8+3+1, 9+1, 9+2+1, 9+3+1, 10+1, 10+2+1, 10+3+1, 11+1, 11+2+1, 11+3+1, 12+1, 12+2+1, 12+3+1, 12+4+1, 12+4+2+1, 12+4+3+1, 12+5+1, 12+5+2+1, 12+5+3+1, 12+6+1, 12+6+2+1, 12+6+3+1, 12+7+1, 12+7+2+1, 12+7+3+1, 12+8+1, 12+8+2+1, 12+8+3+1, 12+9+1, 12+9+2+1, 12+9+3+1, 12+10+1, 12+10+2+1, 12+10+3+1, 12+11+1, 12+11+2+1, 12+11+3+1, 13+1, 13+2+1, 13+3+1, 13+4+1, 13+4+2+1, 13+4+3+1, 13+5+1, 13+5+2+1, 13+5+3+1, 13+6+1, 13+6+2+1, 13+6+3+1, 13+7+1, 13+7+2+1, 13+7+3+1, 13+8+1, 13+8+2+1, 13+8+3+1, 13+9+1, 13+9+2+1, 13+9+3+1, 13+10+1, 13+10+2+1, 13+10+3+1, 13+11+1, 13+11+2+1, 13+11+3+1, 14+1, 14+2+1, 14+3+1, 14+4+1, 14+4+2+1, 14+4+3+1, 14+5+1, 14+5+2+1, 14+5+3+1, 14+6+1, 14+6+2+1, 14+6+3+1, 14+7+1, 14+7+2+1, 14+7+3+1, 14+8+1, 14+8+2+1, 14+8+3+1, 14+9+1, 14+9+2+1, 14+9+3+1, 14+10+1, 14+10+2+1, 14+10+3+1, 14+11+1, 14+11+2+1, 14+11+3+1, 15+1, 15+2+1, 15+3+1, 15+4+1, 15+4+2+1, 15+4+3+1, 15+5+1, 15+5+2+1, 15+5+3+1, 15+6+1, 15+6+2+1, 15+6+3+1, 15+7+1, 15+7+2+1, 15+7+3+1, 15+8+1, 15+8+2+1, 15+8+3+1, 15+9+1, 15+9+2+1, 15+9+3+1, 15+10+1, 15+10+2+1, 15+10+3+1, 15+11+1, 15+11+2+1, 15+11+3+1, 16+1, 17+1;

In the list above the numbers refer to the embodiments according to their numbering provided hereinabove whereas "+" indicates the dependency from another embodiment. The different individualized embodiments are separated by commas. In other words, "15+11+2+1" for example refers to embodiment 15) depending on embodiment 11), depending on embodiment 2), depending on embodiment 1), i.e. embodiment "15+11+2+1" corresponds to the compounds of formula (I) according to embodiment 1) further limited by all the features of the embodiments 2), 11), and 15).

19) A further embodiment relates to compounds of formula (I) which are selected from:
N-[2-(4-Fluoro-benzyl)-2H-[1,2,3]triazol-4-yl]-2-(4-isopropyl-phenyl)-acetamide;
2-(4-Dimethylamino-phenyl)-N-[2-(4-fluoro-benzyl)-2H-[1,2,3]triazol-4-yl]-acetamide;
N-[2-(3,4-Difluoro-benzyl)-2H-[1,2,3]triazol-4-yl]-2-(4-isopropyl-phenyl)-acetamide;
N-[2-(3,4-Difluoro-benzyl)-2H-[1,2,3]triazol-4-yl]-2-(1-methyl-1H-indazol-5-yl)-acetamide;
N-[2-(3,4-Difluoro-benzyl)-2H-[1,2,3]triazol-4-yl]-2-(1-methyl-1H-indol-5-yl)-acetamide;
N-[2-(3,4-Difluoro-benzyl)-2H-[1,2,3]triazol-4-yl]-2-(1H-indol-6-yl)-acetamide;
2-(4-Cyclobutoxy-phenyl)-N-[2-(3,4-difluoro-benzyl)-2H-[1,2,3]triazol-4-yl]-acetamide;
2-(4-Cyclopropoxy-phenyl)-N-[2-(3,4-difluoro-benzyl)-2H-[1,2,3]triazol-4-yl]-acetamide;
2-[6-(Cyclopropyl(methyl)amino)-pyridin-3-yl]-N-[2-(3,4-difluoro-benzyl)-2H-[1,2,3]triazol-4-yl]-acetamide;
2-[6-(Cyclopropylmethyl-methyl-amino)-pyridin-3-yl]-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-[4-(1-methoxy-ethyl)-phenyl]-acetamide;
N-[2-(3,4-Difluoro-benzyl)-2H-[1,2,3]triazol-4-yl]-2-[4-(3-fluoro-oxetan-3-yl)-phenyl]-acetamide;
N-[2-(3,4-Difluoro-benzyl)-2H-[1,2,3]triazol-4-yl]-2-(1H-indol-5-yl)-acetamide;
2-(6-Diethylamino-pyridin-3-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-[6-(3,3-difluoro-pyrrolidin-1-yl)-pyridin-3-yl]-acetamide;
N-[2-(3,4-Difluoro-benzyl)-2H-[1,2,3]triazol-4-yl]-2-(6-pyrrolidin-1-yl-pyridin-3-yl)-acetamide;
N-[2-(3,4-Difluoro-benzyl)-2H-[1,2,3]triazol-4-yl]-2-(1,3,3-trimethyl-2-oxo-2,3-dihydro-1H-indol-5-yl)-acetamide;
N-[2-(3,4-Difluoro-benzyl)-2H-[1,2,3]triazol-4-yl]-2-[4-(3-methoxy-oxetan-3-yl)-phenyl]-acetamide;
N-[2-(3,4-Difluoro-benzyl)-2H-[1,2,3]triazol-4-yl]-2-(3,3-dimethyl-2-oxo-2,3-dihydro-1H-indol-5-yl)-acetamide;
N-[2-(3,4-Difluoro-benzyl)-2H-[1,2,3]triazol-4-yl]-2-[4-(3-methyl-oxetan-3-yl)-phenyl]-acetamide;
N-[2-(3,4-Difluoro-benzyl)-2H-[1,2,3]triazol-4-yl]-2-(4-oxetan-3-yl-phenyl)-acetamide;
2-(4-Isopropyl-phenyl)-N-[2-(4-methyl-benzyl)-2H-[1,2,3]triazol-4-yl]-acetamide;
2-(4-Isopropyl-phenyl)-N-[2-(4-methoxy-benzyl)-2H-[1,2,3]triazol-4-yl]-acetamide;
N-[2-(4-Cyano-benzyl)-2H-[1,2,3]triazol-4-yl]-2-(4-isopropyl-phenyl)-acetamide;
N-[2-(3,4-Difluoro-benzyl)-2H-[1,2,3]triazol-4-yl]-2-(1-ethyl-1H-indazol-5-yl)-acetamide;
N-[2-(3,4-Difluoro-benzyl)-2H-[1,2,3]triazol-4-yl]-2-(1,3-dimethyl-1H-indazol-5-yl)-acetamide;
2-(3-Cyclopropyl-1H-indazol-5-yl)-N-[2-(3,4-difluoro-benzyl)-2H-[1,2,3]triazol-4-yl]-acetamide;
2-(1-Butyl-1H-indazol-5-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-(2-methyl-1H-indol-5-yl)-acetamide;
2-(3-Butyl-1H-indazol-5-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-(1-isopropyl-1H-indazol-5-yl)-acetamide;
N-[2-(3,4-Difluoro-benzyl)-2H-[1,2,3]triazol-4-yl]-2-(1-propyl-1H-indazol-5-yl)-acetamide;
2-(3-Cyclopropyl-1-methyl-1H-indazol-5-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-(1-methyl-1H-pyrazolo[3,4-b]pyridin-5-yl)-acetamide;
N-[2-(3,4-Difluoro-benzyl)-2H-[1,2,3]triazol-4-yl]-2-(3-trifluoromethyl-1H-indazol-5-yl)-acetamide;
N-[2-(4-Ethoxy-benzyl)-2H-[1,2,3]triazol-4-yl]-2-(1-methyl-1H-indol-5-yl)-acetamide;
2-[6-(3,3-Difluoro-pyrrolidin-1-yl)-pyridin-3-yl]-N-[2-(4-ethoxy-benzyl)-2H-[1,2,3]triazol-4-yl]-acetamide;
N-[2-(4-Ethoxy-benzyl)-2H-[1,2,3]triazol-4-yl]-2-[4-(3-methyl-oxetan-3-yl)-phenyl]-acetamide;
2-(4-tert-Butyl-phenyl)-N-[2-(4-ethoxy-benzyl)-2H-[1,2,3]triazol-4-yl]-acetamide;
N-[2-(4-Ethoxy-benzyl)-2H-[1,2,3]triazol-4-yl]-2-(4-isopropyl-phenyl)-acetamide;
N-[2-(4-Ethoxy-benzyl)-2H-[1,2,3]triazol-4-yl]-2-(6-pyrrolidin-1-yl-pyridin-3-yl)-acetamide;
N-[2-(4-Ethoxy-benzyl)-2H-[1,2,3]triazol-4-yl]-2-(1-methyl-1H-indazol-5-yl)-acetamide;
2-(6-Diethylamino-pyridin-3-yl)-N-[2-(3,4-dimethoxy-benzyl)-2H-[1,2,3]triazol-4-yl]-acetamide;
2-[6-(3,3-Difluoro-pyrrolidin-1-yl)-pyridin-3-yl]-N-[2-(3,4-dimethoxy-benzyl)-2H-[1,2,3]triazol-4-yl]-acetamide;
2-(4-tert-Butyl-phenyl)-N-[2-(3,4-dimethoxy-benzyl)-2H-[1,2,3]triazol-4-yl]-acetamide;
N-[2-(3,4-Dimethoxy-benzyl)-2H-[1,2,3]triazol-4-yl]-2-(4-isopropyl-phenyl)-acetamide;

N-[2-(3,4-Dimethoxy-benzyl)-2H-[1,2,3]triazol-4-yl]-2-(6-pyrrolidin-1-yl-pyridin-3-yl)-acetamide;
N-[2-(4-Fluoro-benzyl)-2H-[1,2,3]triazol-4-yl]-2-(1-methyl-1H-indol-5-yl)-acetamide;
N-[2-(4-Fluoro-benzyl)-2H-[1,2,3]triazol-4-yl]-2-[4-(3-methyl-oxetan-3-yl)-phenyl]-acetamide;
2-(4-tert-Butyl-phenyl)-N-[2-(4-fluoro-benzyl)-2H-[1,2,3]triazol-4-yl]-acetamide;
N-[2-(4-Fluoro-benzyl)-2H-[1,2,3]triazol-4-yl]-2-(6-pyrrolidin-1-yl-pyridin-3-yl)-acetamide;
N-[2-(4-Fluoro-benzyl)-2H-[1,2,3]triazol-4-yl]-2-(1-methyl-1H-indazol-5-yl)-acetamide;
N-[2-(4-Methoxy-benzyl)-2H-[1,2,3]triazol-4-yl]-2-(1-methyl-1H-indol-5-yl)-acetamide;
2-(6-Diethylamino-pyridin-3-yl)-N-[2-(4-methoxy-benzyl)-2H-[1,2,3]triazol-4-yl]-acetamide;
2-[6-(3,3-Difluoro-pyrrolidin-1-yl)-pyridin-3-yl]-N-[2-(4-methoxy-benzyl)-2H-[1,2,3]triazol-4-yl]-acetamide;
N-[2-(4-Methoxy-benzyl)-2H-[1,2,3]triazol-4-yl]-2-[4-(3-methyl-oxetan-3-yl)-phenyl]-acetamide;
2-(4-tert-Butyl-phenyl)-N-[2-(4-methoxy-benzyl)-2H-[1,2,3]triazol-4-yl]-acetamide;
N-[2-(4-Methoxy-benzyl)-2H-[1,2,3]triazol-4-yl]-2-(6-pyrrolidin-1-yl-pyridin-3-yl)-acetamide;
N-[2-(4-Methoxy-benzyl)-2H-[1,2,3]triazol-4-yl]-2-(1-methyl-1H-indazol-5-yl)-acetamide;
N-[2-(4-Methyl-benzyl)-2H-[1,2,3]triazol-4-yl]-2-(1-methyl-1H-indol-5-yl)-acetamide;
2-[6-(3,3-Difluoro-pyrrolidin-1-yl)-pyridin-3-yl]-N-[2-(4-methyl-benzyl)-2H-[1,2,3]triazol-4-yl]-acetamide;
2-(4-tert-Butyl-phenyl)-N-[2-(4-methyl-benzyl)-2H-[1,2,3]triazol-4-yl]-acetamide;
N-[2-(4-Methyl-benzyl)-2H-[1,2,3]triazol-4-yl]-2-[4-(3-methyl-oxetan-3-yl)-phenyl]-acetamide;
N-[2-(4-Methyl-benzyl)-2H-[1,2,3]triazol-4-yl]-2-(6-pyrrolidin-1-yl-pyridin-3-yl)-acetamide;
N-[2-(4-Methyl-benzyl)-2H-[1,2,3]triazol-4-yl]-2-(1-methyl-1H-indazol-5-yl)-acetamide;
N-[2-(4-Cyano-3-fluoro-benzyl)-2H-[1,2,3]triazol-4-yl]-2-(1-methyl-1H-indol-5-yl)-acetamide;
N-[2-(4-Cyano-3-fluoro-benzyl)-2H-[1,2,3]triazol-4-yl]-2-[6-(3,3-difluoro-pyrrolidin-1-yl)-pyridin-3-yl]-acetamide;
N-[2-(4-Cyano-3-fluoro-benzyl)-2H-[1,2,3]triazol-4-yl]-2-[4-(3-methyl-oxetan-3-yl)-phenyl]-acetamide;
2-(4-tert-Butyl-phenyl)-N-[2-(4-cyano-3-fluoro-benzyl)-2H-[1,2,3]triazol-4-yl]-acetamide;
N-[2-(4-Cyano-3-fluoro-benzyl)-2H-[1,2,3]triazol-4-yl]-2-(4-isopropyl-phenyl)-acetamide;
N-[2-(4-Cyano-3-fluoro-benzyl)-2H-[1,2,3]triazol-4-yl]-2-(6-pyrrolidin-1-yl-pyridin-3-yl)-acetamide;
N-[2-(4-Cyano-3-fluoro-benzyl)-2H-[1,2,3]triazol-4-yl]-2-(1-methyl-1H-indazol-5-yl)-acetamide;
N-[2-(3,5-Difluoro-4-methoxy-benzyl)-2H-[1,2,3]triazol-4-yl]-2-(1-methyl-1H-indol-5-yl)-acetamide;
N-[2-(3,5-Difluoro-4-methoxy-benzyl)-2H-[1,2,3]triazol-4-yl]-2-[4-(3-methyl-oxetan-3-yl)-phenyl]-acetamide;
2-(4-tert-Butyl-phenyl)-N-[2-(3,5-difluoro-4-methoxy-benzyl)-2H-[1,2,3]triazol-4-yl]-acetamide;
N-[2-(3,5-Difluoro-4-methoxy-benzyl)-2H-[1,2,3]triazol-4-yl]-2-(4-isopropyl-phenyl)-acetamide;
N-[2-(3,5-Difluoro-4-methoxy-benzyl)-2H-[1,2,3]triazol-4-yl]-2-(6-pyrrolidin-1-yl-pyridin-3-yl)-acetamide;
N-[2-(3,5-Difluoro-4-methoxy-benzyl)-2H-[1,2,3]triazol-4-yl]-2-(1-methyl-1H-indazol-5-yl)-acetamide;
2-(4-tert-Butyl-phenyl)-N-{2-[4-(2-methoxy-ethoxy)-benzyl]-2H-[1,2,3]triazol-4-yl}-acetamide;
N-{2-[4-(2-Methoxy-ethoxy)-benzyl]-2H-[1,2,3]triazol-4-yl}-2-(1-methyl-1H-indol-5-yl)-acetamide;
2-(4-tert-Butyl-phenyl)-N-[2-(4-difluoromethoxy-benzyl)-2H-[1,2,3]triazol-4-yl]-acetamide;
N-[2-(4-Difluoromethoxy-benzyl)-2H-[1,2,3]triazol-4-yl]-2-(1-methyl-1H-indol-5-yl)-acetamide;
2-(4-tert-Butyl-phenyl)-N-[2-(4-trifluoromethoxy-benzyl)-2H-[1,2,3]triazol-4-yl]-acetamide;
2-(1-Methyl-1H-indol-5-yl)-N-[2-(4-trifluoromethoxy-benzyl)-2H-[1,2,3]triazol-4-yl]-acetamide;
2-(1-Methyl-1H-indazol-5-yl)-N-[2-(4-trifluoromethoxy-benzyl)-2H-[1,2,3]triazol-4-yl]-acetamide;
2-[4-(3-Methyl-oxetan-3-yl)-phenyl]-N-[2-(4-trifluoromethoxy-benzyl)-2H-[1,2,3]triazol-4-yl]-acetamide;
2-[6-(3,3-Difluoro-pyrrolidin-1-yl)-pyridin-3-yl]-N-[2-(4-fluoro-benzyl)-2H-[1,2,3]triazol-4-yl]-acetamide;
2-(6-Diethylamino-pyridin-3-yl)-N-[2-(4-fluoro-benzyl)-2H-[1,2,3]triazol-4-yl]-acetamide;
2-(4-tert-Butyl-phenyl)-N-[2-(4-cyano-benzyl)-2H-[1,2,3]triazol-4-yl]-acetamide;
N-[2-(4-Cyano-benzyl)-2H-[1,2,3]triazol-4-yl]-2-[6-(3,3-difluoro-pyrrolidin-1-yl)-pyridin-3-yl]-acetamide;
N-[2-(4-Cyano-benzyl)-2H-[1,2,3]triazol-4-yl]-2-(6-pyrrolidin-1-yl-pyridin-3-yl)-acetamide;
N-[2-(4-Cyano-benzyl)-2H-[1,2,3]triazol-4-yl]-2-(1-methyl-1H-indol-5-yl)-acetamide;
N-[2-(4-Cyano-benzyl)-2H-[1,2,3]triazol-4-yl]-2-(1,3-dimethyl-1H-indol-5-yl)-acetamide;
N-[2-(4-Cyano-benzyl)-2H-[1,2,3]triazol-4-yl]-2-(1-methyl-1H-indazol-6-yl)-acetamide;
N-[2-(4-Cyano-benzyl)-2H-[1,2,3]triazol-4-yl]-2-(1,3-dimethyl-1H-indazol-5-yl)-acetamide;
N-[2-(4-Cyano-benzyl)-2H-[1,2,3]triazol-4-yl]-2-(1-ethyl-1H-indazol-5-yl)-acetamide;
N-[2-(4-Cyano-benzyl)-2H-[1,2,3]triazol-4-yl]-2-(1-propyl-1H-indazol-5-yl)-acetamide;
N-[2-(4-Cyano-3-fluoro-benzyl)-2H-[1,2,3]triazol-4-yl]-2-(1,3-dimethyl-1H-indol-6-yl)-acetamide;
N-[2-(4-Cyano-benzyl)-2H-[1,2,3]triazol-4-yl]-2-(1,3-dimethyl-1H-indol-6-yl)-acetamide;
N-[2-(4-Fluoro-3-methoxy-benzyl)-2H-[1,2,3]triazol-4-yl]-2-[4-(oxetan-3-ylmethoxy)-phenyl]-acetamide;
N-[2-(4-Fluoro-3-methoxy-benzyl)-2H-[1,2,3]triazol-4-yl]-2-(1-methyl-1H-indazol-6-yl)-acetamide;
N-[2-(4-Fluoro-3-methoxy-benzyl)-2H-[1,2,3]triazol-4-yl]-2-[4-(3-methoxy-oxetan-3-yl)-phenyl]-acetamide;
2-[4-(3,3-Difluoro-cyclobutylmethoxy)-phenyl]-N-[2-(4-fluoro-3-methoxy-benzyl)-2H-[1,2,3]triazol-4-yl]-acetamide;
N-[2-(4-Fluoro-3-methoxy-benzyl)-2H-[1,2,3]triazol-4-yl]-2-[4-(3-methyl-oxetan-3-ylmethoxy)-phenyl]-acetamide;
N-[2-(4-Fluoro-3-methoxy-benzyl)-2H-[1,2,3]triazol-4-yl]-2-[4-(1-trifluoromethyl-cyclopropyl)-phenyl]-acetamide;
2-[4-(3,3-Difluoro-cyclobutoxy)-phenyl]-N-[2-(4-fluoro-3-methoxy-benzyl)-2H-[1,2,3]triazol-4-yl]-acetamide;
2-[6-(3,3-Difluoro-pyrrolidin-1-yl)-pyridin-3-yl]-N-[2-(4-fluoro-3-methoxy-benzyl)-2H-[1,2,3]triazol-4-yl]-acetamide;
N-[2-(4-Fluoro-3-methoxy-benzyl)-2H-[1,2,3]triazol-4-yl]-2-[4-(3-fluoro-oxetan-3-yl)-phenyl]-acetamide;
2-(1-Ethyl-1H-indazol-5-yl)-N-[2-(4-fluoro-3-methoxy-benzyl)-2H-[1,2,3]triazol-4-yl]-acetamide;
2-(1,3-Dimethyl-1H-indol-5-yl)-N-[2-(4-fluoro-3-methoxy-benzyl)-2H-[1,2,3]triazol-4-yl]-acetamide;
2-(4-tert-Butyl-phenyl)-N-[2-(4-fluoro-3-methoxy-benzyl)-2H-[1,2,3]triazol-4-yl]-acetamide;

N-[2-(3-Fluoro-4-methoxy-benzyl)-2H-[1,2,3]triazol-4-yl]-2-[4-(oxetan-3-ylmethoxy)-phenyl]-acetamide;
N-[2-(3-Fluoro-4-methoxy-benzyl)-2H-[1,2,3]triazol-4-yl]-2-(1-methyl-1H-indazol-6-yl)-acetamide;
N-[2-(3-Fluoro-4-methoxy-benzyl)-2H-[1,2,3]triazol-4-yl]-2-[4-(3-methoxy-oxetan-3-yl)-phenyl]-acetamide;
N-[2-(3-Fluoro-4-methoxy-benzyl)-2H-[1,2,3]triazol-4-yl]-2-[4-(3-methyl-oxetan-3-ylmethoxy)-phenyl]-acetamide;
N-[2-(3-Fluoro-4-methoxy-benzyl)-2H-[1,2,3]triazol-4-yl]-2-[4-(1-trifluoromethyl-cyclopropyl)-phenyl]-acetamide;
2-[4-(3,3-Difluoro-cyclobutoxy)-phenyl]-N-[2-(3-fluoro-4-methoxy-benzyl)-2H-[1,2,3]triazol-4-yl]-acetamide;
2-[6-(3,3-Difluoro-pyrrolidin-1-yl)-pyridin-3-yl]-N-[2-(3-fluoro-4-methoxy-benzyl)-2H-[1,2,3]triazol-4-yl]-acetamide;
N-[2-(3-Fluoro-4-methoxy-benzyl)-2H-[1,2,3]triazol-4-yl]-2-[4-(3-fluoro-oxetan-3-yl)-phenyl]-acetamide;
2-(1-Ethyl-1H-indazol-5-yl)-N-[2-(3-fluoro-4-methoxy-benzyl)-2H-[1,2,3]triazol-4-yl]-acetamide;
2-(1,3-Dimethyl-1H-indol-5-yl)-N-[2-(3-fluoro-4-methoxy-benzyl)-2H-[1,2,3]triazol-4-yl]-acetamide;
2-(4-tert-Butyl-phenyl)-N-[2-(3-fluoro-4-methoxy-benzyl)-2H-[1,2,3]triazol-4-yl]-acetamide;
N-[2-(4-Cyano-3-fluoro-benzyl)-2H-[1,2,3]triazol-4-yl]-2-[4-(oxetan-3-ylmethoxy)-phenyl]-acetamide;
N-[2-(4-Cyano-3-fluoro-benzyl)-2H-[1,2,3]triazol-4-yl]-2-(1-methyl-1H-indazol-6-yl)-acetamide;
N-[2-(4-Cyano-3-fluoro-benzyl)-2H-[1,2,3]triazol-4-yl]-2-[4-(3-methoxy-oxetan-3-yl)-phenyl]-acetamide;
N-[2-(4-Cyano-3-fluoro-benzyl)-2H-[1,2,3]triazol-4-yl]-2-[4-(3,3-difluoro-cyclobutylmethoxy)-phenyl]-acetamide;
N-[2-(4-Cyano-3-fluoro-benzyl)-2H-[1,2,3]triazol-4-yl]-2-[4-(3-methyl-oxetan-3-ylmethoxy)-phenyl]-acetamide;
N-[2-(4-Cyano-3-fluoro-benzyl)-2H-[1,2,3]triazol-4-yl]-2-[4-(1-trifluoromethyl-cyclopropyl)-phenyl]-acetamide;
N-[2-(4-Cyano-3-fluoro-benzyl)-2H-[1,2,3]triazol-4-yl]-2-[4-(3,3-difluoro-cyclobutoxy)-phenyl]-acetamide;
N-[2-(4-Cyano-3-fluoro-benzyl)-2H-[1,2,3]triazol-4-yl]-2-[4-(3-fluoro-oxetan-3-yl)-phenyl]-acetamide;
N-[2-(4-Cyano-3-fluoro-benzyl)-2H-[1,2,3]triazol-4-yl]-2-(1-ethyl-1H-indazol-5-yl)-acetamide;
N-[2-(4-Cyano-3-fluoro-benzyl)-2H-[1,2,3]triazol-4-yl]-2-(1,3-dimethyl-1H-indol-5-yl)-acetamide;
N-[2-(3,5-Difluoro-4-methoxy-benzyl)-2H-[1,2,3]triazol-4-yl]-2-[4-(oxetan-3-ylmethoxy)-phenyl]-acetamide;
N-[2-(3,5-Difluoro-4-methoxy-benzyl)-2H-[1,2,3]triazol-4-yl]-2-(1-methyl-1H-indazol-6-yl)-acetamide;
N-[2-(3,5-Difluoro-4-methoxy-benzyl)-2H-[1,2,3]triazol-4-yl]-2-[4-(3-methoxy-oxetan-3-yl)-phenyl]-acetamide;
N-[2-(3,5-Difluoro-4-methoxy-benzyl)-2H-[1,2,3]triazol-4-yl]-2-[4-(3-methyl-oxetan-3-ylmethoxy)-phenyl]-acetamide;
N-[2-(3,5-Difluoro-4-methoxy-benzyl)-2H-[1,2,3]triazol-4-yl]-2-[4-(1-trifluoromethyl-cyclopropyl)-phenyl]-acetamide;
2-[4-(3,3-Difluoro-cyclobutoxy)-phenyl]-N-[2-(3,5-difluoro-4-methoxy-benzyl)-2H-[1,2,3]triazol-4-yl]-acetamide;
N-[2-(3,5-Difluoro-4-methoxy-benzyl)-2H-[1,2,3]triazol-4-yl]-2-[6-(3,3-difluoro-pyrrolidin-1-yl)-pyridin-3-yl]-acetamide;
N-[2-(3,5-Difluoro-4-methoxy-benzyl)-2H-[1,2,3]triazol-4-yl]-2-[4-(3-fluoro-oxetan-3-yl)-phenyl]-acetamide;
N-[2-(3,5-Difluoro-4-methoxy-benzyl)-2H-[1,2,3]triazol-4-yl]-2-(1-ethyl-1H-indazol-5-yl)-acetamide;
N-[2-(3,5-Difluoro-4-methoxy-benzyl)-2H-[1,2,3]triazol-4-yl]-2-(1,3-dimethyl-1H-indol-5-yl)-acetamide;
N-[2-(4-Fluoro-3-methoxy-benzyl)-2H-[1,2,3]triazol-4-yl]-2-(1-methyl-1H-indazol-5-yl)-acetamide;
N-[2-(3-Fluoro-4-methoxy-benzyl)-2H-[1,2,3]triazol-4-yl]-2-(1-methyl-1H-indazol-5-yl)-acetamide;
N-[2-(4-Fluoro-3-methoxy-benzyl)-2H-[1,2,3]triazol-4-yl]-2-(4-isopropyl-phenyl)-acetamide;
N-[2-(3-Fluoro-4-methoxy-benzyl)-2H-[1,2,3]triazol-4-yl]-2-(4-isopropyl-phenyl)-acetamide;
N-[2-(4-Fluoro-3-methoxy-benzyl)-2H-[1,2,3]triazol-4-yl]-2-(6-pyrrolidin-1-yl-pyridin-3-yl)-acetamide;
N-[2-(3-Fluoro-4-methoxy-benzyl)-2H-[1,2,3]triazol-4-yl]-2-(6-pyrrolidin-1-yl-pyridin-3-yl)-acetamide;
2-[4-(Cyano-dimethyl-methyl)-phenyl]-N-[2-(4-cyano-3-fluoro-benzyl)-2H-[1,2,3]triazol-4-yl]-acetamide;
2-(4-tert-Butyl-phenyl)-N-[2-(4-cyano-3-fluoro-5-methoxy-benzyl)-2H-[1,2,3]triazol-4-yl]-acetamide;
N-[2-(4-Cyano-3-fluoro-benzyl)-2H-[1,2,3]triazol-4-yl]-2-(4-trifluoromethyl-phenyl)-acetamide;
N-[2-(4-Cyano-3-fluoro-benzyl)-2H-[1,2,3]triazol-4-yl]-2-(5-fluoro-6-pyrrolidin-1-yl-pyridin-3-yl)-acetamide;
2-(4-tert-Butyl-phenyl)-N-[2-(4-cyano-3-methyl-benzyl)-2H-[1,2,3]triazol-4-yl]-acetamide;
N-[2-(4-Cyano-3-methyl-benzyl)-2H-[1,2,3]triazol-4-yl]-2-(1-methyl-1H-indazol-6-yl)-acetamide;
N-[2-(4-Cyano-3-methyl-benzyl)-2H-[1,2,3]triazol-4-yl]-2-(1-methyl-1H-indazol-5-yl)-acetamide;
N-[2-(4-Cyano-3-methyl-benzyl)-2H-[1,2,3]triazol-4-yl]-2-(4-isopropyl-phenyl)-acetamide;
N-[2-(4-Cyano-3-methyl-benzyl)-2H-[1,2,3]triazol-4-yl]-2-[4-(3,3-difluoro-cyclobutoxy)-phenyl]-acetamide;
N-[2-(4-Cyano-3-methyl-benzyl)-2H-[1,2,3]triazol-4-yl]-2-[6-(3,3-difluoro-pyrrolidin-1-yl)-pyridin-3-yl]-acetamide;
N-[2-(4-Cyano-3-methyl-benzyl)-2H-[1,2,3]triazol-4-yl]-2-(1-ethyl-1H-indazol-5-yl)-acetamide;
N-[2-(4-Cyano-3-methyl-benzyl)-2H-[1,2,3]triazol-4-yl]-2-(1,3-dimethyl-1H-indazol-5-yl)-acetamide;
N-[2-(4-Cyano-3-methyl-benzyl)-2H-[1,2,3]triazol-4-yl]-2-(6-pyrrolidin-1-yl-pyridin-3-yl)-acetamide;
N-[2-(4-Cyano-3-methyl-benzyl)-2H-[1,2,3]triazol-4-yl]-2-(1,3-dimethyl-1H-indol-5-yl)-acetamide;
2-(4-tert-Butyl-phenyl)-N-[2-(3-cyano-4-fluoro-benzyl)-2H-[1,2,3]triazol-4-yl]-acetamide;
N-[2-(3-Cyano-4-fluoro-benzyl)-2H-[1,2,3]triazol-4-yl]-2-(1-methyl-1H-indazol-5-yl)-acetamide;
N-[2-(3-Cyano-4-fluoro-benzyl)-2H-[1,2,3]triazol-4-yl]-2-(4-isopropyl-phenyl)-acetamide;
N-[2-(4-Cyano-3-fluoro-benzyl)-2H-[1,2,3]triazol-4-yl]-2-[4-(3-fluoro-oxetan-3-ylmethoxy)-phenyl]-acetamide;
N-[2-(4-Cyano-3-fluoro-benzyl)-2H-[1,2,3]triazol-4-yl]-2-[4-(3,3-difluoro-1-methyl-cyclobutylmethoxy)-phenyl]-acetamide;
N-[2-(4-Cyano-3-fluoro-benzyl)-2H-[1,2,3]triazol-4-yl]-2-(1,3-dimethyl-1H-indazol-5-yl)-acetamide;
2-(4-tert-Butyl-phenyl)-N-[2-(4-difluoromethoxy-3-fluoro-benzyl)-2H-[1,2,3]triazol-4-yl]-acetamide;
N-[2-(4-Difluoromethoxy-3-fluoro-benzyl)-2H-[1,2,3]triazol-4-yl]-2-(1-methyl-1H-indazol-5-yl)-acetamide;
N-[2-(4-Difluoromethoxy-3-fluoro-benzyl)-2H-[1,2,3]triazol-4-yl]-2-(4-isopropyl-phenyl)-acetamide;
N-[2-(4-Difluoromethoxy-3-fluoro-benzyl)-2H-[1,2,3]triazol-4-yl]-2-[4-(1-trifluoromethyl-cyclopropyl)-phenyl]-acetamide;
N-[2-(4-Difluoromethoxy-3-fluoro-benzyl)-2H-[1,2,3]triazol-4-yl]-2-[6-(3,3-difluoro-pyrrolidin-1-yl)-pyridin-3-yl]-acetamide;

N-[2-(4-Difluoromethoxy-3-fluoro-benzyl)-2H-[1,2,3]tri-azol-4-yl]-2-(6-pyrrolidin-1-yl-pyridin-3-yl)-acetamide;
2-(4-tert-Butyl-phenyl)-N-[2-(3-fluoro-4-trifluoromethoxy-benzyl)-2H-[1,2,3]triazol-4-yl]-acetamide;
N-[2-(3-Fluoro-4-trifluoromethoxy-benzyl)-2H-[1,2,3]tri-azol-4-yl]-2-(1-methyl-1H-indazol-6-yl)-acetamide;
N-[2-(3-Fluoro-4-trifluoromethoxy-benzyl)-2H-[1,2,3]tri-azol-4-yl]-2-(1-methyl-1H-indazol-5-yl)-acetamide;
N-[2-(3-Fluoro-4-trifluoromethoxy-benzyl)-2H-[1,2,3]tri-azol-4-yl]-2-(4-isopropyl-phenyl)-acetamide;
N-[2-(3-Fluoro-4-trifluoromethoxy-benzyl)-2H-[1,2,3]tri-azol-4-yl]-2-[4-(1-trifluoromethyl-cyclopropyl)-phenyl]-acetamide;
2-[6-(3,3-Difluoro-pyrrolidin-1-yl)-pyridin-3-yl]-N-[2-(3-fluoro-4-trifluoromethoxy-benzyl)-2H-[1,2,3]triazol-4-yl]-acetamide;
2-(1-Ethyl-1H-indazol-5-yl)-N-[2-(3-fluoro-4-trifluoromethoxy-benzyl)-2H-[1,2,3]triazol-4-yl]-acetamide;
2-(1,3-Dimethyl-1H-indazol-5-yl)-N-[2-(3-fluoro-4-trifluoromethoxy-benzyl)-2H-[1,2,3]triazol-4-yl]-acetamide;
N-[2-(3-Fluoro-4-trifluoromethoxy-benzyl)-2H-[1,2,3]tri-azol-4-yl]-2-(6-pyrrolidin-1-yl-pyridin-3-yl)-acetamide;
N-[2-(4-Cyano-benzyl)-2H-[1,2,3]triazol-4-yl]-2-[4-(3-methyl-oxetan-3-ylmethoxy)-phenyl]-acetamide;
N-[2-(4-Cyano-benzyl)-2H-[1,2,3]triazol-4-yl]-2-[4-(3-fluoro-oxetan-3-ylmethoxy)-phenyl]-acetamide;
N-[2-(4-Cyano-benzyl)-2H-[1,2,3]triazol-4-yl]-2-[4-(1-trifluoromethyl-cyclopropyl)-phenyl]-acetamide;
N-[2-(4-Cyano-benzyl)-2H-[1,2,3]triazol-4-yl]-2-[4-(3,3-difluoro-cyclobutoxy)-phenyl]-acetamide;
N-[2-(4-Cyano-benzyl)-2H-[1,2,3]triazol-4-yl]-2-[4-(3,3-difluoro-1-methyl-cyclobutylmethoxy)-phenyl]-acetamide;
N-[2-(4-Cyano-benzyl)-2H-[1,2,3]triazol-4-yl]-2-[4-(3-fluoro-oxetan-3-yl)-phenyl]-acetamide;
N-[2-(4-Cyano-3-fluoro-benzyl)-2H-[1,2,3]triazol-4-yl]-2-[3-methyl-4-(2,2,2-trifluoro-ethoxy)-phenyl]-acetamide;
N-[2-(3-Cyano-4-methyl-benzyl)-2H-[1,2,3]triazol-4-yl]-2-[4-(3-fluoro-oxetan-3-ylmethoxy)-phenyl]-acetamide;
N-[2-(3-Cyano-4-methyl-benzyl)-2H-[1,2,3]triazol-4-yl]-2-[4-(3-fluoro-oxetan-3-yl)-phenyl]-acetamide;
2-(4-tert-Butyl-phenyl)-N-[2-(3-cyano-4-methoxy-benzyl)-2H-[1,2,3]triazol-4-yl]-acetamide;
N-[2-(3-Cyano-4-methoxy-benzyl)-2H-[1,2,3]triazol-4-yl]-2-[4-(1-trifluoromethyl-cyclopropyl)-phenyl]-acetamide;
N-[2-(3-Cyano-4-methoxy-benzyl)-2H-[1,2,3]triazol-4-yl]-2-(1-methyl-1H-indazol-5-yl)-acetamide;
N-[2-(3-Cyano-4-methoxy-benzyl)-2H-[1,2,3]triazol-4-yl]-2-(4-isopropyl-phenyl)-acetamide;
N-[2-(3-Cyano-4-methyl-benzyl)-2H-[1,2,3]triazol-4-yl]-2-[4-(3-methoxy-oxetan-3-yl)-phenyl]-acetamide;
N-[2-(3-Cyano-4-methoxy-benzyl)-2H-[1,2,3]triazol-4-yl]-2-[6-(3,3-difluoro-pyrrolidin-1-yl)-pyridin-3-yl]-acetamide;
N-[2-(3-Cyano-4-methoxy-benzyl)-2H-[1,2,3]triazol-4-yl]-2-(1-methyl-1H-indazol-5-yl)-acetamide;
N-[2-(3-Cyano-4-methyl-benzyl)-2H-[1,2,3]triazol-4-yl]-2-[4-(3,3-difluoro-cyclobutoxy)-phenyl]-acetamide;
N-[2-(3,4-Difluoro-5-methoxy-benzyl)-2H-[1,2,3]triazol-4-yl]-2-(1,3-dimethyl-1H-indazol-5-yl)-acetamide;
N-[2-(3-Cyano-4-methyl-benzyl)-2H-[1,2,3]triazol-4-yl]-2-[6-(3,3-difluoro-pyrrolidin-1-yl)-pyridin-3-yl]-acetamide;
N-[2-(3,4-Difluoro-5-methoxy-benzyl)-2H-[1,2,3]triazol-4-yl]-2-(1-methyl-1H-indazol-5-yl)-acetamide;
N-[2-(3-Cyano-4-methyl-benzyl)-2H-[1,2,3]triazol-4-yl]-2-(6-pyrrolidin-1-yl-pyridin-3-yl)-acetamide;
N-[2-(3-Cyano-4-methoxy-benzyl)-2H-[1,2,3]triazol-4-yl]-2-[4-(3-fluoro-oxetan-3-yl)-phenyl]-acetamide;
N-[2-(3-Cyano-4-methyl-benzyl)-2H-[1,2,3]triazol-4-yl]-2-(1-methyl-1H-indazol-6-yl)-acetamide;
N-[2-(3-Cyano-4-methyl-benzyl)-2H-[1,2,3]triazol-4-yl]-2-(4-isopropyl-phenyl)-acetamide;
2-(4-tert-Butyl-phenyl)-N-[2-(3-cyano-4-methyl-benzyl)-2H-[1,2,3]triazol-4-yl]-acetamide;
2-(4-tert-Butyl-phenyl)-N-[2-(3,4-difluoro-5-methoxy-benzyl)-2H-[1,2,3]triazol-4-yl]-acetamide;
N-[2-(3,4-Difluoro-5-methoxy-benzyl)-2H-[1,2,3]triazol-4-yl]-2-[6-(3,3-difluoro-pyrrolidin-1-yl)-pyridin-3-yl]-acetamide;
N-[2-(3,4-Difluoro-5-methoxy-benzyl)-2H-[1,2,3]triazol-4-yl]-2-(1-ethyl-1H-indazol-5-yl)-acetamide;
N-[2-(3,4-Difluoro-5-methoxy-benzyl)-2H-[1,2,3]triazol-4-yl]-2-(6-pyrrolidin-1-yl-pyridin-3-yl)-acetamide;
N-[2-(3,4-Difluoro-5-methoxy-benzyl)-2H-[1,2,3]triazol-4-yl]-2-(4-isopropyl-phenyl)-acetamide;
N-[2-(3-Cyano-4-methoxy-benzyl)-2H-[1,2,3]triazol-4-yl]-2-[4-(3,3-difluoro-cyclobutoxy)-phenyl]-acetamide;
N-[2-(3,4-Difluoro-5-methoxy-benzyl)-2H-[1,2,3]triazol-4-yl]-2-[4-(3-fluoro-oxetan-3-yl)-phenyl]-acetamide;
N-[2-(3,4-Difluoro-5-methoxy-benzyl)-2H-[1,2,3]triazol-4-yl]-2-(1-methyl-1H-indazol-6-yl)-acetamide;
N-[2-(3-Cyano-4-methyl-benzyl)-2H-[1,2,3]triazol-4-yl]-2-[4-(1-trifluoromethyl-cyclopropyl)-phenyl]-acetamide;
N-[2-(3,4-Difluoro-5-methoxy-benzyl)-2H-[1,2,3]triazol-4-yl]-2-[4-(1-trifluoromethyl-cyclopropyl)-phenyl]-acetamide;
N-[2-(3,4-Difluoro-5-methoxy-benzyl)-2H-[1,2,3]triazol-4-yl]-2-[4-(3-methoxy-oxetan-3-yl)-phenyl]-acetamide;
N-[2-(3,4-Difluoro-5-methoxy-benzyl)-2H-[1,2,3]triazol-4-yl]-2-[4-(3-fluoro-oxetan-3-ylmethoxy)-phenyl]-acetamide;
2-[4-(3,3-Difluoro-cyclobutoxy)-phenyl]-N-[2-(3,4-difluoro-5-methoxy-benzyl)-2H-[1,2,3]triazol-4-yl]-acetamide;
2-[4-(1-Cyano-cyclopropyl)-phenyl]-N-[2-(4-cyano-3-fluoro-benzyl)-2H-[1,2,3]triazol-4-yl]-acetamide;
N-(2-(4-cyano-3-fluorobenzyl)-2H-1,2,3-triazol-4-yl)-2-(4-(pentafluorosulfanyl)phenyl)acetamide;
N-[2-(4-Cyano-3-methoxy-benzyl)-2H-[1,2,3]triazol-4-yl]-2-[4-(1-trifluoromethyl-cyclopropyl)-phenyl]-acetamide;
N-[2-(4-Cyano-benzyl)-2H-[1,2,3]triazol-4-yl]-2-(1-methyl-1H-indazol-5-yl)-acetamide;
N-[2-(4-Cyano-3-methyl-benzyl)-2H-[1,2,3]triazol-4-yl]-2-[4-(3-fluoro-oxetan-3-yl)-phenyl]-acetamide;
N-[2-(3-Cyano-4-methoxy-benzyl)-2H-[1,2,3]triazol-4-yl]-2-(6-pyrrolidin-1-yl-pyridin-3-yl)-acetamide;
N-[2-(4-Cyano-benzyl)-2H-[1,2,3]triazol-4-yl]-2-[4-(3-methoxy-oxetan-3-yl)-phenyl]-acetamide;
N-[2-(4-Cyano-benzyl)-2H-[1,2,3]triazol-4-yl]-2-[4-(3,3-difluoro-cyclobutylmethoxy)-phenyl]-acetamide;
2-(4-tert-Butyl-phenyl)-N-[2-(4-cyano-3-methoxy-benzyl)-2H-[1,2,3]triazol-4-yl]-acetamide;
N-[2-(3,4-Difluoro-5-methoxy-benzyl)-2H-[1,2,3]triazol-4-yl]-2-(1,3-dimethyl-1H-indol-5-yl)-acetamide;
N-[2-(4-Cyano-3-methyl-benzyl)-2H-[1,2,3]triazol-4-yl]-2-[4-(1-trifluoromethyl-cyclopropyl)-phenyl]-acetamide;
N-[2-(5-Cyano-pyridin-2-ylmethyl)-2H-[1,2,3]triazol-4-yl]-2-[3-methyl-4-(2,2,2-trifluoro-ethoxy)-phenyl]-acetamide;
N-[2-(5-Cyano-pyridin-2-ylmethyl)-2H-[1,2,3]triazol-4-yl]-2-(1,3-dimethyl-1H-indol-5-yl)-acetamide;
2-(4-tert-Butyl-phenyl)-N-[2-(5-cyano-pyridin-2-ylmethyl)-2H-[1,2,3]triazol-4-yl]-acetamide;

N-[2-(5-Cyano-pyridin-2-ylmethyl)-2H-[1,2,3]triazol-4-yl]-2-[4-(1-trifluoromethyl-cyclopropyl)-phenyl]-acetamide;
N-[2-(5-Cyano-pyridin-2-ylmethyl)-2H-[1,2,3]triazol-4-yl]-2-[4-(3,3-difluoro-cyclobutoxy)-phenyl]-acetamide;
N-[2-(5-Cyano-pyridin-2-ylmethyl)-2H-[1,2,3]triazol-4-yl]-2-(5-fluoro-6-pyrrolidin-1-yl-pyridin-3-yl)-acetamide;
N-[2-(4-Cyano-3-fluoro-benzyl)-2H-[1,2,3]triazol-4-yl]-2-[4-(2,2,2-trifluoro-1,1-dimethyl-ethyl)-phenyl]-acetamide; and
N-[2-(4-Cyano-3-fluoro-benzyl)-2H-[1,2,3]triazol-4-yl]-2-[4-((1 S*2*)-2-trifluoromethyl-cyclopropyl)-phenyl]-acetamide.

The compounds of formula (I) according to embodiments 1) to 19) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 19).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively the term "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) as defined in any one of embodiments 1) to 19) are useful for the prevention or treatment of diseases or disorders where calcium T channels are involved.

Such diseases or disorders where calcium T channels are involved may be defined as including especially:
epilepsy (notably absence epilepsy, childhood absence and other forms of idiopathic generalized epilepsies, temporal lobe epilepsy);
sleep disorders and sleep disturbances;
pain (notably inflammatory pain, neuropathic pain, peripheral pain, chronic pain associated with peripheral axonal injury);
neurological diseases and disorders (notably essential tremors, Parkinson's disease, schizophrenia, depression, anxiety, psychosis, neurodegenerative disorders, autism, drug addiction);
cardiovascular diseases and disorders (notably hypertension, cardiac arrhythmias, atrial fibrillation, congenital heart failure, heart block);
cancer;
diabetes and diabetic neuropathy; and
infertility and sexual dysfunction.

Notably such diseases or disorders where calcium T channels are involved refer to epilepsy, neurological disorders, and pain. Preferably such diseases or disorders refer to epilepsy and pain.

The term "epilepsy" describes recurrent unprovoked seizures wherein the term "seizure" refers to an excessive and/or hypersynchronous electrical neuronal activity. Different types of "epilepsy" are disclosed for example in [Berg et al., Epilepsia. 2010; 51(4): 676-685], which reference is herewith incorporated by reference. The term "epilepsy" as used herein preferably refers to absence epilepsy, childhood absence and other forms of idiopathic generalized epilepsies, temporal lobe epilepsy.

The term "pain" preferably refers to inflammatory pain, neuropathic pain, peripheral pain, and chronic pain associated with peripheral axonal injury.

The term "neurological diseases and disorders" preferably refers to essential tremors, Parkinson's disease, schizophrenia, depression, anxiety, psychosis, neurodegenerative disorders, autism, drug addiction.

The term "cardiovascular diseases and disorders" preferably refers to hypertension, cardiac arrhythmias, atrial fibrillation, congenital heart failure, heart block.

The compounds of formula (I) as defined in embodiments 1) to 19) are also useful in a method of reducing the concentration of calcium in a neuronal cell, and wherein said reduction in calcium is achieved by blocking the calcium T-channel present in such neuronal cell; said method comprising the administration of a compound of formula (I) as defined in embodiments 1) to 19).

The compounds of formula (I) as defined in embodiments 1) to 19) are also useful in a method of decreasing burst firing discharges in a neuronal cell and wherein said decrease of burst firing is achieved by blocking the calcium T-channel; said method comprising the administration of a compound of formula (I) as defined in embodiments 1) to 19).

Preparation of Compounds of Formula (I):

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In the schemes below, the generic groups X, Y, $R^1$, $R^2$, $(R^4)_n$, and $(R^5)_m$ are as defined for the compounds of formula (I). In some instances the generic groups $R^1$, $R^2$, $(R^4)_n$, and $(R^5)_m$ may be incompatible with the assembly illustrated in the schemes and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts in a manner known per se.

Compounds of formula (I) can be prepared via an amide coupling as final step (Scheme 1). Generally, the corresponding carboxylic acid (IV) can be activated to the corresponding acid chloride, typically with oxalyl chloride. Alternatively, the carboxylic acid (IV) can be directly coupled to the amine (III) using a coupling reagent, typically HATU or HBTU. In certain instances two coupling products can be formed and are separated by preparative HPLC.

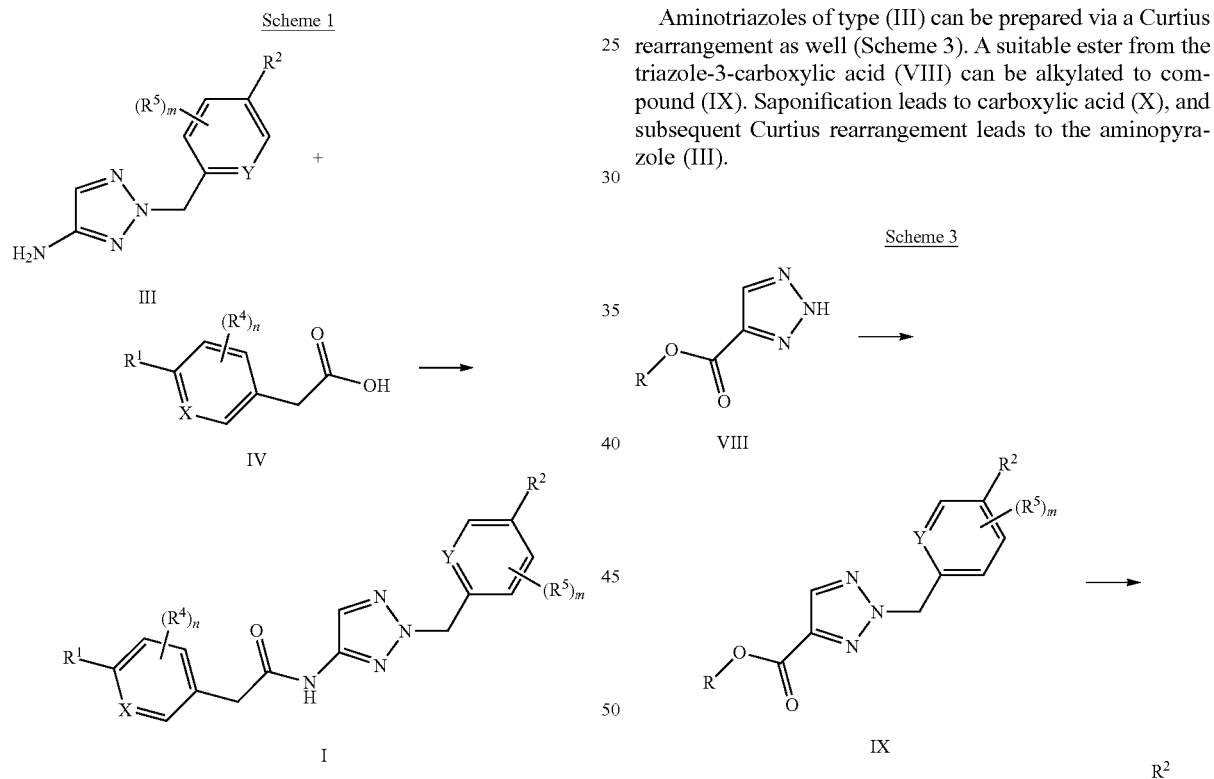

The desired primary aminotriazole (III) can be prepared from the corresponding nitrotriazole (V) through an alkylation (compound of type (VI)) and a reduction step. For the reduction step, zinc or iron are preferentially used.

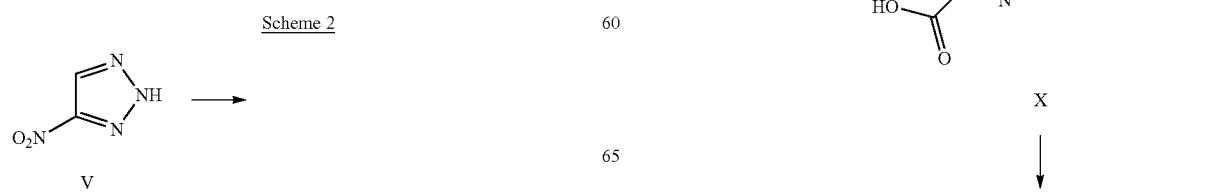

Aminotriazoles of type (III) can be prepared via a Curtius rearrangement as well (Scheme 3). A suitable ester from the triazole-3-carboxylic acid (VIII) can be alkylated to compound (IX). Saponification leads to carboxylic acid (X), and subsequent Curtius rearrangement leads to the aminopyrazole (III).

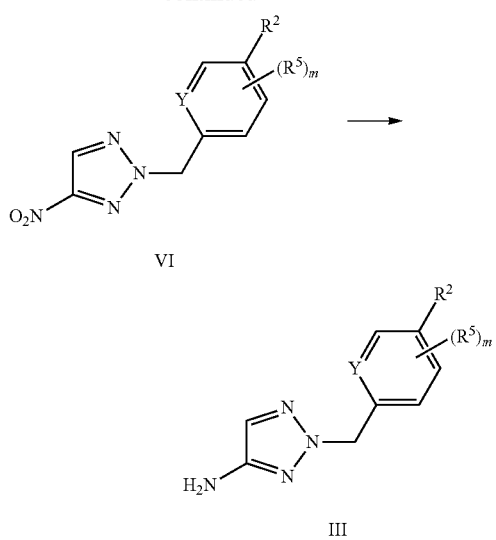

-continued

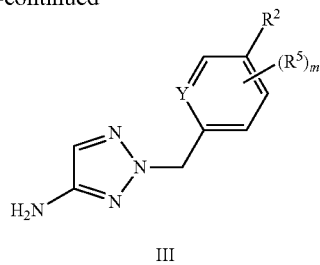

III

The corresponding benzyl chlorides, benzyl bromides, or benzyl mesylates necessary for the alkylation steps described in Schemes 2 (V→VI) and 3 (VIII→IX) can be prepared according to standard literature procedures or as described in the examples here below.

A third possibility to prepare a compound of type III starts from 4,5-dibromo-2H-1,2,3-triazole (Scheme 4). An N-alkylation leads to a compound of type (XI). The selective reduction of a bromide with, for instance, $^i$PrMgCl (P. Wipf et al., Org. Lett. 2010, 12(20), 4632-4635) leads to a compound of type (XII), and an Ullman amination leads to a compound of type (III)

-continued

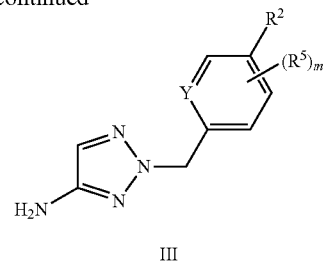

III

The carboxylic acids of type (IV) can be prepared according to known procedures. In particular, a Negishi coupling (Scheme 5), or a similar carbon-carbon coupling between an (hetero)aryl bromide of type (XIII) and (2-(tert-butoxy)-2-oxoethyl)zinc(II) bromide leads to the ester of type (XIV): Hydrolysis, generally under acidic conditions, leads to the acid of type (IV). Bromide of type (XIII) is either commercially available, or can be prepared according to known procedures (see experimental part).

Scheme 4

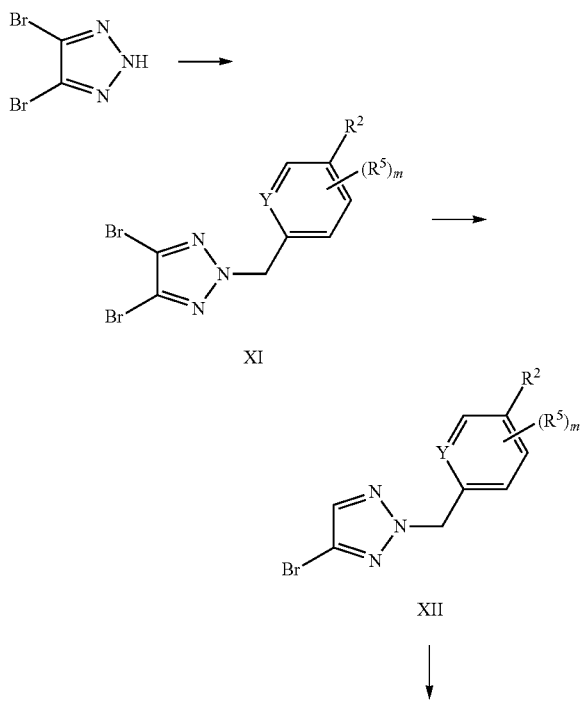

Scheme 5

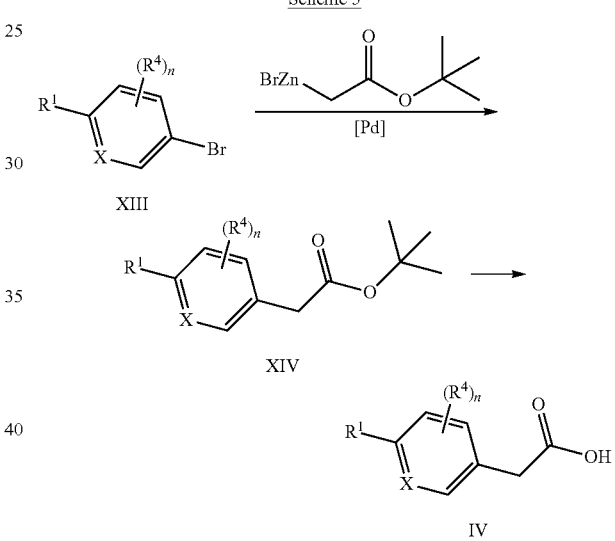

Alternatively, a benzoic acid of type (XV) can be transformed into an acid of type (IV) via a Wolff rearrangement (Scheme 6). The acid of type (XV) can be reduced to an alcohol of type (XVI). This alcohol can then be activated to a compound of type (XVII), wherein LG represents a leaving group such as chloride, bromide, mesylate of tosylate, and homologated to nitrile of type (XVIII): Hydrolysis would then lead to the acid of type (IV).

Scheme 6

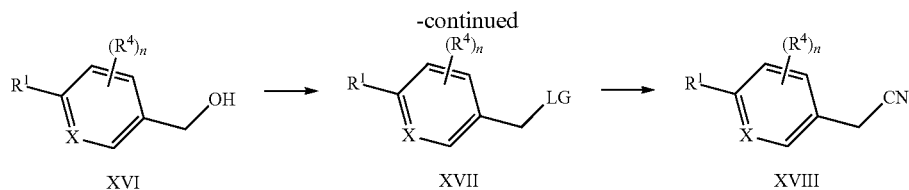

Whenever required, the substituents $R^1$, $R^2$, $R^4$ and/or $R^5$ can be present as precursors in the starting material, and can be transformed by additional routine transformations during the synthetic pathways presented herein.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm), IC (5 µm) or AD-H (5 µm) column. Typical conditions of chiral HPLC are an isocratic mixture of eluent A (EtOH, in presence or absence of an amine such as triethylamine or diethylamine) and eluent B (heptane), at a flow rate of 0.8 to 150 mL/min.

EXPERIMENTAL PART

The following examples illustrate the invention but do not at all limit the scope thereof.

Abbreviations: (as used herein and in the description above)
Ac Acetyl
aq. Aqueous
Bn Benzyl
Bu Butyl
CAS Chemical abstract system
comb. Combined
conc. Concentrated
dba Dibenzylideneacetone
DBU 1,8-Diazabicyclo[5.4.0]undec-7-ene
DIBAL Diisobutylaluminium hydride
DIPEA Diisopropylethylamine
DMA Dimethylacetamide
DMEM Dulbecco's modified eagle's medium
DMF N,N-Dimethylformamide
DMSO Dimethylsulfoxide
DPPF 1,1'-Bis(diphenylphosphino)ferrocene
EDTA Ethylenediaminetetraacetic acid
eq. Equivalent
Et Ethyl
$Et_2O$ Diethylether
EtOAc Ethyl acetate
EtOH Ethanol
FC Flash chromatography
h Hour
HATU 1-[Bis(dimethylamino)methylene]-1H-1,2,3-triazolo[4,5-b]pyridinium 3-oxid hexafluorophosphate (CAS 148893-10-1)
HBTU O-Benzotriazole-N,N,N',N'-tetramethyl-uronium-hexafluoro-phosphate (CAS 94790-37-1)
HPLC High performance liquid chromatography
$^i$Bu iso-butyl
$^i$Pr iso-propyl
LC Liquid chromatography
Me Methyl
MeOH Methanol
mesyl Methanesulfonyl
MH+ Mass of the protonated molecule
min Minute
MS Mass spectroscopy
NMR Nuclear magnetic resonance
org. Organic
PBS Phosphate Buffered Saline
Ph Phenyl
Q-Phos 1,2,3,4,5-Pentaphenyl-1'-(di-tert-butylphosphino)ferrocene (CAS 312959-24-3)
rt Room temperature
sat. saturated
sol. solution
TBDMS tert-Butyldimethylsilyl
tBu tert-Butyl
TEA Triethylamine
TFA Trifluoroacetic acid
THF tetrahydrofuran
TLC Thin layer chromatography
$t_R$ Retention time
X-Phos 2-Dicyclohexylphosphino-2',4',6'-triisopropylbiphenyl (CAS 564483-18-7)

PREPARATION OF EXAMPLES

General Procedures

General Procedure 9 for the N-Alkylation of a Pyridine.

A mixture of 2,5-dibromopyridine, an amine, and DBU in DMSO is stirred at 80° C. until the reaction is complete. The amine and DBU may have to be added several times. The mixture is allowed to cool to rt, and the solvents are removed under reduced pressure. Purification of the crude by FC yields the desired product.

Analytical Conditions for LC-MS

Unless notified otherwise, the following conditions were used for analytical LC-MS data:

Conditions 1: Ascentis Express C18 2.7 µm 2.1×30 mm, 5% $CH_3CN$/95% $H_2O$ with 0.05% $NH_4OH$→95% $CH_3CN$ over 2.0 min, 1.4 mL/min.

Conditions 2: Waters Atlantis T3 column, C18, 5 µm, 4.6×30 mm, 5% $CH_3CN$/95% $H_2O$ with 0.04% TFA→100% $CH_3CN$ over 1.0 min, 4.5 mL/min.

Conditions 3: Zorbax SB-Aq column, 3.5 µm, 4.6×50 mm, 5% $CH_3CN$/95% $H_2O$ with 0.04% TFA→100% $CH_3CN$ over 1.0 min, 4.5 mL/min.

Conditions 4: Waters XBridge C18, 2.5 µm, 4.6×30 mm, 5% $CH_3CN$/95% $H_2O$ with 0.04% TFA→100% $CH_3CN$ over 1.0 min, 4.5 mL/min.

Conditions 5: Column Acquity UPLC CSH C18 1.7 µm 2.1×50 mm from Waters, thermostated in the Acquity UPLC Column Manager at 60° C. Eluents: A1: $H_2O$+0.05% HCOOH; B1: $CH_3CN$+0.045% HCOOH. Method: Gradient: 2% B 98% B over 2.0 min. Flow: 1.0 mL/min.

Preparative HPLC

Reaction mixture can often be separated by preparative HPLC. A person skilled in the art will find suitable conditions for each separation.

Automated FC Classical flash chromatography is often replaced by automated systems. This does not change the separation process per se. A person skilled in the art will be able to replace a classical FC process by an automated one, and vice versa. Typical automated systems can be used, as they are provided by Büchi, Isco (Combiflash), or Biotage for instance.

Preparations

4-Cyano-3,5-difluorobenzyl methanesulfonate

A mixture of 2,6-difluoro-4-(hydroxymethyl)benzonitrile (WO 2003101423, 1.20 g, 7.10 mmol) in $CH_2Cl_2$ (40 mL) is cooled to 0° C. TEA (1.48 mL, 10.6 mmol) and mesyl chloride (0.61 mL, 7.8 mmol) are added. The mixture is stirred at 0° C. for 30 min, and aq. sat. $NaHCO_3$ is added. The phases are separated, and the aq. layer is extracted with $CH_2Cl_2$ (3×). The combined org. layers are washed with brine (1×), dried over $MgSO_4$, filtered, and the solvents are removed under reduced pressure to yield the crude title product.

4-(Hydroxymethyl)-2-methylbenzonitrile

To a sol. of 4-bromo-3-methylbenzyl alcohol (1047 mg, 5 mmol) in DMF (10 mL) are added $Zn(CN)_2$ (330 mg, 2.75 mmol), $Pd_2(dba)_3$ (100 mg, 0.109 mmol), DPPF (75 mg, 0.135 mmol) and poly(methylhydrosiloxane) (0.11 mL). The resulting mixture is stirred at 150° C. in a microwave for 40 min. The reaction is repeated twice using the same conditions and quantities. The combined 3 reaction mixtures are filtered over Celite, and the cake is rinsed with EtOAc. The filtrate is concentrated in vacuo. The residue is purified by automated FC (FlashMaster, EtOAc/heptane 0:100→60:40)) to yield the title product. LC-MS: $t_R$=0.62 min., conditions 3.

4-Cyano-3-methylbenzyl methanesulfonate

At 0° C., TEA (2.55 mL, 18.3 mmol) and methanesulfonyl chloride (1.04 mL, 13.4 mmol) are added to a sol. of 4-(hydroxymethyl)-2-methylbenzonitrile (1900 mg, 12.2 mmol) in $CH_2Cl_2$ (31.5 mL). The mixture is stirred at 0° C. for 2 h. The mixture is quenched by the addition of aq. sat. $NaHCO_3$ and the mixture is extracted with $CH_2Cl_2$ (3×). The comb. org. layers are washed with brine, dried over $MgSO_4$, filtered. and concentrated in vacuo to yield the crude title product.

2-Fluoro-5-(hydroxymethyl)benzonitrile

To a sol. of 3-bromo-4-fluorobenzyl alcohol (0.609 mL, 5.00 mmol) in DMA (10 mL) is added $Zn(CN)_2$ (323 mg, 2.75 mmol,), $Pd_2(dba)_3$ (100 mg, 0.109 mmol), DPPF (77.3 mg, 0.135 mmol) and poly(methylhydrosiloxane) (0.11 mL). The resulting mixture is stirred at 150° C. in a microwave for 40 min. The reaction is repeated twice using the same conditions and quantities. The combined 3 reaction mixtures are filtered over Celite, the cake is rinsed with EtOAc, and the filtrate is concentrated in vacuo. Purification of the crude by FC (Combiflash, column 40 g, flow 40 mL/min, EtOAc/heptane 5:95→60:40) yields the title product. LC-MS: $t_R$=0.59 min., conditions 3.

3-Cyano-4-fluorobenzyl methanesulfonate

At 0° C. TEA (3.13 mL, 22.5 mmol) and methanesulfonyl chloride (1.28 mL, 16.5 mmol) are added to a sol. of 2-fluoro-5-(hydroxymethyl)benzonitrile (2.27 g, 15.0 mmol) in $CH_2Cl_2$ (39.3 mL). The mixture is stirred at 0° C. for 30 min. The mixture is quenched by the addition of aq. sat. $NaHCO_3$, and is extracted with $CH_2Cl_2$ (3×). The combined org. layers are washed with brine, dried over $MgSO_4$, filtered and concentrated in vacuo to give the crude title product.

(4-(Difluoromethoxy)-3-fluorophenyl)methanol

A sol. of 3-fluoro-4-difluoromethoxybenzaldehyde (5.00 g, 26.3 mmol) in MeOH (70.0 mL) is cooled to 0° C. $NaBH_4$ (1.49 g, 39.4 mmol) is added portionwise. After addition, the mixture was stirred for 3 days while warming up to rt. Water (10 mL) is added. The mixture is extracted with $CH_2Cl_2$ (3×50 mL). The combined org. extracts are dried over $MgSO_4$, filtered, and concentrated under reduced pressure to yield the crude title product. LC-MS: $t_R$=0.69 min., conditions 3.

4-(Bromomethyl)-1-(difluoromethoxy)-2-fluorobenzene

To a sol. of (4-(difluoromethoxy)-3-fluorophenyl) methanol (2.00 g, 10.4 mmol) in THF (80 mL) at 0° C. are added $PPh_3$ (3.00 g, 11.5 mmol) and $CBr_4$ (4.32 g, 13.0 mmol). The mixture is stirred overnight while warming up to rt. The mixture is filtered, and the filtrate is partitioned between EtOAc and aq. sat. $NH_4Cl$. The org. layer is dried over $MgSO_4$, filtered, and the solvents are removed under reduced pressure. Purification of the crude by automated FC (Büchi, silicagel, EtOAc/heptane 1:99→85:15) yields the title product. LC-MS: $t_R$=0.89 min., conditions 3.

(3-Fluoro-4-(trifluoromethoxy)phenyl)methanol $NaBH_4$ (1.36 g, 36.0 mmol) is added in portions to a sol. of 3-fluoro-4-(trifluoromethoxy)benzaldehyde (5.00 g, 24.0 mmol) in MeOH (80 mL) at 0° C. The mixture is stirred for 3 h while warming up to rt. Water is added carefully and the solvents are partially removed under reduced pressure. The residue is extracted with $CH_2Cl_2$ (2×). The combined org. layers are dried over $MgSO_4$, filtered, and the solvents are removed under reduced pressure to yield the crude title product. LC-MS: $t_R$=0.77 min., conditions 3.

4-(Bromomethyl)-2-fluoro-1-(trifluoromethoxy)benzene

To a sol. of (3-fluoro-4-(trifluoromethoxy)phenyl) methanol (4.50 g, 21.4 mmol) in THF (80 mL) at 0° C. are added $PPh_3$ (6.18 g, 23.6 mmol) and $CBr_4$ (8.88 g, 26.8 mmol). The mixture is stirred for 4 h while warming up to rt. The mixture is filtered, and the filtrate is partitioned between EtOAc and aq. sat. $NH_4Cl$. The org. layer is dried over $MgSO_4$, filtered, and the solvents are removed under reduced pressure. Purification of the crude by automated FC (Büchi, silicagel, EtOAc/heptane 1:99→85:15) yields the title product. LC-MS: $t_R$=0.94 min., conditions 3.

5-(Hydroxymethyl)-2-methylbenzonitrile

To a sol. of (3-bromo-4-methylphenyl)methanol (3.02 g, 15.0 mmol) in DMA (30 mL) are added $Zn(CN)_2$ (989 mg, 8.25 mmol), Pd$_2$(dba)$_3$ (300 mg, 0.328 mmol), DPPF (225 mg, 0.406 mmol) and poly(methylhydrosiloxane) (0.33 mL). The resulting mixture is stirred at 150° C. overnight. The mixture is allowed to cool to rt, filtered over Celite, and the cake is rinsed with EtOAc. The filtrate is concentrated in vacuo. The residue is purified by automated FC (FlashMaster, 100 g silicagel, 45 mL/min, EtOAc/heptane 0:100→60: 40) to yield the title product. LC-MS: t$_R$=0.62 min., conditions 3.

3-Cyano-4-methylbenzyl methanesulfonate

At 0° C., TEA (2.1 mL, 15.1 mmol) and methanesulfonyl chloride (0.858 mL, 11.1 mmol) are added to a sol. of 5-(hydroxymethyl)-2-methylbenzonitrile (1.48 g, 10.1 mmol) in CH$_2$Cl$_2$ (26 mL). The mixture as is stirred at 0° C. for 90 min. The mixture is quenched by the addition of aq. sat. NaHCO$_3$, and is extracted with CH$_2$CO$_2$ (3×). The comb. org. layers are washed with brine, dried over MgSO$_4$, filtered, and concentrated in vacuo to yield the crude title product.

3-Cyano-4-methoxybenzyl methanesulfonate

At 0° C., TEA (1.81 mL, 13.0 mmol) and methanesulfonyl chloride (0.741 mL, 9.55 mmol) are added to a sol. of 5-(hydroxymethyl)-2-methoxybenzonitrile (1.50 g, 8.68 mmol) in THF (22 mL). The mixture is stirred overnight while warming up to rt. The mixture is cooled to 0° C. and TEA (1.81 mL, 13.0 mmol) and methanesulfonyl chloride (0.741 mL, 9.55 mmol) are added again. The mixture is stirred at 0° C. for 1 h then at rt for 3 h. The mixture is heated up to 40° C., and stirred at that temperature overnight. The mixture is quenched by the addition of sat. aq. NaHCO$_3$ sol., and is extracted with CH$_2$Cl$_2$ (3×). The comb. org. layers are washed with brine, dried over MgSO$_4$, filtered, and concentrated in vacuo to give the crude title product.

(3,4-Difluoro-5-methoxyphenyl)methanol

Borane-THF complex (1M in THF, 53.2 mL, 53.2 mmol) is added dropwise to a sol. of 3,4-difluoro-5-methoxybenzoic acid (5.00 g, 26.6 mmol) in THF (136 mL) at rt. The resulting mixture is stirred at rt overnight. The mixture is diluted with EtOAc (180 mL) and brine (25 mL) is added. The layers are separated and the org. phase is dried over MgSO$_4$, filtered and concentrated in vacuo to give the crude title product. LC-MS: t$_R$=0.66 min., conditions 3.

3,4-Difluoro-5-methoxybenzyl methanesulfonate

At 0° C., TEA (5.16 mL, 37 mmol) and methanesulfonyl chloride (2.11 mL, 27.2 mmol) are added to a sol. of (3,4-difluoro-5-methoxyphenyl)methanol (4.37 g, 24.7 mmol) in CH$_2$Cl$_2$ (64 mL). The mixture is stirred at 0° C. for 2 h. The mixture is cooled down again to 0° C. and TEA (5.16 mL, 37 mmol) followed by mesyl chloride (2.11 mL, 27.2 mmol) are added. The mixture is stirred at 0° C. for 90 min, then at rt overnight. The reaction mixture is quenched by the addition of aq. sat. NaHCO$_3$ and is extracted with CH$_2$Cl$_2$ (3×). The comb. org. layers are washed with brine, dried over MgSO$_4$, filtered, and concentrated in vacuo. The residue is purified by automated FC (100 g silicagel, flow: 45 mL/min, EtOAc/heptane 0:100→30:70) to yield the crude title product.

4-(Hydroxymethyl)-2-methoxybenzonitrile

To a sol. of 2-bromo-5-hydroxymethyl-anisole (0.74 mL, 5 mmol, 1 eq) in DMA (10 mL) are added Zn(CN)$_2$ (330 mg, 2.75 mmol Pd$_2$(dba)$_3$ (100 mg, 0.109 mmol), DPPF (75 mg, 0.135 mmol) and poly(methylhydrosiloxane) (0.11 mL). The resulting mixture is stirred at 150° C. in a microwave oven for 40 min. The reaction is repeated twice using the same conditions and quantities. The reaction mixture is filtered over Celite, the cake is rinsed with EtOAc and the filtrate is concentrated in vacuo. The residue is purified by automated FC (Combiflash, 24 g silicagel, flow: 35 mL/min, EtOAc/heptane 0:100→50:50) to yield the title product. LC-MS: t$_R$=0.60 min., conditions 3.

4-Cyano-3-methoxybenzyl methanesulfonate

At 0° C., TEA (3.07 mL, 22.1 mmol) and methanesulfonyl chloride (1.26 mL, 16.2 mmol) are added to a sol. of 4-(hydroxymethyl)-2-methoxybenzonitrile (2.40 g, 14.7 mmol) in CH$_2$Cl$_2$ (40 mL). The mixture as is stirred at 0° C. for 30 min. The mixture is quenched by the addition of aq. sat. NaHCO$_3$, and is extracted with CH$_2$Cl$_2$ (3×). The comb. org. layers are washed with brine, dried over MgSO$_4$, filtered, and concentrated in vacuo to yield the crude title product.

General Procedure for the Preparation of Aminotriazole from 4,5-Dibromo-2H-1,2,3-Triazole.

K$_2$CO$_3$ (2 eq.) is added to a sol. of 4,5-dibromo-2H-1,2,3-triazole (1 eq) in DMF (0.1 M-0.5 M) at rt. The desire benzyl bromide, benzyl chloride, or benzyl methanesulfonate (1 eq) is added slowly, and the mixture is stirred until completion of the reaction (1 h-overnight). The solvents are partially removed under reduced pressure, and the residue is partitioned between water and EtOAc. The aq. layer is extracted with EtOAc (4×). The combined org. layers are washed with brine, dried over MgSO$_4$, filtered, and the solvents are removed under reduced pressure to yield the crude 2-benzyl-4,5-dibromo-2H-1,2,3-triazole. The product is optionally purified by automated FC (silicagel, EtOAc/heptane mixture of solvents).

A sol. of 2-benzyl-4,5-dibromo-2H-1,2,3-triazole (1 eq.) in THF (0.20-0.25 M) is cooled to −5° C. to −25° C. (sometimes −78° C.). iPrMgBr (2M in THF, 2.1 eq) is added, and the reaction is allowed to warm up to −10° C.-rt. After disappearance of the starting material (0.33 h-6 h), aq. sat. NH$_4$Cl is added. The mixture is diluted with Et$_2$O, and the phases are separated. The aq. layer is washed with Et$_2$O (2×). The combined org. layers are dried over MgSO$_4$, filtered, and the solvents are removed under reduced pressure. Purification of the crude by automated FC (silicagel, EtOAc/heptane mixture of solvents) yields the desired 2-benzyl-4-bromo-2H-1,2,3-triazole.

A mixture of 2-benzyl-4-bromo-2H-1,2,3-triazole (1 eq.) and Cu (0.08 eq.) in aq. 25% NH$_4$OH (10 eq.) is stirred at 90-110° C. until the reaction is complete (18 h-6 days). The mixture is allowed to cool to rt, and EtOAc is added. The phases are separated, and the aq. layer is extracted with EtOAc (2×). The combined org. layers are dried over MgSO4, filtered, and the solvents are removed under reduced pressure to yield the crude desired 2-benzyl-2H-1, 2,3-triazol-4-amine.

Following this procedure, the following compounds have been prepared:

| Product name | LC-MS 2-benzyl-4,5-dibromo-2H-1,2,3-triazole $t_R$ (min.), MH+, conditions | LC-MS 2-benzyl-4-bromo-2H-1,2,3-triazole $t_R$ (min.), MH+, conditions | LC-MS final product $t_R$ (min.), MH+, conditions |
|---|---|---|---|
| 2-(4-fluorobenzyl)-2H-1,2,3-triazol-4-amine | 0.94, —, cond. 3 | 0.86, —, cond. 3 | 0.62, 193.25, cond. 3 |
| 2-(3,4-difluorobenzyl)-2H-1,2,3-triazol-4-amine | 0.95, —, cond. 3 | 0.88, —, cond. 3 | 0.66, 211.15, cond. 3 |
| 2-(4-methylbenzyl)-2H-1,2,3-triazol-4-amine | — | 0.90, —, cond. 3 | 0.67, 189.30, cond. 3 |
| 2-(4-methoxybenzyl)-2H-1,2,3-triazol-4-amine | 0.94, —, cond. 3 | 0.86, —, cond. 3 | 0.62, 205.24, cond. 3 |
| 4-((4-amino-2H-1,2,3-triazol-2-yl)methyl)benzonitrile | 0.90, —, cond.3 | 0.83, —, cond. 3 | — |
| 2-(4-ethoxybenzyl)-2H-1,2,3-triazol-4-amine | 0.97, —, cond. 3 | 0.90, —, cond. 3 | 0.68, 219.11, cond. 3 |
| 2-(3,4-dimethoxybenzyl)-2H-1,2,3-triazol-4-amine | 0.90, —, cond. 3 | 0.81, —, cond. 3 | 0.58, 235.12, cond. 3 |
| 2-(3,5-difluoro-4-methoxybenzyl)-2H-1,2,3-triazol-4-amine | 0.95, —, cond. 3 | 0.89, —, cond. 3 | 0.69, 241.15, cond. 3 |
| 2-(4-(2-methoxyethoxy)benzyl)-2H-1,2,3-triazol-4-amine | 0.92, —, cond. 3 | 0.85, —, cond. 3 | 0.62, 249.16, cond. 3 |
| 2-(4-(difluoromethoxy)benzyl)-2H-1,2,3-triazol-4-amine | 0.96, —, cond. 3 | 0.90, —, cond. 3 | 0.70, 241.11, cond. 3 |
| 2-(4-(trifluoromethoxy)benzyl)-2H-1,2,3-triazol-4-amine | 1.00, —, cond. 3 | 0.94, —, cond. 3 | 0.77, 259.07, cond. 3 |
| 2-(4-fluoro-3-methoxybenzyl)-2H-1,2,3-triazol-4-amine | 0.93, —, cond. 3 | 0.86, —, cond. 3 | 0.64, 223.19, cond. 3 |
| 2-(3-fluoro-4-methoxybenzyl)-2H-1,2,3-triazol-4-amine | 0.93, —, cond. 3 | 0.86, —, cond. 3 | 0.64, 223.13, cond. 3 |
| 2-(4-(difluoromethoxy)-3-fluorobenzyl)-2H-1,2,3-triazol-4-amine | 0.93, —, cond. 3 | 0.90, —, cond. 3 | 0.72, 300.08, cond. 3 |
| 2-(3-fluoro-4-(trifluoromethoxy)benzyl)-2H-1,2,3-triazol-4-amine | 0.99, —, cond. 3 | 0.94, —, cond. 3 | 0.78, 277.16, cond. 3 |

General Procedure for the Preparation of Aminotriazole from 4-Nitro-2H-1,2,3-Triazole.

A sol. 4-nitro-1,2,3-triazole (9.6% in DMF, 1 eq.) is diluted in DMF to around 0.25 M. DIPEA (2 eq.) is added. After 45 min., the desired benzyl bromide, benzyl chloride, or benzyl mesylate (1.1 eq) is added. The mixture is stirred at 50° C. until reaction is complete (24 h). The mixture is allowed to cool to rt, and is partitioned between EtOAc and water. The org. layer is dried over MgSO4, filtered, and the solvents are removed under reduced pressure. Purification of the residue by automated FC (silicagel, EtOAc/heptane) yields the desired 2-benzyl-4-nitro-2H-1,2,3-triazole derivative.

A mixture of the starting 2-benzyl-4-nitro-2H-1,2,3-triazole derivative (1 eq), Fe (powder, 325 mesh, 3 eq), and NH4Cl (5 eq) in a 1:2 mixture of water and EtOH (0.2 M) is warmed to 80° C. and stirred at this temperature until reaction is complete (1 h). The mixture is allowed to cool to rt, filtered through Celite, and the solvents are partially removed under reduced pressure. The residue is partitioned between $CH_2CO_2$ and water. The aq. layer is extracted with $CH_2CO_2$ (4×). The combined org. layers are dried over MgSO4, filtered, and the solvents are removed under reduced pressure to yield the desired 2-benzyl-2H-1,2,3-triazol-4-amine derivative.

Following this procedure, the following compounds have been prepared:

sat. NaHCO3 and EtOAc. The aq. layer is extracted with EtOAc (3×). The combined org. layers are washed with brine (1×), dried over MgSO4, filtered, and the solvents are removed under reduced pressure. Purification of the residue by automated FC (silicagel, EtOAc/heptane) or reversed phase HPLC (CH3CN/water) yields the desired methyl or ethyl 2-benzyl-2H-1,2,3-triazole-4-carboxylate derivative.

Aq. 1M LiOH (4-5 eq.) is added to a sol. of the desired methyl or ethyl 2-benzyl-2H-1,2,3-triazole-4-carboxylate derivative (1 eq.) in a 5:1-mixture of THF and MeOH (0.05 M). The mixture is stirred at rt after consumption of the starting material (1 h-overnight). The solvents are partially removed under reduced pressure, and the residue is acidified to pH 4 with aq. 2M HCl. Continuous extraction with $CH_2Cl_2$ leads to an org. layer that is dried over MgSO4, and filtered. Removal of the solvents under reduced pressure yields the desired 2-benzyl-2H-1,2,3-triazole-4-carboxylic acid derivative. Alternative saponification conditions, as for instance aq. NaOH/EtOH+THF, can be used as well.

TEA (2 eq.) and $(PhO)_2P(O)N_3$ (1.2 eq.) are added to a sol. of the desired 2-benzyl-2H-1,2,3-triazole-4-carboxylic acid derivative (1 eq.) in toluene (0.05-0.1 M) at rt. The mixture is heated to 80° C. under stirring, and $Me_3Si(CH_2)_2OH$ (1.5 eq.) is added. The mixture is stirred at 90-100° C. until consumption of the starting materials (2-4 h). The mixture is allowed to cool to rt, and the solvents are removed under reduced pressure. Purification of the residue

| Product name | LC-MS 2-benzyl-4-nitro-2H-1,2,3-triazole $t_R$ (min.), MH+, conditions | LC-MS final product $t_R$ (min.), MH+, conditions |
|---|---|---|
| 4-((4-amino-2H-1,2,3-triazol-2-yl)methyl)-2-fluorobenzonitrile | — | 0.64, 218.10, cond. 3 |

General Procedure for the Preparation of Aminotriazole from Methyl or Ethyl 2H-1,2,3-Triazole-4-Carboxylate.

A sol. of methyl 2H-1,2,3-triazole-4-carboxylate (1 eq.) in DMF (0.1-0.2 M) is cooled to 0° C. NaH (55% suspension in oil, about 1.15 eq) is added, and the mixture is stirred at 0° C. for 15-45 min. The desired benzyl bromide, benzyl chloride, or benzyl mesylate (1.1 eq) is added. The mixture is stirred until consumption of the starting material (6-24 h) while warming up to rt. If necessary, the mixture can be heated up to 60° C. The mixture is partitioned between aq.

by automated FC (silicagel, EtOAc/heptane) yields the desired 2-(trimethylsilyl)ethyl (2-benzyl-2H-1,2,3-triazol-4-yl)carbamate derivative.

TBAF (1.5 eq.) is added slowly to a sol. of the desired 2-(trimethylsilyl)ethyl (2-benzyl-2H-1,2,3-triazol-4-yl)carbamate derivative (1 eq.) in THF (0.25-0.5 M) at 0° C. The mixture is stirred until consumption of the starting material (1 h-24 h) while warming up to rt. The mixture was partitioned between EtOAc and aq. 10% Na2CO3. The org. layer is washed with aq. 10% Na2CO3 (4×), dried over MgSO₄, filtered, and the solvents are removed under reduced pressure to yield the desired 2-benzyl-2H-1,2,3-triazol-4-amine.

Following this procedure, the following compounds have been prepared:

are washed with brine, dried over MgSO₄, filtered, and the solvents are removed under reduced pressure. Purification of the crude by automated FC (Biotage, 25 g silicagel, EtOAc/heptane 1:19→4:6, 25 mL/min) yields the title compound. LC-MS: $t_R$=0.84 min (conditions 3).

| Product name | LC-MS methyl 2-benzyl-2H-1,2,3-triazole-4-carboxylate $t_R$ (min.), MH⁺, conditions | LC-MS 2-benzyl-2H-1,2,3-triazole-4-carboxylic acid $t_R$ (min.), MH⁺, conditions | LC-2-(trimethylsilyl)ethyl (2-benzyl-2H-1,2,3-triazol-4-yl)carbamate $t_R$(min.), MH⁺, conditions | LC-MS final product $t_R$ (min.), MH⁺, conditions |
|---|---|---|---|---|
| 4-((4-amino-2H-1,2,3-triazol-2-yl)methyl)-2-fluoro-6-methoxy-benzonitrile[1] | — | 0.70, —, cond. 3 | 0.96, —, cond. 3 | 0.68, —, cond. 3 |
| 4-((4-amino-2H-1,2,3-triazol-2-yl)methyl)-2-methylbenzonitrile | 0.69, —, cond. 4 | 0.68, 242.33, cond. 3 | 0.96, —, cond. 3 | 0.92, 214.07, cond. 2 |
| 5-((4-amino-2H-1,2,3-triazol-2-yl)methyl)-2-fluorobenzonitrile | 0.72, 275.07, cond 4 | 0.66, —, cond. 3 | 0.95, —, cond. 3 | 0.62, 218.13, cond. 3 |
| 5-((4-amino-2H-1,2,3-triazol-2-yl)methyl)-2-methylbenzonitrile | 0.69, 257.18, cond. 4 | 0.68, 242.30, cond. 3 | 0.96, —, cond. 3 | 1.26, 255.28, cond. 3 |
| 5-((4-amino-2H-1,2,3-triazol-2-yl)methyl)-2-methoxy-benzonitrile | 0.65, 273.14, cond. 4 | 0.66, 259.14, cond. 3 | 0.94, —, cond. 3 | 0.86, 230.20, cond. 3 |
| 2-(3,4-difluoro-5-methoxy-benzyl)-2H-1,2,3-triazol-4-amine | 0.74, 284.15, cond. 4 | 0.72, —, cond. 3 | 0.98, —, cond. 3 | 1.05, 241.21, cond. 3 |
| 4-((4-amino-2H-1,2,3-triazol-2-yl)methyl)-2-methoxy-benzonitrile | — | 0.67, 300.18, cond. 3 | 0.95, —, cond. 3 | 0.63, 230.23, cond. 3 |
| 5-((4-amino-2H-1,2,3-triazol-2-yl)methyl)picolinonitrile | 0.65, 244.17, cond. 3 | 0.52, 230.16, cond. 3[2] | 0.89, 345.12, cond. 3 | 0.47, 201.21, cond. 3 |

[1] From 4-cyano-3,5-difluorobenzyl methanesulfonate, with displacement of a fluorine with MeOH during saponification.
[2] Conditions: To a sol. of the ester (2460 mg, 10.1 mmol) in THF (50 mL) is added aq. 1M HCl (150 mL). The sol. is heated at 75° C. for 28 h. The mixture is partially evaporated under reduced pressure. The residue is diluted with aq. 2M HCl, and is extracted with CH₂Cl₂ (6x). The comb. org. layers are washed with brine, dried over MgSO₄, filtered, and concentrated in vacuo to yield the crude desired product.

Methyl 2-(4-cyclobutoxyphenyl)acetate

Bromocyclobutane (500 mg, 3.70 mmol) and K₂CO₃ (1.25 g, 9.03 mmol) are added to a sol. of methyl 4-hydroxyphenylacetate (500 mg, 3.01 mmol) in DMF (5 mL). The mixture is stirred at 100° C. for 4 h, and is allowed to cool to rt. The solvents are partially removed under reduced pressure, and the residue is purified by automated FC (silicagel, EtOAc/heptane) to yield the title product. LC-MS: $t_R$=0.89 min, conditions 3.

Methyl 2-(4-(vinyloxy)phenyl)acetate

A mixture of methyl-4-hydroxyphenylacetate (1.66 g, 10 mmol), vinyl acetate (1.84 mL, 20.0 mmol), chloro(1,5-cyclooctadiene)iridium(I) dimer (133 mg, 0.20 mmol), and Na₂CO₃ (636 mg, 6.00 mmol) in toluene (10 mL) is stirred at 100° C. for 2.5 h. Subsequently, water is added, and the mixture is extracted with EtOAc. The combined org. layers are washed with brine, dried over MgSO₄, and concentrated under reduced pressure. Purification by automated FC (Biotage, 50 g silicagel, EtOAc/heptane 1:9→4:6, 50 mL/min) yields the title compound. LC-MS: $t_R$=0.83 min (conditions 3).

Methyl 2-(4-cyclopropoxyphenyl)acetate

At −5° C. Et₂Zn (1.0 M in hexanes, 4.8 mL, 4.8 mmol) is added to a sol. of methyl 2-(4-(vinyloxy)phenyl)acetate (384 mg, 2.00 mmol) and CH₂ClI (0.525 mL, 7.20 mmol) in CH₂Cl₂ (15.2 mL). The mixture is stirred between −5° C. and 0° C. for 4 h, and is quenched with aq. sat. NH₄Cl. The mixture is extracted with EtOAc. The combined org. layers

5-Bromo-N-cyclopropyl-N-methylpyridin-2-amine

Prepared according to general procedure 9 from 2,5-dibromopyridine (1.00 g, 4.22 mmol), N-cyclopropyl methylamine hydrochloride (486 mg, 4.52 mmol), and DBU (1.35 mL, 9.03 mmol) in DMSO (30 mL). The same amounts of N-cyclopropyl methylamine hydrochloride, and DBU are added again after 24 h, and the reaction is complete after 7 days. Purification of the crude by automated FC (Büchi, EtOAc/heptane 2:98→3:97→5:95→10:90→15:85, 20 g silicagel, flow 13 mL/min) yields the title product.

5-Bromo-N-(cyclopropylmethyl)-N-methylpyridin-2-amine

A mixture of 2,5-dibromopyridine (2.00 g, 8.44 mmol), (cyclopropylmethyl)methylamine hydrochloride (1.10, 9.03 mmol) and DBU (2.70 mL, 18.1 mmol) in DMSO (30 mL) is stirred at 80° C. for 2 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.59 min, MH⁺=240.96 (conditions 3).

(rac.)-1-Bromo-4-(1-methoxyethyl)benzene

NaH (55% in oil, 197 mg, about 4.51 mmol) is added to a sol. of (rac.)-1-(4-bromophenyl)ethanol (605 mg, 3.01 mmol) in THF (10 mL) at 0° C. The mixture is stirred for 30 min at 0° C., and MeI (0.94 mL, 15 mmol) is added. The mixture is allowed to warm up to rt, and is stirred for 4 h. A little water is added, and the solvents are removed under reduced pressure. The residue is diluted with CH$_2$Cl$_2$, and is dried over MgSO$_4$. The mixture is filtered, and the solvents are removed under reduced pressure. Purification of the residue by automated FC (Büchi, EtOAc/heptane 1:99→3:97→5:95→8:92, 20 g silicagel, flow 18 mL/min) yields the title product.

5-Bromo-N,N-diethylpyridin-2-amine

A mixture of 2,5-dibromopyridine (1.00 g, 4.22 mmol), diethylamine (0.469 mL, 4.52 mmol) and DBU (0.674 mL, 4.52 mmol) in DMSO (30 mL) is stirred at 80° C. for 2 weeks, whereas diethylamine (0.469 mL, 4.52 mmol) and DBU (0.674 mL, 4.52 mmol) are added every 2 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85→20:80) yields the title product. LC-MS: $t_R$=0.53 min, MH$^+$=231.00 (conditions 3).

5-Bromo-2-(3,3-difluoropyrrolidin-1-yl)pyridine

A mixture of 2,5-dibromopyridine (1.00 g, 4.22 mmol), 3,3-difluoropyrrolidine hydrochloride (1.33 g, 9.04 mmol) and DBU (2.70 mL, 18.1 mmol) in DMSO (30 mL) is stirred at 80° C. for 72 h. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.78 min, MH$^+$=264.91 (conditions 3).

5-Bromo-2-(pyrrolidin-1-yl)pyridine

A mixture of 2,5-dibromopyridine (2.00 g, 8.44 mmol), pyrrolidine (0.698 mL, 8.44 mmol) and DBU (1.35 mL, 9.03 mmol) in DMSO (30 mL) is stirred at 80° C. for 4 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.48 min, MH$^+$=229.01 (conditions 3).

3-(4-Bromophenyl)-3-methoxyoxetane 3-(4-Bromophenyl)oxetan-3-ol (WO2008156726, 150 mg, 0.65 mmol) is dissolved in DMF (2.00 mL). The mixture is cooled to 0° C., and NaH (29 mg, 0.72 mmol) is added. The mixture is stirred for 1 h at 0° C., and MeI (0.05 ml, 0.79 mmol) is added. The mixture is stirred at rt over 3 days. Water is added. The mixture is extracted with ether. The combined org. extracts are dried over MgSO$_4$, filtered, and the solvents are removed under reduced pressure under reduced pressure. Purification of the crude by automated FC (Combiflash, column 24 g, flow rate 35 mL/min, EtOAc/heptane 0:100→10:90→30:70) yields the title product. LC-MS: $t_R$=0.80 min, MH$^+$=205.30 (conditions 3).

Oxetan-3-ylmethyl 4-methylbenzenesulfonate p-Toluenesulfonyl chloride (370 mg, 1.94 mmol) is dissolved in pyridine (1.62 mL, 20 mmol). 3-Oxetanemethanol (150 mg, 1.62 mmol) is added. The sol. is stirred at rt for 3 h. The sol. is diluted with EtOAc, and washed with aq. 0.1M HCl and with aq. sat. NaHCO$_3$. The org. layer is dried over Na$_2$SO$_4$, filtered, and the solvents are removed under reduced pressure. Purification of the crude by automated FC (Combiflash, EtOAc/heptane 0:100→50:50) yields the title product. LC-MS: $t_R$=0.75 min, MH$^+$=243.12 (conditions 3).

3-((4-Bromophenoxy)methyl)-3-oxetane

A mixture of oxetan-3-ylmethyl 4-methylbenzenesulfonate (300 mg, 1.24 mmol), 4-bromophenol (236 mg, 1.36 mmol), KI (88 mg, 0.43 mmol) and K$_2$CO$_3$ (342 mg, 2.48 mmol) in DMF (1.8 mL) is stirred at 130° C. for 1.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=0.82 min (conditions 3).

(3,3-Difluorocyclobutyl)methyl 4-methylbenzenesulfonate p-Toluenesulfonyl chloride (281 mg, 1.47 mmol) is dissolved in pyridine (1.23 mL). (3,3-Difluorocyclobutyl)methanol (150 mg, 1.23 mmol) is added. The sol. is stirred at rt overnight. The sol. is diluted with EtOAc, and washed with aq. 0.1M HCl and with aq. sat. NaHCO$_3$. The org. layer is dried over Na$_2$SO$_4$, filtered, and the solvents are removed under reduced pressure to yield the crude title product. LC-MS: $t_R$=0.90 min (conditions 3).

1-Bromo-4-((3,3-difluorocyclobutyl)methoxy)benzene

A mixture of (3,3-difluorocyclobutyl)methyl 4-methylbenzenesulfonate (227 mg, 0.822 mmol), 4-bromophenol (156 mg, 0.904 mmol), KI (59 mg, 0.35 mmol) and K$_2$CO$_3$ (227 mg, 1.64 mmol) in DMF (1.2 mL) is stirred at 130° C. for 2.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=0.97 min (conditions 3).

(3-Methyloxetan-3-yl)methyl 4-methylbenzenesulfonate p-Toluenesulfonyl chloride (2.17 g, 11.4 mmol) is dissolved in CH$_2$Cl$_2$ (9.5 mL) at rt. Pyridine (1.53 mL, 19 mmol) is added, followed by 3-methyl-3-oxetanemethanol (0.977 mL, 9.5 mmol). The sol. is stirred at rt for 4 h. The sol. is diluted with CH$_2$Cl$_2$ and washed with aq. 0.1M HCl and with aq. sat. NaHCO$_3$. The org. layer is dried over Na$_2$SO$_4$, filtered, and the solvents are removed under reduced pressure. Purification of the crude by automated FC (Combiflash, EtOAc/heptane 0:100→60:40) yields the title product. LC-MS: $t_R$=0.80 min, MH$^+$=257.17 (conditions 3).

3-((4-Bromophenoxy)methyl)-3-methyloxetane

A mixture of (3-methyloxetan-3-yl)methyl 4-methylbenzenesulfonate (500 mg, 1.95 mmol), 4-bromphenol (371 mg, 2.15 mmol), KI (139 mg, 0.839 mmol) and K$_2$CO$_3$ (539 mg, 3.9 mmol) in DMF (2.8 mL) is stirred at 130° C. for 1.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g cartridge, EtOAc/heptane 0:100→30:70) yields the title product. LC-MS: $t_R$=0.87 min (conditions 3).

1-Bromo-4-(3,3-difluorocyclobutoxy)benzene

PPh$_3$ (267 mg, 1.02 mmol) is dissolved in dry toluene (2 mL) and cooled to 0° C. Dropwise, diethyl azodicarboxylate (0.165 mL, 1.02 mmol) is added and the light yellow sol. is stirred at 0° C. for 10 min. A sol. of 3,3-difluorocyclobutanol (100 mg, 0.925 mmol) in toluene (0.8 ml) is added. After stirring for another 10 min at rt, 4-bromophenol (160 mg, 0.925 mmol) is added, and the sol. is stirred at 100° C. overnight. The mixture is allowed to cool to rt, and the solvents are removed under reduced pressure. Purification of the crude by automated FC (Combiflash, 40 g silicagel, EtOAc/heptane 0:100→5:95) yields the title product. LC-MS: $t_R$=0.94 min (conditions 3).

5-Bromo-3-fluoro-2-(pyrrolidin-1-yl)pyridine

To a sol. of 5-bromo-2,3-difluoropyridine (680 mg, 3.51 mmol) in DMSO (20 mL), are added pyrrolidine (0.307 mL, 3.68 mmol) and then DBU (1.10 mL, 7.36 mmol). The mixture is heated to 80° C. and stirred at this temperature for one day. The mixture is allowed to cool down to rt. The mixture is diluted with aq. sat. NaHCO$_3$ (200 mL) and EtOAc (200 mL). The layers are separated, and the aq. layer is extracted with EtOAc (lx 100 mL). The comb. org. layers are washed with aq. sat. NaHCO$_3$ (2×200 mL), and brine (1×100 mL), are dried over MgSO$_4$, filtered, and the solvents are removed under reduced pressure to yield the crude title product. LC-MS: $t_R$=0.85 min, MH$^+$=245.09 (conditions 3).

(3-Fluorooxetan-3-yl)methyl 4-methylbenzenesulfonate p-Toluenesulfonyl chloride (216 mg, 1.13 mmol) is dissolved in CH$_2$Cl$_2$ (0.95 mL). Pyridine (0.152 mL, 1.89 mmol) and (3-fluorooxetan-3-yl)methanol (WO 2011084402, 100 mg, 0.943 mmol) is added. The sol. is stirred at rt for 6 h. The sol. is diluted with CH$_2$Cl$_2$, and washed with aq. 0.1M HCl and with aq. sat. NaHCO$_3$. The org. layer is dried over Na$_2$SO$_4$, filtered, and the solvents are removed under reduced pressure to yield the crude title product. LC-MS: $t_R$=0.80 min, MH$^+$=261.13 (conditions 3).

3-((4-Bromophenoxy)methyl)-3-fluorooxetane

A mixture of (3-fluorooxetan-3-yl)methyl 4-methylbenzenesulfonate (138 mg, 0.530 mmol), 4-bromphenol (101 mg, 0.583 mmol), KI (38 mg, 0.23 mmol) and K$_2$CO$_3$ (147 mg, 1.06 mmol) in DMF (0.75 mL) is stirred at 130° C. for 1.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=0.84 min (conditions 3).

(3,3-Difluoro-1-methylcyclobutyl)methyl 4-methylbenzenesulfonate p-Toluenesulfonyl chloride (252 mg, 1.32 mmol) is dissolved in pyridine (1.1 mL). (3,3-Difluoro-1-methyl-cyclobutyl)methanol (150 mg, 1.10 mmol) is added. The sol. is stirred at rt overnight. The sol. is diluted with EtOAc, and washed with aq. 0.1M HCl and with aq. sat. NaHCO$_3$. The org. layer is dried over Na$_2$SO$_4$, filtered, and the solvents are removed under reduced pressure to yield the crude title product. LC-MS: $t_R$=0.93 min, MH$^+$=243.12 (conditions 3).

1-Bromo-4-((3,3-difluoro-1-methylcyclobutyl) methoxy)benzene

A mixture of (3,3-difluoro-1-methylcyclobutyl)methyl 4-methylbenzenesulfonate (232 mg, 0.799 mmol), 4-bromphenol (152 mg, 0.879 mmol), KI (57 mg, 0.34 mmol) and K$_2$CO$_3$ (221 mg, 1.60 mmol) in DMF (1.2 mL) is stirred at 130° C. for 2.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=1.01 min (conditions 3).

Methyl 2-(3-methyl-4-(2,2,2-trifluoroethoxy)phenyl) acetate

To an ice-cooled sol. of methyl 4-hydroxy-3-methylphenylacetate (0.33 mL, 2 mmol) and Cs$_2$CO$_3$ (1.30 g, 4.00 mmol) in DMF (5.3 mL), is added dropwise 2,2,2-trifluoroethyl trifluoromethanesulfonate (0.46 mL, 3.0 mmol). The mixture is stirred at rt over 3 days while warming up to rt. The mixture is partitioned between water (10 mL) and EtOAc (10 mL). The layers are separated. The aq. layer is extracted with EtOAc (2×5 mL). The comb. org. layers are washed with water (2×10 mL) and with brine (1×10 mL), dried over MgSO$_4$, filtered, and the solvents are removed under reduced pressure to yield the crude title product. LC-MS: $t_R$=0.90 min (conditions 3).

2-(3-Methyl-4-(2,2,2-trifluoroethoxy)phenyl)acetic acid

To a sol. of methyl 2-(3-methyl-4-(2,2,2-trifluoroethoxy) phenyl)acetate (710 mg, 2.59 mmol) in THF (8.2 mL) and MeOH (2 mL), is added aq. 1M NaOH (2.8 mL). The sol. is stirred at rt for 1 h. The solvents are removed under reduced pressure. The residue is diluted with water and washed with EtOAc (1×). The aq. phase is acidified with aq. 1M HCl. The mixture is extracted with CH$_2$Cl$_2$ (3×). The comb. org. layers are dried over MgSO$_4$, filtered and the solvents are removed under reduced pressure to yield the crude title product. LC-MS: $t_R$=0.80 min (conditions 3).

4-Bromomethy)-2,6-difluorobenzonitrile 2,6-Difluoro-4-(hydroxymethyl)benzonitrile (WO 2003101423, 2.97 g, 17.6 mmol) is dissolved in THF (80 mL). PPh$_3$ (5.07 g, 19.3 mmol) is added and the mixture is cooled to 0° C. CBr$_4$ (7.28 g, 22.0 mmol) is added in portions. The mixture is stirred for 20 h while warming up to rt. The mixture is filtered, and the filtrate is partitioned between EtOAc and aq. sat. NH$_4$Cl. The org. layer is dried over MgSO4, filtered, and the solvents are removed under reduced pressure. Purification of the residue by automated FC (Büchi, 50 g slilcagel, flow 26 mL/min, EtOAc/heptane 1:99→3:97→8:92→15:85) yields the title product. LC-MS: $t_R$=0.85 min (conditions 3).

2,6-Difluoro-4-((3-nitro-1H-pyrazol-1-yl)methyl) benzonitrile

Prepared according to general procedure 4 from $K_2CO_3$ (2.13 g, 15.4 mmol), 4-bromomethyl-2,6-difluorobenzonitrile (716 mg, 3.09 mmol), 5-nitro-1H-pyrazole (349 mg, 3.09 mmol), and $Bu_4NBr$ (114 mg, 0.309 mmol) in acetone (7 mL). The reaction is complete after 1 h. Purification of the crude by automated FC (Büchi, EtOAc/heptane 1:99→10:90→20:80→50:50→80:20, 24 g silicagel, flow 35 mL/min) yields the title product. LC-MS: $t_R$=0.81 min, MH$^+$=242.22 (conditions 3).

4-((3-Amino-1H-pyrazol-1-yl)methyl)-2,6-difluorobenzonitrile

Prepared according to general procedure 5 from Fe (powder, 358 mg, 6.42 mmol), 2,6-difluoro-4-((3-nitro-1H-pyrazol-1-yl)methyl)benzonitrile (565 mg, 2.14 mmol) and $NH_4Cl$ (572 mg, 10.7 mmol) in a 2:1-mixture of EtOH and water (21 mL). The reaction is complete after 45 min at 85° C. This yields the crude title compound. LC-MS: $t_R$=0.60 min, MH$^+$=276.16 (conditions 3).

General Procedure for the Preparation of Arylacetic Acid Derivatives.

A sol. of bromoaryl/bromoheteroaryl (1 eq.), (2-(tert-butoxy)-2-oxoethyl)zinc(II) chloride (0.5M in $Et_2O$, 1.2 eq.)), $Pd_2(dba)_3$ (0.05 eq.) and Q-Phos or X-Phos (0.1 eq.) in dioxane or THF (0.5M) is stirred between rt and 90° C. until the starting materials are consumed (0.33-48 h). The mixture is allowed to cool to rt, and the solvents are removed under reduced pressure. Chromatographic purification yields the tert-butyl arylacetate.

A sol. of the tert-butyl arylacetate in an acid (HCl/dioxane, or HCOOH) with optionally $CH_2Cl_2$ is prepared at 0° C. This mixture is stirred at 0° C., optionally warming up to rt, until consumption of the starting material. The solvents are removed under reduced pressure to yield the crude desired arylacetic acid derivative.

Following this procedure, the following examples have been prepared

| Product name | LC-MS tert-butyl arylacetate $t_R$ (min.), MH$^+$, conditions | LC-MS final product $t_R$ (min.), MH$^+$, conditions | Acid used for ester hydrolysis |
|---|---|---|---|
| 2-(1-methyl-1H-indazol-5-yl)acetic acid | 0.88, 247.14, cond. 3 | 0.60, —, cond. 3 | 4M HCl/dioxane |
| 2-(1-methyl-1H-indol-5-yl)acetic acid | 0.94, 246.28, cond. 3 | 0.69, —, cond. 3 | See conditions below |
| 2-(4-cyclobutoxyphenyl)acetic acid | 0.89, —, cond. 3 (methyl ester, see above) | 0.77, —, cond. 3 | See conditions below |
| 2-(4-cyclopropoxyphenyl)acetic acid | 0.84, —, cond. 3 (methyl ester, see above) | 0.71, —, cond. 3 | See conditions below |
| 2-(6-(cyclopropyl(methyl)amino)pyridin-3-yl)acetic acid | — | — | 4M HCl/dioxane |
| 2-(6-((cyclopropylmethyl)(methyl)amino)pyridin-3-yl)acetic acid | — | — | 4M HCl/dioxane |
| (rac)-2-(4-(1-methoxyethyl)phenyl)acetic acid | 0.93, —, cond. 3 | 0.65, —, cond. 3 | 4M HCl/dioxane |
| 2-(4-(3-fluorooxetan-3-yl)phenyl)acetic acid | 0.90, —, cond. 3 | 0.63, —, cond. 3 | HCOOH |
| 2-(1H-indol-5-yl)acetic acid | 0.89, 232.19, cond. 3 | 0.69, —, cond. 3 | See conditions below |
| 2-(6-(diethylamino)pyridin-3-yl)acetic acid | 0.66, 265.17, cond. 3 | — | 4M HCl/dioxane |
| 2-(6-(3,3-difluoropyrrolidin-1-yl)pyridin-3-yl)acetic acid | 0.65, 299.17, cond. 3 | 0.42, 242.90, cond. 3 | 4M HCl/dioxane |
| 2-(6-(pyrrolidin-1-yl)pyridin-3-yl)acetic acid | 0.63, 263.14, cond. 3 | 0.42, 207.22, cond. 3 | 4M HCl/dioxane |
| 2-(1,3,3-trimethyl-2-oxoindolin-5-yl)acetic acid | 0.89, 290.01, cond. 3 | 0.63, 275.23, cond. 3 | 4M HCl/dioxane |
| 2-(4-(3-methoxyoxetan-3-yl)phenyl)acetic acid | 0.87, —, cond. 3 | 0.59, —, cond. 3 | HCOOH |
| 2-(3,3-dimethyl-2-oxoindolin-5-yl)acetic acid | 0.83, 276.28, cond. 3 | — | 4M HCl/dioxane |
| 2-(4-(3-methyloxetan-3-yl)phenyl)acetic acid | 0.91, —, cond.3 | 0.64, —, cond. 3 | HCOOH |
| 2-(4-(oxetan-3-yl)phenyl)acetic acid | — | — | HCOOH |
| 2-(1-ethyl-1H-indazol-5-yl)acetic acid | 0.90, —, cond. 3 | 0.64, 205.21, cond. 3 | 4M HCl/dioxane |
| 2-(1,3-dimethyl-1H-indazol-5-yl)acetic acid | 0.90, 261.23, cond. 3 | 0.63, 205.20, cond. 3 | 4M HCl/dioxane |
| 2-(3-cyclopropyl-1H-indazol-5-yl)acetic acid | 0.87, 273.32, cond. 3 | 0.64, 217.13, cond. 1 | 4M HCl/dioxane |
| 2-(1-butyl-1H-indazol-5-yl)acetic acid | 0.89, 289.26, cond. 3 | 0.82, 233.15, cond. 1 | 4M HCl/dioxane |
| 2-(2-methyl-1H-indol-5-yl)acetic acid | 0.91, 246.19, cond. 3 | — | 4M HCl/ dioxane |
| 2-(3-butyl-1H-indazol-5-yl)acetic acid | 0.93, 289.26, cond. 3 | — | 4M HCl/dioxane |
| 2-(1-isopropyl-1H-indazol-5-yl)acetic acid | 0.94, 275.30, cond. 3 | — | 4M HCl/dioxane |

| Product name | LC-MS tert-butyl arylacetate $t_R$ (min.), MH+, conditions | LC-MS final product $t_R$ (min.), MH+, conditions | Acid used for ester hydrolysis |
|---|---|---|---|
| 2-(1-propyl-1H-indazol-5-yl)acetic acid | 0.94, 275.14, cond. 3 | — | 4M HCl/dioxane |
| 2-(3-cyclopropyl-1-methyl-1H-indazol-5-yl)acetic acid | 0.93, 287.18, cond. 3 | — | 4M HCl/dioxane |
| 2-(1-methyl-1H-pyrazolo[3,4-b]pyridin-5-yl)acetic acid | 0.83, 248.28, cond. 3 | — | 4M HCl/dioxane |
| 2-(3-(trifluoromethyl)-1H-indazol-5-yl)acetic acid | — | — | 4M HCl/dioxane |
| 2-(4-(oxetan-3-ylmethoxy)phenyl)acetic acid | 0.89, —, cond. 3 | 0.61, —, cond. 3 | HCOOH |
| 2-(4-((3,3-difluorocyclobutyl)methoxy)phenyl)acetic acid | 1.00, —, cond. 3 | 0.80, —, cond. 3 | HCOOH |
| 2-(4-((3-methyloxetan-3-yl)methoxy)phenyl)acetic acid | 0.93, —, cond. 3 | 0.68, —, cond. 3 | HCOOH |
| 2-(4-(1-(trifluoromethyl)cyclopropyl)phenyl)acetic acid | 1.02, —, cond. 3 | 0.82, 244.21, cond. 3 | HCOOH |
| 2-(4-(3,3-difluorocyclobutoxy)phenyl)acetic acid | 0.98, —, cond. 3 | 0.77, —, cond. 3 | HCOOH |
| 2-(4-(2-cyanopropan-2-yl)phenyl)acetic acid | 0.94, 260.28, cond. 3 | 0.70, —, cond. 3 | 4M HCl/ dioxane |
| 2-(5-fluoro-6-(pyrrolidin-1-yl)pyridin-3-yl)acetic acid | 0.66, 281.22, cond. 3 | 0.44, 225.16, cond. 3 | 4M HCl/dioxane |
| 2-(1-methyl-1H-indazol-6-yl)acetic acid | 0.88, 247.14, cond. 3 | 0.60, —, cond. 3 | 4M HCl/dioxane |
| 2-(4-((3-fluorooxetan-3-yl)methoxy)phenyl)acetic acid | 0.91, —, cond. 3 | 0.65, —, cond. 3 | HCOOH |
| 2-(4-((3,3-difluoro-1-methylcyclobutyl)methoxy)phenyl)acetic acid | 1.04, —, cond. 3 | 0.85, —, cond. 3 | HCOOH |
| 2-(4-(1-cyanocyclopropyl)phenyl)acetic acid | 0.92, 258.14, cond. 3 | 0.68, —, cond. 3 | TFA |
| 2-(4-(pentafluoro-λ6-sulfanyl)phenyl)acetic acid | 0.89, —, cond. 3 | 0.66, 281.22, cond. 3 | HCOOH |
| 2-(4-(1,1,1-trifluoro-2-methylpropan-2-yl)phenyl)acetic acid | 1.02, —, cond. 3 | 0.82, —, cond. 3 | TFA |
| rac-2-(4-((1R*,2R*)-2-(trifluoromethyl)cyclopropyl)phenyl)acetic acid | 1.01, —, cond. 3 | 0.82, —, cond. 3 | TFA |

2-(1-Methyl-1H-indol-5-yl)acetic acid

A mixture of tert-butyl 2-(1H-indol-5-yl)acetate (53 mg, 0.22 mmol) and NaOH (11 mg, 0.26 mmol) in MeOH (4 mL) is heated to 55° C. and stirred at this temperature for 2 h. The mixture is allowed to cool to rt, and the solvents are removed under reduced pressure. The residue is diluted with $CH_2Cl_2$, and aq. 1M HCl is added to pH 2-3. The phases are separated, and the org. layer is dried over $MgSO_4$, and filtered. The solvents are removed under reduced pressure to yield the crude title compound. LC-MS: $t_R$=0.69 min (conditions 3).

2-(4-Cyclobutoxyphenyl)acetic acid

A sol. of methyl 2-(4-cyclobutoxyphenyl)acetate (440 mg, 2.00 mmol) and aq. 2.5M NaOH (3 mL) in MeOH (6 mL) is stirred at rt for 1 h. The solvents are partially removed under reduced pressure, and the residue is covered with $CH_2Cl_2$. Aq. 1M HCl is added to reach a pH=3, and the phases are separated in a Separator®. The org. layer is dried over $MgSO_4$, filtered, and the solvents are removed under reduced pressure to yield the crude title product.

2-(4-Cyclopropoxyphenyl)acetic acid

A sol. of methyl 2-(4-cyclopropoxyphenyl)acetate (364 mg, 1.76 mmol) and LiOH $H_2O$ (111 mg, 2.65 mmol) in THF/MeOH/$H_2O$ (3:1:1) (10 ml) is stirred at 0° C. for 3 h. The mixture is acidified with aq. 1 M HCl to pH 3 and extracted with EtOAc. The combined org. layers are washed with brine, dried over $MgSO_4$, and filtered. Removing the solvents under reduced pressure yields the crude title compound.

2-(1H-Indol-5-yl)acetic acid

A mixture of tert-butyl 2-(1H-indol-5-yl)acetate (50 mg, 0.22 mmol) and NaOH (11 mg, 0.26 mmol) in MeOH (4 mL) is heated to 55° C. and stirred at this temperature for 2 h. The mixture is allowed to cool to rt, and the solvents are removed under reduced pressure. The residue is diluted with $CH_2Cl_2$, and aq. 1M HCl is added to pH 2-3. The phases are separated, and the org. layer is dried over $MgSO_4$, and filtered. The solvents are removed under reduced pressure to yield the crude title compound.

General Procedure for an Amide Coupling.

Unless indicated otherwise, a mixture of the desired carboxylic acid (1 eq.), the desired amine (1 eq), N-methylmorpholine or DIPEA (5 eq.) and HATU or HBTU (1 eq.) in DMF (0.1-0.2 M) is stirred until the reaction is complete (1 h-overnight). The solvents are removed under reduced pressure. An aq. work-up (basic and/or acidic) is optionally realized. The residue is purified by automated FC, or by HPLC, to yield the desired product. Alternatively, the product can be isolated by crystallization.

Following this procedure, the following examples have been prepared:

| Example number | Product name | LC-MS $t_R$ (min.), MH+, conditions |
|---|---|---|
| 1 | N-[2-(4-Fluoro-benzyl)-2H-[1,2,3]triazol4-yl]-2-(4-isopropyl-phenyl)-acetamide | 0.95, 353.26, cond. 3 |
| 2 | 2-(4-Dimethylamino-phenyl)-N-[2-(4-fluoro-benzyl)-2H-[1,2,3]triazol-4-yl]-acetamide | 0.57, 354.23, cond. 2 |
| 5 | N-[2-(3,4-Difluoro-benzyl)-2H-[1,2,3]triazol-4-yl]-2-(4-isopropyl-phenyl)-acetamide | 0.96, 371. 28, cond. 3 |
| 6 | N-[2-(3,4-Difluoro-benzyl)-2H-[1,2,3]triazol-4-yl]-2-(1-methyl-1H-indazol-5-yl)-acetamide | 0.85, 383.29, cond. 3 |
| 7 | N-[2-(3,4-Difluoro-benzyl)-2H-[1,2,3]triazol-4-yl]-2-(1-methyl-1H-indol-5-yl)-acetamide | 0.90, 382.29, cond. 3 |
| 8 | N-[2-(3,4-Difluoro-benzyl)-2H-[1,2,3]triazol-4-yl]-2-(1H-indol-6-yl)-acetamide | 0.86, 368.29, cond. 3 |
| 9 | 2-(4-Cyclobutoxy-phenyl)-N-[2-(3,4-difluoro-benzyl)-2H-[1,2,3]triazol-4-yl]-acetamide | 0.94, 399.31, cond. 3 |
| 10 | 2-(4-Cyclopropoxy-phenyl)-N-[2-(3,4-difluoro-benzyl)-2H-[1,2,3]triazol-4-yl]-acetamide | 0.92, 385.19, cond.3 |
| 11 | 2-[6-(Cyclopropyl(methyl)amino)-pyridin-3-yl]-N-[2-(3,4-difluoro-benzyl)-2H-[1,2,3]triazol-4-yl]-acetamide | 0.67, 399.32, cond. 3 |
| 12 | 2-[6-(Cyclopropylmethyl-methyl-amino)-pyridin-3-yl]-N-[2-(3,4-difluoro-benzyl)-2H-[1,2,3]triazol-4-yl]-acetamide | 0.70, 413.32, cond. 3 |
| 13 | rac-N-[2-(3,4-Difluoro-benzyl)-2H-[1,2,3]triazol-4-yl]-2-[4-(1-methoxy-ethyl)-phenyl]-acetamide | 0.88, 387.32, cond. 3 |
| 14 | N-[2-(3,4-Difluoro-benzyl)-2H-[1,2,3]triazol-4-yl]-2-[4-(3-fluoro-oxetan-3-yl)-phenyl]-acetamide | 0.86, 403.03, cond. 3 |
| 15 | N-[2-(3,4-Difluoro-benzyl)-2H-[1,2,3]triazol-4-yl]-2-(1H-indol-5-yl)-acetamide | 0.85, 368.25, cond. 3 |
| 16 | 2-(6-Diethylamino-pyridin-3-yl)-N-[2-(3,4-difluoro-benzyl)-2H-[1,2,3]triazol-4-yl]-acetamide | 0.69, 401.21, cond. 3 |
| 17 | N-[2-(3,4-Difluoro-benzyl)-2H-[1,2,3]triazol-4-yl]-2-[6-(3,3-difluoro-pyrrolidin-1-yl)-pyridin-3-yl]-acetamide | 0.69, 435.25, cond. 3 |
| 18 | N-[2-(3,4-Difluoro-benzyl)-2H-[1,2,3]triazol-4-yl]-2-(6-pyrrolidin-1-yl-pyridin-3-yl)-acetamide | 0.67, 399.33, cond. 3 |
| 19 | N-[2-(3,4-Difluoro-benzyl)-2H-[1,2,3]triazol-4-yl]-2-(1,3,3-trimethyl-2-oxo-2,3-dihydro-1H-indol-5-yl)-acetamide | 0.85, 426.31, cond. 3 |
| 20 | N-[2-(3,4-Difluoro-benzyl)-2H-[1,2,3]triazol-4-yl]-2-[4-(3-methoxy-oxetan-3-yl)-phenyl]-acetamide | 0.84, 415.31, cond. 3 |
| 21 | N-[2-(3,4-Difluoro-benzyl)-2H-[1,2,3]triazol-4-yl]-2-(3,3-dimethyl-2-oxo-2,3-dihydro-1H-indol-5-yl)-acetamide | 0.80, 453.22[(1)], cond. 3 |
| 22 | N-[2-(3,4-Difluoro-benzyl)-2H-[1,2,3]triazol-4-yl]-2-[4-(3-methyl-oxetan-3-yl)-phenyl]-acetamide | 0.87, 399.13, cond. 3 |
| 23 | N-[2-(3,4-Difluoro-benzyl)-2H-[1,2,3]triazol-4-yl]-2-(4-oxetan-3-yl-phenyl)-acetamide | 0.84, 385.06, cond. 3 |
| 24 | 2-(4-Isopropyl-phenyl)-N-[2-(4-methyl-benzyl)-2H-[1,2,3]triazol-4-yl]-acetamide | 0.97, 349.37, cond. 3 |
| 25 | 2-(4-Isopropyl-phenyl)-N-[2-(4-methoxy-benzyl)-2H-[1,2,3]triazol-4-yl]-acetamide | 0.94, 365.35, cond. 3 |
| 26 | N-[2-(4-Cyano-benzyl)-2H-[1,2,3]triazol-4-yl]-2-(4-isopropyl-phenyl)-acetamide | 0.93, 360.34, cond. 3 |
| 27 | N-[2-(3,4-Difluoro-benzyl)-2H-[1,2,3]triazol-4-yl]-2-(1-ethyl-1H-indazol-5-yl)-acetamide | 1.33, 397.08, cond. 1 |
| 28 | N-[2-(3,4-Difluoro-benzyl)-2H-[1,2,3]triazol-4-yl]-2-(1,3-dimethyl-1H-indazol-5-yl)-acetamide | 1.29, 397.08, cond. 1 |
| 29 | 2-(3-Cyclopropyl-1H-indazol-5-yl)-N-[2-(3,4-difluoro-benzyl)-2H-[1,2,3]triazol-4-yl]-acetamide | 1.29, 409.12, cond. 1 |
| 30 | 2-(1-Butyl-1H-indazol-5-yl)-N-[2-(3,4-difluoro-benzyl)-2H-[1,2,3]triazol-4-yl]-acetamide | 1.53, 425.13, cond. 1 |
| 31 | N-[2-(3,4-Difluoro-benzyl)-2H-[1,2,3]triazol-4-yl]-2-(2-methyl-1H-indol-5-yl)-acetamide | 1.39, 382.09, cond. 1 |
| 32 | 2-(3-Butyl-1H-indazol-5-yl)-N-[2-(3,4-difluoro-benzyl)-2H-[1,2,3]triazol-4-yl]-acetamide | 1.42, 425.05, cond. 1 |
| 33 | N-[2-(3,4-Difluoro-benzyl)-2H-[1,2,3]triazol-4-yl]-2-(1-isopropyl-1H-indazol-5-yl)-acetamide | 1.42, 411.05, cond. 1 |
| 34 | N-[2-(3,4-Difluoro-benzyl)-2H-[1,2,3]triazol-4-yl]-2-(1-propyl-1H-indazol-5-yl)-acetamide | 1.42, 411.13, cond. 1 |
| 35 | 2-(3-Cyclopropyl-1-methyl-1H-indazol-5-yl)-N-[2-(3,4-difluoro-benzyl)-2H-[1,2,3]triazol-4-yl]-acetamide | 1.41, 422.99, cond. 1 |
| 38 | N-[2-(3,4-Difluoro-benzyl)-2H-[1,2,3]triazol-4-yl]-2-(1-methyl-1H-pyrazolo[3,4-b]pyridin-5-yl)-acetamide | 1.14, 384.04, cond. 1 |
| 39 | N-[2-(3,4-Difluoro-benzyl)-2H-[1,2,3]triazol-4-yl]-2-(3-trifluoromethyl-1H-indazol-5-yl)-acetamide | 0.88, 437.13, cond. 3 |
| 40 | N-[2-(4-Ethoxy-benzyl)-2H-[1,2,3]triazol-4-yl]-2-(1-methyl-1H-indol-5-yl)-acetamide | 0.91, 390.25, cond. 3 |
| 41 | 2-[6-(3,3-Difluoro-pyrrolidin-1-yl)-pyridin-3-yl]-N-[2-(4-ethoxy-benzyl)-2H-[1,2,3]triazol-4-yl]-acetamide | 0.70, 443.24, cond. 3 |
| 42 | N-[2-(4-Ethoxy-benzyl)-2H-[1,2,3]triazol-4-yl]-2-[4-(3-methyl-oxetan-3-yl)-phenyl]-acetamide | 0.88, 407.32, cond. 3 |

-continued

| Example number | Product name | LC-MS $t_R$ (min.), MH+, conditions |
|---|---|---|
| 43 | 2-(4-tert-Butyl-phenyl)-N-[2-(4-ethoxy-benzyl)-2H-[1,2,3]triazol-4-yl]-acetamide | 0.99, 393.32, cond. 3 |
| 44 | N-[2-(4-Ethoxy-benzyl)-2H-[1,2,3]triazol-4-yl]-2-(4-isopropyl-phenyl)-acetamide | 0.97, 379.31, cond. 3 |
| 45 | N-[2-(4-Ethoxy-benzyl)-2H-[1,2,3]triazol-4-yl]-2-(6-pyrrolidin-1-yl-pyridin-3-yl)-acetamide | 0.68, 407.03, cond. 3 |
| 46 | N-[2-(4-Ethoxy-benzyl)-2H-[1,2,3]triazol-4-yl]-2-(1-methyl-1H-indazol-5-yl)-acetamide | 0.86, 391.27, cond. 3 |
| 47 | 2-(6-Diethylamino-pyridin-3-yl)-N-[2-(3,4-dimethoxy-benzyl)-2H-[1,2,3]triazol-4-yl]-acetamide | 0.64, 425.27, cond. 3 |
| 48 | 2-[6-(3,3-Difluoro-pyrrolidin-1-yl)-pyridin-3-yl]-N-[2-(3,4-dimethoxy-benzyl)-2H-[1,2,3]triazol-4-yl]-acetamide | 0.64, 459.23, cond. 3 |
| 49 | 2-(4-tert-Butyl-phenyl)-N-[2-(3,4-dimethoxy-benzyl)-2H-[1,2,3]triazol-4-yl]-acetamide | 0.94, 409.29, cond. 3 |
| 50 | N-[2-(3,4-Dimethoxy-benzyl)-2H-[1,2,3]triazol-4-yl]-2-(4-isopropyl-phenyl)-acetamide | 0.92, 395.30, cond. 3 |
| 51 | N-[2-(3,4-Dimethoxy-benzyl)-2H-[1,2,3]triazol-4-yl]-2-(6-pyrrolidin-1-yl-pyridin-3-yl)-acetamide | 0.62, 423.39, cond. 3 |
| 52 | N-[2-(4-Fluoro-benzyl)-2H-[1,2,3]triazol-4-yl]-2-(1-methyl-1H-indol-5-yl)-acetamide | 0.88, 364.25, cond. 3 |
| 53 | N-[2-(4-Fluoro-benzyl)-2H-[1,2,3]triazol-4-yl]-2-[4-(3-methyl-oxetan-3-yl)-phenyl]-acetamide | 0.85, 381.29, cond.3 |
| 54 | 2-(4-tert-Butyl-phenyl)-N-[2-(4-fluoro-benzyl)-2H-[1,2,3]triazol-4-yl]-acetamide | 0.97, 367.31, cond. 3 |
| 55 | N-[2-(4-Fluoro-benzyl)-2H-[1,2,3]triazol-4-yl]-2-(6-pyrrolidin-1-yl-pyridin-3-yl)-acetamide | 0.65, 381.28, cond. 3 |
| 56 | N-[2-(4-Fluoro-benzyl)-2H-[1,2,3]triazol-4-yl]-2-(1-methyl-1H-indazol-5-yl)-acetamide | 0.83, 365.29, cond. 3 |
| 57 | N-[2-(4-Methoxy-benzyl)-2H-[1,2,3]triazol-4-yl]-2-(1-methyl-1H-indol-5-yl)-acetamide | 0.88, 376.27, cond. 3 |
| 58 | 2-(6-Diethylamino-pyridin-3-yl)-N-[2-(4-methoxy-benzyl)-2H-[1,2,3]triazol-4-yl]-acetamide | 0.67, 395.25, cond. 3 |
| 59 | 2-[6-(3,3-Difluoro-pyrrolidin-1-yl)-pyridin-3-yl]-N-[2-(4-methoxy-benzyl)-2H-[1,2,3]triazol-4-yl]-acetamide | 0.67, 429.25, cond. 3 |
| 60 | N-[2-(4-Methoxy-benzyl)-2H-[1,2,3]triazol-4-yl]-2-[4-(3-methyl-oxetan-3-yl)-phenyl]-acetamide | 0.84, 393.29, cond. 3 |
| 61 | 2-(4-tert-Butyl-phenyl)-N-[2-(4-methoxy-benzyl)-2H-[1,2,3]triazol-4-yl]-acetamide | 0.97, 379.31, cond. 3 |
| 62 | N-[2-(4-Methoxy-benzyl)-2H-[1,2,3]triazol-4-yl]-2-(6-pyrrolidin-1-yl-pyridin-3-yl)-acetamide | 0.65, 393.32, cond. 3 |
| 63 | N-[2-(4-Methoxy-benzyl)-2H-[1,2,3]triazol-4-yl]-2-(1-methyl-1H-indazol-5-yl)-acetamide | 0.82, 377.28, cond. 3 |
| 64 | N-[2-(4-Methyl-benzyl)-2H-[1,2,3]triazol-4-yl]-2-(1-methyl-1H-indol-5-yl)-acetamide | 0.90, 360.04, cond. 3 |
| 65 | 2-[6-(3,3-Difluoro-pyrrolidin-1-yl)-pyridin-3-yl]-N-[2-(4-methyl-benzyl)-2H-[1,2,3]triazol-4-yl]-acetamide | 0.69, 413.03, cond. 3 |
| 66 | 2-(4-tert-Butyl-phenyl)-N-[2-(4-methyl-benzyl)-2H-[1,2,3]triazol-4-yl]-acetamide | 0.99, 363.08, cond. 3 |
| 67 | N-[2-(4-Methyl-benzyl)-2H-[1,2,3]triazol-4-yl]-2-[4-(3-methyl-oxetan-3-yl)-phenyl]-acetamide | 0.87, 377.02, cond. 3 |
| 68 | N-[2-(4-Methyl-benzyl)-2H-[1,2,3]triazol-4-yl]-2-(6-pyrrolidin-1-yl-pyridin-3-yl)-acetamide | 0.68, 377.04, cond. 3 |
| 69 | N-[2-(4-Methyl-benzyl)-2H-[1,2,3]triazol-4-yl]-2-(1-methyl-1H-indazol-5-yl)-acetamide | 0.85, 361.02, cond. 3 |
| 70 | N-[2-(4-Cyano-3-fluoro-benzyl)-2H-[1,2,3]triazol-4-yl]-2-(1-methyl-1H-indol-5-yl)-acetamide | 0.87, 388.99, cond. 3 |
| 71 | N-[2-(4-Cyano-3-fluoro-benzyl)-2H-[1,2,3]triazol-4-yl]-2-[6-(3,3-difluoro-pyrrolidin-1-yl)-pyridin-3-yl]-acetamide | 0.67, 441.96, cond. 3 |
| 72 | N-[2-(4-Cyano-3-fluoro-benzyl)-2H-[1,2,3]triazol-4-yl]-2-[4-(3-methyl-oxetan-3-yl)-phenyl]-acetamide | 0.84, 405.99, cond. 3 |
| 73 | 2-(4-tert-Butyl-phenyl)-N-[2-(4-cyano-3-fluoro-benzyl)-2H-[1,2,3]triazol-4-yl]-acetamide | 0.95, 392.03, cond. 3 |
| 74 | N-[2-(4-Cyano-3-fluoro-benzyl)-2H-[1,2,3]triazol-4-yl]-2-(4-isopropyl-phenyl)-acetamide | 0.93, 378.03, cond. 3 |
| 75 | N-[2-(4-Cyano-3-fluoro-benzyl)-2H-[1,2,3]triazol-4-yl]-2-(6-pyrrolidin-1-yl-pyridin-3-yl)-acetamide | 0.65, 406.01, cond. 3 |
| 76 | N-[2-(4-Cyano-3-fluoro-benzyl)-2H-[1,2,3]triazol-4-yl]-2-(1-methyl-1H-indazol-5-yl)-acetamide | 0.82, 389.98, cond. 3 |
| 77 | N-[2-(3,5-Difluoro-4-methoxy-benzyl)-2H-[1,2,3]triazol-4-yl]-2-(1-methyl-1H-indol-5-yl)-acetamide | 0.90, 411.99, cond. 3 |
| 78 | N-[2-(3,5-Difluoro-4-methoxy-benzyl)-2H-[1,2,3]triazol-4-yl]-2-[4-(3-methyl-oxetan-3-yl)-phenyl]-acetamide | 0.87, 428.99, cond. 3 |
| 79 | 2-(4-tert-Butyl-phenyl)-N-[2-(3,5-difluoro-4-methoxy-benzyl)-2H-[1,2,3]triazol-4-yl]-acetamide | 0.98, 415.04, cond. 3 |

-continued

| Example number | Product name | LC-MS $t_R$ (min.), MH+, conditions |
|---|---|---|
| 80 | N-[2-(3,5-Difluoro-4-methoxy-benzyl)-2H-[1,2,3]triazol-4-yl]-2-(4-isopropyl-phenyl)-acetamide | 0.96, 400.99, cond. 3 |
| 81 | N-[2-(3,5-Difluoro-4-methoxy-benzyl)-2H-[1,2,3]triazol-4-yl]-2-(6-pyrrolidin-1-yl-pyridin-3-yl)-acetamide | 0.68, 429.01, cond. 3 |
| 82 | N-[2-(3,5-Difluoro-4-methoxy-benzyl)-2H-[1,2,3]triazol-4-yl]-2-(1-methyl-1H-indazol-5-yl)-acetamide | 0.85, 413.00, cond. 3 |
| 83 | 2-(4-tert-Butyl-phenyl)-N-[2-(4-cyclopropylmethoxy-benzyl)-2H-[1,2,3]triazol-4-yl]-acetamide | 1.01, 419.05, cond. 3 |
| 84 | N-[2-(4-Cyclopropylmethoxy-benzyl)-2H-[1,2,3]triazol-4-yl]-2-(1-methyl-1H-indol-5-yl)-acetamide | 0.93, 416.94, cond. 3 |
| 85 | N-[2-(4-Cyclopropylmethoxy-benzyl)-2H-[1,2,3]triazol-4-yl]-2-(1-methyl-1H-indazol-5-yl)-acetamide | 0.89, 417.00, cond. 3 |
| 86 | 2-(4-tert-Butyl-phenyl)-N-{2-[4-(2-methoxy-ethoxy)-benzyl]-2H-[1,2,3]triazol-4-yl}-acetamide | 0.95, 423.06, cond. 3 |
| 87 | N-{2-[4-(2-Methoxy-ethoxy)-benzyl]-2H-[1,2,3]triazol-4-yl}-2-(1-methyl-1H-indol-5-yl)-acetamide | 0.86, 420.02, cond. 3 |
| 88 | 2-(4-tert-Butyl-phenyl)-N-[2-(4-difluoromethoxy-benzyl)-2H-[1,2,3]triazol-4-yl]-acetamide | 0.98, 415.03, cond. 3 |
| 89 | N-[2-(4-Difluoromethoxy-benzyl)-2H-[1,2,3]triazol-4-yl]-2-(1-methyl-1H-indol-5-yl)-acetamide | 0.90, 412.02, cond. 3 |
| 90 | 2-(4-tert-Butyl-phenyl)-N-[2-(4-trifluoromethoxy-benzyl)-2H-[1,2,3]triazol4-yl]-acetamide | 1.01, 432.96, cond. 3 |
| 91 | 2-(1-Methyl-1H-indol-5-yl)-N-[2-(4-trifluoromethoxy-benzyl)-2H-[1,2,3]triazol-4-yl]-acetamide | 0.94, 429.94, cond. 3 |
| 92 | 2-(1-Methyl-1H-indazol-5-yl)-N-[2-(4-trifluoromethoxy-benzyl)-2H-[1,2,3]triazol-4-yl]-acetamide | 0.90, 430.97, cond. 3 |
| 93 | 2-[4-(3-Methyl-oxetan-3-yl)-phenyl]-N-[2-(4-trifluoromethoxy-benzyl)-2H-[1,2,3]triazol-4-yl]-acetamide | 0.92, 446.95, cond. 3 |
| 94 | 2-[6-(3,3-Difluoro-pyrrolidin-1-yl)-pyridin-3-yl]-N-[2-(4-fluoro-benzyl)-2H-[1,2,3]triazol-4-yl]-acetamide | 0.67, 417.20, cond. 3 |
| 95 | 2-(6-Diethylamino-pyridin-3-yl)-N-[2-(4-fluoro-benzyl)-2H-[1,2,3]triazol-4-yl]-acetamide | 0.67, 383.20, cond. 3 |
| 96 | 2-(4-tert-Butyl-phenyl)-N-[2-(4-cyano-benzyl)-2H-[1,2,3]triazol-4-yl]-acetamide | 1.55, 374.03, cond. 1 |
| 97 | N-[2-(4-Cyano-benzyl)-2H-[1,2,3]triazol-4-yl]-2-[6-(3,3-difluoro-pyrrolidin-1-yl)-pyridin-3-yl]-acetamide | 1.21, 423.97, cond. 1 |
| 98 | N-[2-(4-Cyano-benzyl)-2H-[1,2,3]triazol-4-yl]-2-(6-pyrrolidin-1-yl-pyridin-3-yl)-acetamide | 1.18, 388.05, cond. 1 |
| 99 | N-[2-(4-Cyano-benzyl)-2H-[1,2,3]triazol-4-yl]-2-(1-methyl-1H-indol-5-yl)-acetamide | 1.26, 371.04, cond. 1 |
| 100 | N-[2-(4-Cyano-benzyl)-2H-[1,2,3]triazol4-yl]-2-(1,3-dimethyl-1H-indol-5-yl)-acetamide | 1.37, 385.05, cond. 1 |
| 101 | N-[2-(4-Cyano-benzyl)-2H-[1,2,3]triazol-4-yl]-2-(1-methyl-1H-indazol-6-yl)-acetamide | 1.07, 372.04, cond. 1 |
| 102 | N-[2-(4-Cyano-benzyl)-2H-[1,2,3]triazol-4-yl]-2-(1,3-dimethyl-1H-indazol-5-yl)-acetamide | 1.11, 386.04, cond. 1 |
| 103 | N-[2-(4-Cyano-benzyl)-2H-[1,2,3]triazol-4-yl]-2-(1-ethyl-1H-indazol-5-yl)-acetamide | 1.15, 386.03, cond. 1 |
| 104 | N-[2-(4-Cyano-benzyl)-2H-[1,2,3]triazol-4-yl]-2-(1-propyl-1H-indazol-5-yl)-acetamide | 1.24, 400.11, cond. 1 |
| 105 | N-[2-(4-Cyano-3-fluoro-benzyl)-2H-[1,2,3]triazol-4-yl]-2-(1,3-dimethyl-1H-indol-6-yl)-acetamide | 0.91, 403.12, cond. 3 |
| 106 | N-[2-(4-Cyano-benzyl)-2H-[1,2,3]triazol-4-yl]-2-(1,3-dimethyl-1H-indol-6-yl)-acetamide | 0.89, 385.11, cond. 3 |
| 108 | N-[2-(4-Fluoro-3-methoxy-benzyl)-2H-[1,2,3]triazol-4-yl]-2-[4-(oxetan-3-ylmethoxy)-phenyl]-acetamide | 1.24, 427.13, cond. 1 |
| 109 | N-[2-(4-Fluoro-3-methoxy-benzyl)-2H-[1,2,3]triazol-4-yl]-2-(1-methyl-1H-indazol-6-yl)-acetamide | 1.20, 395.09, cond. 1 |
| 110 | N-[2-(4-Fluoro-3-methoxy-benzyl)-2H-[1,2,3]triazol-4-yl]-2-[4-(3-methoxy-oxetan-3-yl)-phenyl]-acetamide | 1.21, 427.15, cond. 1 |
| 111 | 2-[4-(3,3-Difluoro-cyclobutylmethoxy)-phenyl]-N-[2-(4-fluoro-3-methoxy-benzyl)-2H-[1,2,3]triazol-4-yl]-acetamide | 1.55, 461.13, cond. 1 |
| 112 | N-[2-(4-Fluoro-3-methoxy-benzyl)-2H-[1,2,3]triazol-4-yl]-2-[4-(3-methyl-oxetan-3-ylmethoxy)-phenyl]-acetamide | 1.33, 441.16, cond. 1 |
| 113 | N-[2-(4-Fluoro-3-methoxy-benzyl)-2H-[1,2,3]triazol-4-yl]-2-[4-(1-trifluoromethyl-cyclopropyl)-phenyl]-acetamide | 1.61, 449.09, cond. 1 |
| 114 | 2-[4-(3,3-Difluoro-cyclobutoxy)-phenyl]-N-[2-(4-fluoro-3-methoxy-benzyl)-2H-[1,2,3]triazol-4-yl]-acetamide | 1.51, 447.13, cond. 1 |
| 115 | 2-[6-(3,3-Difluoro-pyrrolidin-1-yl)-pyridin-3-yl]-N-[2-(4-fluoro-3-methoxy-benzyl)-2H-[1,2,3]triazol-4-yl]-acetamide | 1.32, 447.13, cond. 1 |
| 116 | N-[2-(4-Fluoro-3-methoxy-benzyl)-2H-[1,2,3]triazol-4-yl]-2-[4-(3-fluoro-oxetan-3-yl)-phenyl]-acetamide | 1.30, 415.08, cond. 1 |

-continued

| Example number | Product name | LC-MS $t_R$ (min.), MH+, conditions |
|---|---|---|
| 117 | 2-(1-Ethyl-1H-indazol-5-yl)-N-[2-(4-fluoro-3-methoxy-benzyl)-2H-[1,2,3]triazol-4-yl]-acetamide | 1.27, 409.12, cond. 1 |
| 118 | 2-(1,3-Dimethyl-1H-indol-5-yl)-N-[2-(4-fluoro-3-methoxy-benzyl)-2H-[1,2,3]triazol-4-yl]-acetamide | 1.47, 408.12, cond.1 |
| 119 | 2-(4-tert-Butyl-phenyl)-N-[2-(4-fluoro-3-methoxy-benzyl)-2H-[1,2,3]triazol-4-yl]-acetamide | 1.66, 397.14, cond. 1 |
| 120 | N-[2-(3-Fluoro-4-methoxy-benzyl)-2H-[1,2,3]triazol-4-yl]-2-[4-(oxetan-3-ylmethoxy)-phenyl]-acetamide | 1.22, 427.12, cond. 1 |
| 121 | N-[2-(3-Fluoro-4-methoxy-benzyl)-2H-[1,2,3]triazol-4-yl]-2-(1-methyl-1H-indazol-6-yl)-acetamide | 1.19, 395.12, cond. 1 |
| 122 | N-[2-(3-Fluoro-4-methoxy-benzyl)-2H-[1,2,3]triazol-4-yl]-2-[4-(3-methoxy-oxetan-3-yl)-phenyl]-acetamide | 1.20, 427.14, cond. 1 |
| 123 | N-[2-(3-Fluoro-4-methoxy-benzyl)-2H-[1,2,3]triazol-4-yl]-2-[4-(3-methyl-oxetan-3-ylmethoxy)-phenyl]-acetamide | 1.32, 441.10, cond. 1 |
| 124 | N-[2-(3-Fluoro-4-methoxy-benzyl)-2H-[1,2,3]triazol-4-yl]-2-[4-(1-trifluoromethyl-cyclopropyl)-phenyl]-acetamide | 1.60, 449.11, cond. 1 |
| 125 | 2-[4-(3,3-Difluoro-cyclobutoxy)-phenyl]-N-[2-(3-fluoro-4-methoxy-benzyl)-2H-[1,2,3]triazol-4-yl]-acetamide | 1.50, 447.15, cond. 1 |
| 126 | 2-[6-(3,3-Difluoro-pyrrolidin-1-yl)-pyridin-3-yl]-N-[2-(3-fluoro-4-methoxy-benzyl)-2H-[1,2,3]triazol-4-yl]-acetamide | 1.31, 447.15, cond. 1 |
| 127 | N-[2-(3-Fluoro-4-methoxy-benzyl)-2H-[1,2,3]triazol-4-yl]-2-[4-(3-fluoro-oxetan-3-yl)-phenyl]-acetamide | 1.27, 415.11, cond. 1 |
| 128 | 2-(1-Ethyl-1H-indazol-5-yl)-N-[2-(3-fluoro-4-methoxy-benzyl)-2H-[1,2,3]triazol-4-yl]-acetamide | 1.25, 409.11, cond. 1 |
| 129 | 2-(1,3-Dimethyl-1H-indol-5-yl)-N-[2-(3-fluoro-4-methoxy-benzyl)-2H-[1,2,3]triazol-4-yl]-acetamide | 1.47, 408.12, cond. 1 |
| 130 | 2-(4-tert-Butyl-phenyl)-N-[2-(3-fluoro-4-methoxy-benzyl)-2H-[1,2,3]triazol-4-yl]-acetamide | 1.65, 397.16, cond. 1 |
| 131 | N-[2-(4-Cyano-3-fluoro-benzyl)-2H-[1,2,3]triazol-4-yl]-2-[4-(oxetan-3-ylmethoxy)-phenyl]-acetamide | 1.19, 421.88, cond. 1 |
| 132 | N-[2-(4-Cyano-3-fluoro-benzyl)-2H-[1,2,3]triazol-4-yl]-2-(1-methyl-1H-indazol-6-yl)-acetamide | 1.16, 389.70, cond. 1 |
| 133 | N-[2-(4-Cyano-3-fluoro-benzyl)-2H-[1,2,3]triazol-4-yl]-2-[4-(3-methoxy-oxetan-3-yl)-phenyl]-acetamide | 1.17, 439.0[(2)], cond. 1 |
| 134 | N-[2-(4-Cyano-3-fluoro-benzyl)-2H-[1,2,3]triazol-4-yl]-2-[4-(3,3-difluoro-cyclobutylmethoxy)-phenyl]-acetamide | 1.52, 473.1[(2)], cond. 1 |
| 135 | N-[2-(4-Cyano-3-fluoro-benzyl)-2H-[1,2,3]triazol-4-yl]-2-[4-(3-methyl-oxetan-3-ylmethoxy)-phenyl]-acetamide | 1.29, 453.13[(2)], cond. 1 |
| 136 | N-[2-(4-Cyano-3-fluoro-benzyl)-2H-[1,2,3]triazol-4-yl]-2-[4-(1-trifluoromethyl-cyclopropyl)-phenyl]-acetamide | 1.57, 461.1[(2)], cond. 1 |
| 137 | N-[2-(4-Cyano-3-fluoro-benzyl)-2H-[1,2,3]triazol-4-yl]-2-[4-(3,3-difluoro-cyclobutoxy)-phenyl]-acetamide | 1.47, 461.4[(2)], cond. 1 |
| 138 | N-[2-(4-Cyano-3-fluoro-benzyl)-2H-[1,2,3]triazol-4-yl]-2-[4-(3-fluoro-oxetan-3-yl)-phenyl]-acetamide | 1.24, 427.1[(2)], cond. 1 |
| 139 | N-[2-(4-Cyano-3-fluoro-benzyl)-2H-[1,2,3]triazol-4-yl]-2-(1-ethyl-1H-indazol-5-yl)-acetamide | 1.23, 404.09, cond. 1 |
| 140 | N-[2-(4-Cyano-3-fluoro-benzyl)-2H-[1,2,3]triazol-4-yl]-2-(1,3-dimethyl-1H-indol-5-yl)-acetamide | 1.44, 403.10, cond. 1 |
| 141 | N-[2-(3,5-Difluoro-4-methoxy-benzyl)-2H-[1,2,3]triazol-4-yl]-2-[4-(oxetan-3-ylmethoxy)-phenyl]-acetamide | 1.29, 445.13, cond. 1 |
| 142 | N-[2-(3,5-Difluoro-4-methoxy-benzyl)-2H-[1,2,3]triazol-4-yl]-2-(1-methyl-1H-indazol-6-yl)-acetamide | 1.26, 413.11, cond. 1 |
| 143 | N-[2-(3,5-Difluoro-4-methoxy-benzyl)-2H-[1,2,3]triazol-4-yl]-2-[4-(3-methoxy-oxetan-3-yl)-phenyl]-acetamide | 1.28, 445.12, cond. 1 |
| 144 | N-[2-(3,5-Difluoro-4-methoxy-benzyl)-2H-[1,2,3]triazol-4-yl]-2-[4-(3-methyl-oxetan-3-ylmethoxy)-phenyl]-acetamide | 1.40, 459.13, cond. 1 |
| 145 | N-[2-(3,5-Difluoro-4-methoxy-benzyl)-2H-[1,2,3]triazol-4-yl]-2-[4-(1-trifluoromethyl-cyclopropyl)-phenyl]-acetamide | 1.66, 467.09, cond. 1 |
| 146 | 2-[4-(3,3-Difluoro-cyclobutoxy)-phenyl]-N-[2-(3,5-difluoro4-methoxy-benzyl)-2H-[1,2,3]triazol-4-yl]-acetamide | 1.56, 465.08, cond. 1 |
| 147 | N-[2-(3,5-Difluoro-4-methoxy-benzyl)-2H-[1,2,3]triazol-4-yl]-2-[6-(3,3-difluoro-pyrrolidin-1-yl)-pyridin-3-yl]-acetamide | 1.38, 465.11, cond. 1 |
| 148 | N-[2-(3,5-Difluoro-4-methoxy-benzyl)-2H-[1,2,3]triazol-4-yl]-2-[4-(3-fluoro-oxetan-3-yl)-phenyl]-acetamide | 1.35, 433.12, cond. 1 |
| 149 | N-[2-(3,5-Difluoro-4-methoxy-benzyl)-2H-[1,2,3]triazol-4-yl]-2-(1-ethyl-1H-indazol-5-yl)-acetamide | 1.33, 427.12, cond. 1 |
| 150 | N-[2-(3,5-Difluoro-4-methoxy-benzyl)-2H-[1,2,3]triazol-4-yl]-2-(1,3-dimethyl-1H-indol-5-yl)-acetamide | 1.54, 426.10, cond. 1 |
| 151 | N-[2-(4-Fluoro-3-methoxy-benzyl)-2H-[1,2,3]triazol-4-yl]-2-(1-methyl-1H-indazol-5-yl)-acetamide | 1.18, 395.10, cond. 1 |
| 152 | N-[2-(3-Fluoro-4-methoxy-benzyl)-2H-[1,2,3]triazol-4-yl]-2-(1-methyl-1H-indazol-5-yl)-acetamide | 1.17, 395.12, cond. 1 |

-continued

| Example number | Product name | LC-MS $t_R$ (min.), MH+, conditions |
|---|---|---|
| 153 | N-[2-(4-Fluoro-3-methoxy-benzyl)-2H-[1,2,3]triazol-4-yl]-2-(4-isopropyl-phenyl)-acetamide | 1.59, 383.08, cond. 1 |
| 154 | N-[2-(3-Fluoro-4-methoxy-benzyl)-2H-[1,2,3]triazol-4-yl]-2-(4-isopropyl-phenyl)-acetamide | 1.58, 383.12, cond. 1 |
| 155 | N-[2-(4-Fluoro-3-methoxy-benzyl)-2H-[1,2,3]triazol-4-yl]-2-(6-pyrrolidin-1-yl-pyridin-3-yl)-acetamide | 1.29, 411.13, cond. 1 |
| 156 | N-[2-(3-Fluoro-4-methoxy-benzyl)-2H-[1,2,3]triazol-4-yl]-2-(6-pyrrolidin-1-yl-pyridin-3-yl)-acetamide | 1.28, 411.14, cond. 1 |
| 157 | 2-[4-(Cyano-dimethyl-methyl)-phenyl]-N-[2-(4-cyano-3-fluoro-benzyl)-2H-[1,2,3]triazol-4-yl]-acetamide | 0.87, 403.16, cond. 3 |
| 158 | 2-(4-tert-Butyl-phenyl)-N-[2-(4-cyano-3-fluoro-5-methoxy-benzyl)-2H-[1,2,3]triazol-4-yl]-acetamide | 0.96, 422.20, cond. 3 |
| 159 | N-[2-(4-Cyano-3-fluoro-benzyl)-2H-[1,2,3]triazol-4-yl]-2-(4-trifluoromethyl-phenyl)-acetamide | 0.90, 404.11, cond. 3 |
| 160 | N-[2-(4-Cyano-3-fluoro-benzyl)-2H-[1,2,3]triazol-4-yl]-2-[6-(3-methoxy-azetidin-1-yl)-pyridin-3-yl]-acetamide | 0.62, 422.15, cond. 3 |
| 161 | N-[2-(4-Cyano-3-fluoro-benzyl)-2H-[1,2,3]triazol-4-yl]-2-(5-fluoro-6-pyrrolidin-1-yl-pyridin-3-yl)-acetamide | 0.68, 424.18, cond. 3 |
| 162 | 2-(4-tert-Butyl-phenyl)-N-[2-(4-cyano-3-methyl-benzyl)-2H-[1,2,3]triazol-4-yl]-acetamide | 1.65, 388.12, cond. 1 |
| 163 | N-[2-(4-Cyano-3-methyl-benzyl)-2H-[1,2,3]triazol-4-yl]-2-(1-methyl-1H-indazol-6-yl)-acetamide | 1.20, 386.06, cond. 1 |
| 164 | N-[2-(4-Cyano-3-methyl-benzyl)-2H-[1,2,3]triazol-4-yl]-2-(1-methyl-1H-indazol-5-yl)-acetamide | 1.20, 386.10, cond. 1 |
| 165 | N-[2-(4-Cyano-3-methyl-benzyl)-2H-[1,2,3]triazol-4-yl]-2-(4-isopropyl-phenyl)-acetamide | 1.58, 373.82, cond. 1 |
| 166 | N-[2-(4-Cyano-3-methyl-benzyl)-2H-[1,2,3]triazol-4-yl]-2-[4-(3,3-difluoro-cyclobutoxy)-phenyl]-acetamide | 1.51, 437.80, cond. 1 |
| 167 | N-[2-(4-Cyano-3-methyl-benzyl)-2H-[1,2,3]triazol-4-yl]-2-[6-(3,3-difluoro-pyrrolidin-1-yl)-pyridin-3-yl]-acetamide | 1.22, 437.82, cond. 1 |
| 168 | N-[2-(4-Cyano-3-methyl-benzyl)-2H-[1,2,3]triazol-4-yl]-2-(1-ethyl-1H-indazol-5-yl)-acetamide | 1.27, 400.15, cond. 1 |
| 169 | N-[2-(4-Cyano-3-methyl-benzyl)-2H-[1,2,3]triazol-4-yl]-2-(1,3-dimethyl-1H-indazol-5-yl)-acetamide | 1.23, 400.12, cond. 1 |
| 170 | N-[2-(4-Cyano-3-methyl-benzyl)-2H-[1,2,3]triazol-4-yl]-2-(6-pyrrolidin-1-yl-pyridin-3-yl)-acetamide | 0.89, 402.17, cond. 1 |
| 171 | N-[2-(4-Cyano-3-methyl-benzyl)-2H-[1,2,3]triazol-4-yl]-2-(1,3-dimethyl-1H-indol-5-yl)-acetamide | 1.47, 399.15, cond. 1 |
| 172 | 2-(4-tert-Butyl-phenyl)-N-[2-(3-cyano-4-fluoro-benzyl)-2H-[1,2,3]triazol-4-yl]-acetamide | 1.63, 409.15[(2)], cond. 1 |
| 173 | N-[2-(3-Cyano-4-fluoro-benzyl)-2H-[1,2,3]triazol-4-yl]-2-(1-methyl-1H-indazol-5-yl)-acetamide | 1.16, 389.77, cond. 1 |
| 174 | N-[2-(3-Cyano-4-fluoro-benzyl)-2H-[1,2,3]triazol-4-yl]-2-(4-isopropyl-phenyl)-acetamide | 1.57, 378.03. cond. 1 |
| 175 | N-[2-(4-Cyano-3-fluoro-benzyl)-2H-[1,2,3]triazol-4-yl]-2-[4-(3-fluoro-oxetan-3-ylmethoxy)-phenyl]-acetamide | 1.28, 440.08, cond. 1 |
| 176 | N-[2-(4-Cyano-3-fluoro-benzyl)-2H-[1,2,3]triazol-4-yl]-2-[4-(3,3-difluoro-1-methyl-cyclobutylmethoxy)-phenyl]-acetamide | 1.63, 487.1[(2)], cond. 1 |
| 177 | N-[2-(4-Cyano-3-fluoro-benzyl)-2H-[1,2,3]triazol-4-yl]-2-(1,3-dimethyl-1H-indazol-5-yl)-acetamide | 1.20, 404.08, cond. 1 |
| 178 | 2-(4-tert-Butyl-phenyl)-N-[2-(4-difluoromethoxy-3-fluoro-benzyl)-2H-[1,2,3]triazol-4-yl]-acetamide | 1.72, 433.15, cond. 1 |
| 179 | N-[2-(4-Difluoromethoxy-3-fluoro-benzyl)-2H-[1,2,3]triazol-4-yl]-2-(1-methyl-1H-indazol-5-yl)-acetamide | 1.29, 431.06, cond. 1 |
| 180 | N-[2-(4-Difluoromethoxy-3-fluoro-benzyl)-2H-[1,2,3]triazol-4-yl]-2-(4-isopropyl-phenyl)-acetamide | 1.67, 419.13, cond. 1 |
| 181 | N-[2-(4-Difluoromethoxy-3-fluoro-benzyl)-2H-[1,2,3]triazol-4-yl]-2-[4-(1-trifluoromethyl-cyclopropyl)-phenyl]-acetamide | 1.69, 484.93, cond. 1 |
| 182 | N-[2-(4-Difluoromethoxy-3-fluoro-benzyl)-2H-[1,2,3]triazol-4-yl]-2-[6-(3,3-difluoro-pyrrolidin-1-yl)-pyridin-3-yl]-acetamide | 1.35, 483.09, cond. 1 |
| 183 | N-[2-(4-Difluoromethoxy-3-fluoro-benzyl)-2H-[1,2,3]triazol-4-yl]-2-(6-pyrrolidin-1-yl-pyridin-3-yl)-acetamide | 1.01, 447.19, cond. 1 |
| 184 | 2-(4-tert-Butyl-phenyl)-N-[2-(3-fluoro-4-trifluoromethoxy-benzyl)-2H-[1,2,3]triazol-4-yl]-acetamide | 1.86, 451.13, cond. 1 |
| 185 | N-[2-(3-Fluoro-4-trifluoromethoxy-benzyl)-2H-[1,2,3]triazol-4-yl]-2-(1-methyl-1H-indazol-6-yl)-acetamide | 1.45, 449.10, cond. 1 |
| 186 | N-[2-(3-Fluoro-4-trifluoromethoxy-benzyl)-2H-[1,2,3]triazol-4-yl]-2-(1-methyl-1H-indazol-5-yl)-acetamide | 1.43, 449.10, cond. 1 |
| 187 | N-[2-(3-Fluoro-4-trifluoromethoxy-benzyl)-2H-[1,2,3]triazol-4-yl]-2-(4-isopropyl-phenyl)-acetamide | 1.80, 437.13, cond. 1 |
| 188 | N-[2-(3-Fluoro-4-trifluoromethoxy-benzyl)-2H-[1,2,3]triazol-4-yl]-2-[4-(1-trifluoromethyl-cyclopropyl)-phenyl]-acetamide | 1.80, 502.98, cond. 1 |
| 189 | 2-[6-(3,3-Difluoro-pyrrolidin-1-yl)-pyridin-3-yl]-N-[2-(3-fluoro-4-trifluoromethoxy-benzyl)-2H-[1,2,3]triazol-4-yl]-acetamide | 1.50, 501.02, cond. 1 |

-continued

| Example number | Product name | LC-MS $t_R$ (min.), MH+, conditions |
|---|---|---|
| 190 | 2-(1-Ethyl-1H-indazol-5-yl)-N-[2-(3-fluoro-4-trifluoromethoxy-benzyl)-2H-[1,2,3]triazol-4-yl]-acetamide | 1.62, 463.14, cond. 1 |
| 191 | 2-(1,3-Dimethyl-1H-indazol-5-yl)-N-[2-(3-fluoro-4-trifluoromethoxy-benzyl)-2H-[1,2,3]triazol-4-yl]-acetamide | 1.47, 463.10, cond. 1 |
| 192 | N-[2-(3-Fluoro-4-trifluoromethoxy-benzyl)-2H-[1,2,3]triazol-4-yl]-2-(6-pyrrolidin-1-yl-pyridin-3-yl)-acetamide | 1.13, 465.13, cond. 1 |
| 193 | N-[2-(4-Cyano-benzyl)-2H-[1,2,3]triazol-4-yl]-2-[4-(3-methyl-oxetan-3-ylmethoxy)-phenyl]-acetamide | 1.26, 435.2[(2)], cond. 1 |
| 194 | N-[2-(4-Cyano-benzyl)-2H-[1,2,3]triazol-4-yl]-2-[4-(3-fluoro-oxetan-3-ylmethoxy)-phenyl]-acetamide | 1.22, 421.88, cond. 1 |
| 195 | N-[2-(4-Cyano-benzyl)-2H-[1,2,3]triazol-4-yl]-2-[4-(1-trifluoromethyl-cyclopropyl)-phenyl]-acetamide | 1.55, 426.04, cond. 1 |
| 196 | N-[2-(4-Cyano-benzyl)-2H-[1,2,3]triazol-4-yl]-2-[4-(3,3-difluoro-cyclobutoxy)-phenyl]-acetamide | 1.44, 424.26, cond. 1 |
| 197 | N-[2-(4-Cyano-benzyl)-2H-[1,2,3]triazol-4-yl]-2-[4-(3,3-difluoro-1-methyl-cyclobutylmethoxy)-phenyl]-acetamide | 1.59, 452.23, cond. 1 |
| 198 | N-[2-(4-Cyano-benzyl)-2H-[1,2,3]triazol-4-yl]-2-[4-(3-fluoro-oxetan-3-yl)-phenyl]-acetamide | 1.21, 392.15, cond. 1 |
| 199 | N-[2-(4-Cyano-3-fluoro-benzyl)-2H-[1,2,3]triazol-4-yl]-2-[3-methyl-4-(2,2,2-trifluoro-ethoxy)-phenyl]-acetamide | 0.93, 448.07, cond. 3 |
| 200 | N-[2-(3-Cyano-4-methyl-benzyl)-2H-[1,2,3]triazol-4-yl]-2-[4-(3-fluoro-oxetan-3-ylmethoxy)-phenyl]-acetamide | 1.03, 436.3, cond. 5 |
| 201 | N-[2-(3-Cyano-4-methyl-benzyl)-2H-[1,2,3]triazol-4-yl]-2-[4-(3-fluoro-oxetan-3-yl)-phenyl]-acetamide | 1.02, 406.3, cond. 5 |
| 202 | 2-(4-tert-Butyl-phenyl)-N-[2-(3-cyano-4-methoxy-benzyl)-2H-[1,2,3]triazol-4-yl]-acetamide | 1.23, 404.3, cond. 5 |
| 203 | N-[2-(3-Cyano-4-methoxy-benzyl)-2H-[1,2,3]triazol-4-yl]-2-[4-(1-trifluoromethyl-cyclopropyl)-phenyl]-acetamide | 1.19, 456.3, cond. 5 |
| 204 | N-[2-(3-Cyano-4-methyl-benzyl)-2H-[1,2,3]triazol-4-yl]-2-(1-methyl-1H-indazol-5-yl)-acetamide | 0.96, 386.3, cond. 5 |
| 205 | N-[2-(3-Cyano-4-methoxy-benzyl)-2H-[1,2,3]triazol-4-yl]-2-(4-isopropyl-phenyl)-acetamide | 1.18, 390.3, cond. 5 |
| 206 | N-[2-(3-Cyano-4-methoxy-benzyl)-2H-[1,2,3]triazol-4-yl]-2-[4-(3-methoxy-oxetan-3-yl)-phenyl]-acetamide | 0.98, 418.3, cond. 5 |
| 207 | N-[2-(3-Cyano-4-methoxy-benzyl)-2H-[1,2,3]triazol-4-yl]-2-[6-(3,3-difluoro-pyrrolidin-1-yl)-pyridin-3-yl]-acetamide | 0.71, 454.3, cond. 5 |
| 208 | N-[2-(3-Cyano-4-methoxy-benzyl)-2H-[1,2,3]triazol-4-yl]-2-(1-methyl-1H-indazol-5-yl)-acetamide | 0.92, 402.3, cond. 5 |
| 209 | N-[2-(3-Cyano-4-methyl-benzyl)-2H-[1,2,3]triazol-4-yl]-2-[4-(3,3-difluoro-cyclobutoxy)-phenyl]-acetamide | 1.16, 438.3, cond. 5 |
| 210 | N-[2-(3,4-Difluoro-5-methoxy-benzyl)-2H-[1,2,3]triazol-4-yl]-2-(1,3-dimethyl-1H-indazol-5-yl)-acetamide | 1.05, 427.3, cond. 5 |
| 211 | N-[2-(3-Cyano-4-methyl-benzyl)-2H-[1,2,3]triazol-4-yl]-2-[6-(3,3-difluoro-pyrrolidin-1-yl)-pyridin-3-yl]-acetamide | 0.76, 438.3, cond. 5 |
| 212 | N-[2-(3,4-Difluoro-5-methoxy-benzyl)-2H-[1,2,3]triazol-4-yl]-2-(1-methyl-1H-indazol-5-yl)-acetamide | 1.03, 413.3, cond. 5 |
| 213 | N-[2-(3-Cyano-4-methyl-benzyl)-2H-[1,2,3]triazol-4-yl]-2-(6-pyrrolidin-1-yl-pyridin-3-yl)-acetamide | 0.61, 402.3, cond. 5 |
| 214 | N-[2-(3-Cyano-4-methoxy-benzyl)-2H-[1,2,3]triazol-4-yl]-2-[4-(3-fluoro-oxetan-3-yl)-phenyl]-acetamide | 0.98, 422.3, cond. 5 |
| 215 | N-[2-(3-Cyano-4-methyl-benzyl)-2H-[1,2,3]triazol-4-yl]-2-(1-methyl-1H-indazol-6-yl)-acetamide | 0.97, 386.3, cond. 5 |
| 216 | N-[2-(3-Cyano-4-methyl-benzyl)-2H-[1,2,3]triazol-4-yl]-2-(4-isopropyl-phenyl)-acetamide | 1.23, 374.3, cond. 5 |
| 217 | 2-(4-tert-Butyl-phenyl)-N-[2-(3-cyano-4-methyl-benzyl)-2H-[1,2,3]triazol-4-yl]-acetamide | 1.60, 388.0, cond. 1 |
| 218 | 2-(4-tert-Butyl-phenyl)-N-[2-(3,4-difluoro-5-methoxy-benzyl)-2H-[1,2,3]triazol-4-yl]-acetamide | 1.32, 415.3, cond. 5 |
| 219 | N-[2-(3,4-Difluoro-5-methoxy-benzyl)-2H-[1,2,3]triazol-4-yl]-2-[6-(3,3-difluoro-pyrrolidin-1-yl)-pyridin-3-yl]-acetamide | 0.82, 465.3, cond. 5 |
| 220 | N-[2-(3,4-Difluoro-5-methoxy-benzyl)-2H-[1,2,3]triazol-4-yl]-2-(1-ethyl-1H-indazol-5-yl)-acetamide | 1.30, 427.2, cond. 1 |
| 221 | N-[2-(3,4-Difluoro-5-methoxy-benzyl)-2H-[1,2,3]triazol-4-yl]-2-(6-pyrrolidin-1-yl-pyridin-3-yl)-acetamide | 0.65, 429.3, cond. 5 |
| 222 | N-[2-(3,4-Difluoro-5-methoxy-benzyl)-2H-[1,2,3]triazol-4-yl]-2-(4-isopropyl-phenyl)-acetamide | 1.28, 401.3, cond. 5 |
| 223 | N-[2-(3-Cyano-4-methoxy-benzyl)-2H-[1,2,3]triazol-4-yl]-2-[4-(3,3-difluoro-cyclobutoxy)-phenyl]-acetamide | 1.12, 454.3, cond. 5 |
| 224 | N-[2-(3,4-Difluoro-5-methoxy-benzyl)-2H-[1,2,3]triazol-4-yl]-2-[4-(3-fluoro-oxetan-3-yl)-phenyl]-acetamide | 1.07, 433.3, cond. 5 |
| 225 | N-[2-(3,4-Difluoro-5-methoxy-benzyl)-2H-[1,2,3]triazol-4-yl]-2-(1-methyl-1H-indazol-6-yl)-acetamide | 1.03, 413.3, cond. 5 |
| 226 | N-[2-(3-Cyano-4-methyl-benzyl)-2H-[1,2,3]triazol-4-yl]-2-[4-(1-trifluoromethyl-cyclopropyl)-phenyl]-acetamide | 1.56, 440.1, cond. 1 |

| Example number | Product name | LC-MS $t_R$ (min.), MH$^+$, conditions |
|---|---|---|
| 227 | N-[2-(3,4-Difluoro-5-methoxy-benzyl)-2H-[1,2,3]triazol-4-yl]-2-[4-(1-trifluoromethyl-cyclopropyl)-phenyl]-acetamide | 1.27, 467.3, cond. 5 |
| 228 | N-[2-(3,4-Difluoro-5-methoxy-benzyl)-2H-[1,2,3]triazol-4-yl]-2-[4-(3-methoxy-oxetan-3-yl)-phenyl]-acetamide | 1.04, 445.3, cond. 3 |
| 229 | N-[2-(3,4-Difluoro-5-methoxy-benzyl)-2H-[1,2,3]triazol-4-yl]-2-[4-(3-fluoro-oxetan-3-ylmethoxy)-phenyl]-acetamide | 1.08, 463.3, cond. 5 |
| 230 | 2-[4-(3,3-Difluoro-cyclobutoxy)-phenyl]-N-[2-(3,4-difluoro-5-methoxy-benzyl)-2H-[1,2,3]triazol-4-yl]-acetamide | 1.20, 465.3, cond. 5 |
| 231 | 2-[4-(1-Cyano-cyclopropyl)-phenyl]-N-[2-(4-cyano-3-fluoro-benzyl)-2H-[1,2,3]triazol-4-yl]-acetamide | 1.03, 401.3, cond. 5 |
| 232 | N-(2-(4-cyano-3-fluorobenzyl)-2H-1,2,3-triazol-4-yl)-2-(4-(pentafluoro-λ6-sulfanyl)phenyl)acetamide | 1.19, 462.2, cond. 5 |
| 233 | N-[2-(4-Cyano-3-methoxy-benzyl)-2H-[1,2,3]triazol-4-yl]-2-[4-(1-trifluoromethyl-cyclopropyl)-phenyl]-acetamide | 1.56, 473.1$^{(2)}$, cond. 1 |
| 234 | N-[2-(4-Cyano-benzyl)-2H-[1,2,3]triazol-4-yl]-2-(1-methyl-1H-indazol-5-yl)-acetamide | 0.90, 372.3, cond. 5 |
| 235 | N-[2-(4-Cyano-3-methyl-benzyl)-2H-[1,2,3]triazol-4-yl]-2-[4-(3-fluoro-oxetan-3-yl)-phenyl]-acetamide | 1.01, 406.3, cond. 5 |
| 236 | N-[2-(3-Cyano-4-methoxy-benzyl)-2H-[1,2,3]triazol-4-yl]-2-(6-pyrrolidin-1-yl-pyridin-3-yl)-acetamide | 0.58, 418.3, cond. 5 |
| 237 | N-[2-(4-Cyano-benzyl)-2H-[1,2,3]triazol-4-yl]-2-[4-(3-methoxy-oxetan-3-yl)-phenyl]-acetamide | 1.07, 404.0, cond. 1 |
| 238 | N-[2-(4-Cyano-benzyl)-2H-[1,2,3]triazol-4-yl]-2-[4-(3,3-difluoro-cyclobutylmethoxy)-phenyl]-acetamide | 1.15, 438.3, cond. 5 |
| 239 | 2-(4-tert-Butyl-phenyl)-N-[2-(4-cyano-3-methoxy-benzyl)-2H-[1,2,3]triazol-4-yl]-acetamide | 1.29, 404.3, cond. 5 |
| 240 | N-[2-(3,4-Difluoro-5-methoxy-benzyl)-2H-[1,2,3]triazol-4-yl]-2-(1,3-dimethyl-1H-indol-5-yl)-acetamide | 1.20, 426.3, cond. 5 |
| 241 | N-[2-(4-Cyano-3-methyl-benzyl)-2H-[1,2,3]triazol-4-yl]-2-[4-(1-trifluoromethyl-cyclopropyl)-phenyl]-acetamide | 1.55, 457.2$^{(2)}$, cond. 1 |
| 242 | N-[2-(5-Cyano-pyridin-2-ylmethyl)-2H-[1,2,3]triazol-4-yl]-2-[3-methyl-4-(2,2,2-trifluoro-ethoxy)-phenyl]-acetamide | 1.08, 431.3, cond. 5 |
| 243 | N-[2-(5-Cyano-pyridin-2-ylmethyl)-2H-[1,2,3]triazol-4-yl]-2-(1,3-dimethyl-1H-indol-5-yl)-acetamide | 1.02, 386.3, cond. 5 |
| 244 | 2-(4-tert-Butyl-phenyl)-N-[2-(5-cyano-pyridin-2-ylmethyl)-2H-[1,2,3]triazol-4-yl]-acetamide | 1.15, 375.3, cond. 5 |
| 245 | N-[2-(5-Cyano-pyridin-2-ylmethyl)-2H-[1,2,3]triazol-4-yl]-2-[4-(1-trifluoromethyl-cyclopropyl)-phenyl]-acetamide | 1.11, 427.3, cond. 5 |
| 246 | N-[2-(5-Cyano-pyridin-2-ylmethyl)-2H-[1,2,3]triazol-4-yl]-2-[4-(3,3-difluoro-cyclobutoxy)-phenyl]-acetamide | 1.03, 425.3, cond. 5 |
| 247 | N-[2-(5-Cyano-pyridin-2-ylmethyl)-2H-[1,2,3]triazol-4-yl]-2-(5-fluoro-6-pyrrolidin-1-yl-pyridin-3-yl)-acetamide | 0.70, 407.3, cond. 5 |
| 249 | N-[2-(4-Cyano-3-fluoro-benzyl)-2H-[1,2,3]triazol-4-yl]-2-[4-(2,2,2-trifluoro-1,1-dimethyl-ethyl)-phenyl]-acetamide | 1.22, 446.3, cond. 5 |
| 250 | rac-N-[2-(4-Cyano-3-fluoro-benzyl)-2H-[1,2,3]triazol-4-yl]-2-[4-((1S*,2S*)-2-trifluoromethyl-cyclopropyl)-phenyl]-acetamide | 1.21, 444.3, cond. 5 |

$^{(1)}$CH$_3$CN-adduct;
$^{(2)}$NH$_3$-adduct

In Vitro Methods—Measurement of Calcium Channel Flux by Means of FLIPR Assays.

HEK293 cells recombinantly expressing either voltage-dependent T-type calcium channel subunit alpha-1G (Cav3.2) or voltage-dependent L-type calcium channel subunit alpha-1C (Cav1.2) are assayed for calcium flux using the calcium indicator dye Fluo-4-AM (Molecular Devices) and FLIPR technology (Fluorometric Imaging Plate Reader, Molecular Devices) (Xie X, Van Deusen A L, Vitko I, Babu D A, Davies L A, Huynh N, Cheng H, Yang N, Barrett P Q, Perez-Reyes E. Validation of high throughput screening assays against three subtypes of Ca(v)3 T-type channels using molecular and pharmacologic approaches. Assay and Drug Development Technologies 2007, 5(2), 191-203). The HEK293 cells recombinantly expressing Cav3.2 are maintained in DMEM growth medium (Life Technologies) supplemented with 10% Fetal Bovine Serum (FBS), 100 U/ml penicilin (Life Technologies), 100 µg/ml streptomycin (Life Technologies) and 1 mg/ml G418 (Life Technologies). HEK293 cells recombinantly expressing Cav1.2 are maintained in DMEM growth medium (Life technologies) supplemented with 10% FBS, 0.1 mg/ml G418 (Life Technologies), 0.1 mg/ml hygromycin (Life Technologies) and 40 ug/ml zeocin (Life Technologies).

Cells are washed once with PBS, then dissociated in 0.25% trypsin/EDTA (Life Technologies) and seeded into poly-D-lysine coated 384-well black, clear bottom plates (BD Biosciences) at a density of 30,000 cells/well. The seeded plates are incubated overnight at 37° C.

Immediately prior to performing the assay, medium is removed and cells are treated for 1 hour at 37° C. with loading buffer containing HBSS 1× (137 mM NaCl; 5.4 mM KCl; 0.25 mM Na2HPO4; 1.3 mM CaCl2; 0.4 mM MgSO04; 0.5 mM MgCl2; 0.4 mM KH2PO4, pH 7.4), 0.375 g/L NaHCO3, 20 mM Hepes, supplemented with 3 µM Fluo-4-AM and 0.15% Pluronic (Life Technologies). The cells are then washed three times with assay buffer (HBSS 1×; 0.375 g/L NaHCO3; 20 mM Hepes; 1% FBS; pH 7.4) and allowed to rest in 50 µl of wash buffer for 30 minutes.

Stock solutions of test compounds are prepared to a concentration of 10 mM in DMSO. For the Cav3.2 assay, serial dilutions of the compounds are prepared in TEAC buffer (100 mM tetraethylammonium chloride; 20 mM Hepes; 2.5 mM CaCl2; 5 mM KCl; 1 mM MgCl2; 1% FBS; pH 7.2), for the Cav1.2 assay serial dilutions are prepared in assay buffer. Test compounds are added to the cells to give a 3-fold dilution range from 10 μM to 0.05 nM. The compounds are incubated with the cells for 3 minutes and Ca2+ entry is stimulated by adding either CaCl2 to a final concentration of 10 mM (Cav3.2 assay) or by adding KCl to a final concentration of 20 mM (Cav1.2 assay). The kinetics of fluorescence increase are recorded for every well and the area under the fluorescence trace for every compound concentration is used to generate inhibition curves using non-linear regression sigmoidal concentration-response curve analysis with in-house software. $IC_{50}$ values are calculated and represent the compound concentration required to inhibit 50% of the signal that is obtained in the presence of vehicle instead of test compound. In analogy, antagonistic activities ($IC_{50}$ values) of all exemplified compounds have been measured for the for the Cav3.1- and the Cav3.3- channel. Antagonistic activities ($IC_{50}$ values) of all exemplified compounds are in the range of 1.7 to 970 nM with respect to Cav3.1; and in the range of 1.1 to 620 nM with respect to Cav3.3.

In the following table, $IC_{50}$-values generated for the Cav3.2-channel are presented.

| Example | IC50 (nM) |
| --- | --- |
| 1 | 21 |
| 2 | 17 |
| 5 | 30 |
| 6 | 9.5 |
| 7 | 6.4 |
| 8 | 37 |
| 9 | 22 |
| 10 | 23 |
| 11 | 32 |
| 12 | 31 |
| 13 | 27 |
| 14 | 17 |
| 15 | 40 |
| 16 | 15 |
| 17 | 7.3 |
| 18 | 15 |
| 19 | 9.7 |
| 20 | 89 |
| 21 | 180 |
| 22 | 15 |
| 23 | 46 |
| 24 | 37 |
| 25 | 33 |
| 26 | 19 |
| 27 | 9.8 |
| 28 | 22 |
| 29 | 120 |
| 30 | 17 |
| 31 | 11 |
| 32 | 74 |
| 33 | 24 |
| 34 | 18 |
| 35 | 29 |
| 38 | 580 |
| 39 | 280 |
| 40 | 35 |
| 41 | 18 |
| 42 | 31 |
| 43 | 45 |
| 44 | 40 |
| 45 | 32 |
| 46 | 63 |
| 47 | 560 |
| 48 | 530 |
| 49 | 170 |
| 50 | 160 |
| 51 | 600 |
| 52 | 12 |
| 53 | 35 |
| 54 | 26 |
| 55 | 50 |
| 56 | 38 |
| 57 | 38 |
| 58 | 160 |
| 59 | 60 |
| 60 | 120 |
| 61 | 44 |
| 62 | 120 |
| 63 | 160 |
| 64 | 30 |
| 65 | 23 |
| 66 | 70 |
| 67 | 66 |
| 68 | 45 |
| 69 | 20 |
| 70 | 18 |
| 71 | 75 |
| 72 | 74 |
| 73 | 37 |
| 74 | 45 |
| 75 | 87 |
| 76 | 120 |
| 77 | 13 |
| 78 | 49 |
| 79 | 46 |
| 80 | 29 |
| 81 | 28 |
| 82 | 23 |
| 86 | 130 |
| 87 | 460 |
| 88 | 56 |
| 89 | 20 |
| 90 | 200 |
| 91 | 7.4 |
| 92 | 9.9 |
| 93 | 15 |
| 94 | 10 |
| 95 | 46 |
| 96 | 44 |
| 97 | 36 |
| 98 | 83 |
| 99 | 19 |
| 100 | 22 |
| 101 | 480 |
| 102 | 160 |
| 103 | 74 |
| 104 | 70 |
| 105 | 20 |
| 106 | 36 |
| 108 | 300 |
| 109 | 190 |
| 110 | 140 |
| 111 | 57 |
| 112 | 190 |
| 113 | 230 |
| 114 | 73 |
| 115 | 45 |
| 116 | 140 |
| 117 | 80 |
| 118 | 63 |
| 119 | 62 |
| 120 | 550 |
| 121 | 290 |
| 122 | 360 |
| 123 | 870 |
| 124 | 250 |
| 125 | 180 |
| 126 | 47 |
| 127 | 110 |
| 128 | 150 |
| 129 | 48 |
| 130 | 62 |
| 131 | 210 |

-continued

| Example | IC50 (nM) |
|---|---|
| 132 | 180 |
| 133 | 130 |
| 134 | 110 |
| 135 | 120 |
| 136 | 79 |
| 137 | 37 |
| 138 | 78 |
| 139 | 69 |
| 140 | 14 |
| 141 | 86 |
| 142 | 88 |
| 143 | 76 |
| 144 | 56 |
| 145 | 120 |
| 146 | 810 |
| 147 | 13 |
| 148 | 35 |
| 149 | 29 |
| 150 | 16 |
| 151 | 73 |
| 152 | 91 |
| 153 | 70 |
| 154 | 44 |
| 155 | 140 |
| 156 | 70 |
| 157 | 31 |
| 158 | 240 |
| 159 | 61 |
| 161 | 25 |
| 162 | 36 |
| 163 | 330 |
| 164 | 110 |
| 165 | 18 |
| 166 | 33 |
| 167 | 22 |
| 168 | 40 |
| 169 | 96 |
| 170 | 50 |
| 171 | 22 |
| 172 | 33 |
| 173 | 150 |
| 174 | 28 |
| 175 | 100 |
| 176 | 64 |
| 177 | 33 |
| 178 | 49 |
| 179 | 22 |
| 180 | 43 |
| 181 | 86 |
| 182 | 13 |
| 183 | 26 |
| 184 | 83 |
| 185 | 17 |
| 186 | 8.8 |
| 187 | 65 |
| 188 | 96 |
| 189 | 17 |
| 190 | 14 |
| 191 | 11 |
| 192 | 23 |
| 193 | 110 |
| 194 | 340 |
| 195 | 63 |
| 196 | 41 |
| 197 | 52 |
| 198 | 130 |
| 199 | 17 |
| 200 | 410 |
| 201 | 310 |
| 202 | 320 |
| 203 | 220 |
| 204 | 280 |
| 205 | 160 |
| 206 | 900 |
| 207 | 130 |
| 208 | 600 |
| 209 | 180 |

-continued

| Example | IC50 (nM) |
|---|---|
| 210 | 260 |
| 211 | 82 |
| 212 | 230 |
| 213 | 120 |
| 214 | 250 |
| 215 | 650 |
| 216 | 74 |
| 217 | 160 |
| 218 | 590 |
| 219 | 120 |
| 220 | 190 |
| 221 | 160 |
| 222 | 300 |
| 223 | 120 |
| 224 | 190 |
| 225 | 560 |
| 226 | 250 |
| 227 | 770 |
| 228 | 300 |
| 229 | 130 |
| 230 | 350 |
| 231 | 36 |
| 232 | 110 |
| 233 | 110 |
| 234 | 76 |
| 235 | 92 |
| 236 | 160 |
| 237 | 200 |
| 238 | 24 |
| 239 | 210 |
| 240 | 180 |
| 241 | 110 |
| 242 | 54 |
| 243 | 110 |
| 244 | 34 |
| 245 | 190 |
| 246 | 680 |
| 247 | 690 |
| 249 | 91 |
| 250 | 29 |

The invention claimed is:
1. A compound of formula (I)

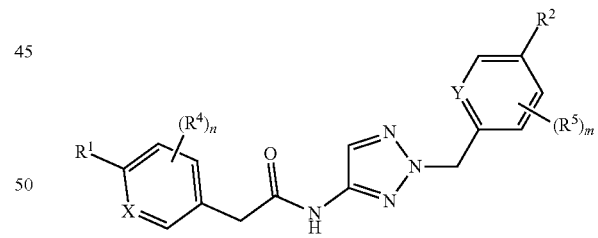

Formula (I)

wherein
X represents a ring carbon or a ring nitrogen atom;
R$^1$ represents
  ($C_{2-6}$)alkyl;
  ($C_{2-4}$)alkyl mono-substituted with cyano, or ($C_{1-3}$)alkoxy;
  ($C_{1-4}$)fluoroalkyl;
  ($C_{1-3}$)fluoroalkoxy;
  pentafluoro-sulfanyl;
  ($C_{3-6}$)cycloalkyl-L$^1$- wherein
    said ($C_{3-6}$)cycloalkyl optionally contains one ring oxygen atom; wherein said ($C_{3-6}$)cycloalkyl is unsubstituted; or mono-substituted with fluoro, ($C_{1-3}$)alkyl, ($C_{1-3}$)alkoxy, hydroxy, cyano, or ($C_{1-3}$)fluoroalkyl; or di-substituted with fluoro, or tri-substituted with two fluoro substituents and a ($C_{1-3}$)alkyl substituent; and the linker $L^1$ represents a direct bond, ($C_{1-2}$) alkylene, oxygen, or ($C_{1-2}$)alkylene-oxy;

5- or 6-membered heteroaryl, independently optionally mono-substituted with ($C_{1-3}$)alkyl;

—$NR^{11}R^{12}$, wherein $R^{11}$ and $R^{12}$ independently represent hydrogen, ($C_{1-3}$)alkyl, ($C_{2-3}$)fluoroalkyl, ($C_{3-6}$)cycloalkyl, ($C_{3-6}$)cycloalkyl mono- or di-substituted with fluoro, ($C_{3-6}$)cycloalkyl-($C_{1-3}$)alkyl, ($C_{1-3}$)alkoxy-($C_{2-3}$)alkyl;

or $R^{11}$ and $R^{12}$, together with the nitrogen atom to which they are attached to, form a 4- to -6 membered ring which is optionally mono- or di-substituted with fluoro; a 2-oxo-pyrrolidinyl group; or a morpholinyl group;

and $(R^4)_n$ represents one or two optional substituents independently selected from ($C_{1-4}$)alkyl, ($C_{1-4}$)alkoxy, ($C_{1-3}$)fluoroalkyl, ($C_{1-3}$)fluoroalkoxy, halogen, and cyano;

or $R^1$ together with $(R^4)_n$ forms a non-aromatic 5- or 6-membered ring which is fused to the phenyl/pyridine ring; wherein said 5- or 6-membered ring optionally contains one or two heteroatoms independently selected from oxygen and nitrogen; wherein said fused 5- or 6-membered non-aromatic ring independently is optionally further mono-substituted with oxo; or di-, tri-, or tetra-substituted wherein one substituent is oxo and the remaining are ($C_{1-3}$)alkyl;

or $R^1$ together with $(R^4)_n$ forms an aromatic 5- or 6-membered ring which is fused to the phenyl/pyridine ring; wherein said 5- or 6-membered ring optionally contains one or two nitrogen atoms, wherein said fused 5- or 6-membered aromatic ring independently is optionally further mono- or di-substituted wherein the substituents are independently selected from ($C_{1-4}$)alkyl, ($C_{3-6}$)cycloalkyl, ($C_1$)fluoroalkyl, or cyano;

Y represents a ring carbon or a ring nitrogen atom; and $R^2$ represents ($C_{1-4}$)alkyl; ($C_{3-6}$)cycloalkyl; ($C_{1-4}$)alkoxy; ($C_{3-6}$)cycloalkyl-oxy; ($C_{1-3}$)fluoroalkyl; ($C_{1-3}$)fluoroalkoxy; ($C_{1-3}$)alkoxy-($C_{2-3}$)alkoxy; halogen; cyano; or —$NR^{21}R^{22}$, wherein $R^{21}$ and $R^{22}$ independently represent hydrogen, or ($C_{1-3}$)alkyl, or $R^{21}$ and $R^{22}$, together with the nitrogen atom to which they are attached to, form a 4- to -6 membered ring optionally mono- or di-substituted with fluoro, or a morpholinyl group; and $(R^5)_m$ represents one or two optional substituents independently selected from ($C_{1-4}$)alkyl; ($C_{3-6}$)cycloalkyl; ($C_{1-4}$)alkoxy; halogen; cyano; ($C_{1-3}$)fluoroalkyl; and ($C_{1-3}$)fluoroalkoxy;

or a salt of such a compound.

2. A compound according to claim 1, wherein X represents a ring carbon atom; or a salt of such a compound.

3. A compound according to claim 1, wherein $R^1$ represents ($C_{2-6}$)alkyl;

($C_{2-4}$)alkyl mono-substituted with cyano, or ($C_{1-3}$)alkoxy;

($C_{1-4}$)fluoroalkyl;

($C_{1-3}$)fluoroalkoxy;

pentafluoro-sulfanyl;

($C_{3-6}$)cycloalkyl-$L^1$- wherein said ($C_{3-6}$)cycloalkyl optionally contains one ring oxygen atom; wherein said ($C_{3-6}$)cycloalkyl is unsubstituted, or mono-substituted with fluoro, ($C_{1-3}$)alkyl, ($C_{1-3}$)alkoxy, hydroxy, cyano, or ($C_{1-3}$)fluoroalkyl, or di-substituted with fluoro, or tri-substituted with two fluoro substituents and a ($C_{1-3}$)alkyl substituent; and the linker $L^1$ represents a direct bond, ($C_{1-2}$)alkylene, oxygen, or ($C_{1-2}$)alkylene-oxy;

—$NR^{11}R^{12}$, wherein $R^{11}$ and $R^{12}$ independently represent hydrogen, ($C_{1-3}$)alkyl, ($C_{2-3}$)fluoroalkyl, ($C_{3-6}$)cycloalkyl, ($C_{3-6}$)cycloalkyl mono- or di-substituted with fluoro, ($C_{3-6}$)cycloalkyl-($C_{1-3}$)alkyl;

or $R^{11}$ and $R^{12}$, together with the nitrogen atom to which they are attached to, form an azetidinyl or a pyrrolidinyl ring, both independently optionally mono- or di-substituted with fluoro;

and $(R^4)_n$ represents one optional substituent selected from ($C_{1-4}$)alkyl, ($C_{1-4}$)alkoxy, ($C_{1-3}$)fluoroalkyl, ($C_{1-3}$)fluoroalkoxy, halogen, and cyano;

or $R^1$ together with $(R^4)_n$ forms a non-aromatic 5- or 6-membered ring which is fused to the phenyl/pyridine ring to form a bicyclic ring system; wherein said bicyclic ring system is selected from 2,3-dihydro-benzooxazolyl, 3,4-dihydro-2H-benzo[1,4]oxazinyl, 2,3-dihydro-1H-indolyl, and 2,3-dihydro-benzofuranyl; wherein said non-aromatic 5- or 6-membered ring part of said bicyclic ring system independently is optionally further mono-substituted with oxo; or di-, tri-, or tetra-substituted wherein one substituent is oxo and the remaining are ($C_{1-3}$)alkyl;

or $R^1$ together with $(R^4)_n$ forms an aromatic 5- or 6-membered ring which is fused to the phenyl/pyridine ring to form a bicyclic aromatic ring system selected from pyrazolo[3,4-b]pyridinyl, pyrrolo[2,3-b]pyridinyl, indolyl, indazolyl, quinoxalinyl, benzoimidazolyl, and quinolinyl; wherein said fused 5- or 6-membered aromatic ring part of said aromatic bicyclic ring system independently is optionally further mono- or di-substituted wherein the substituents are independently selected from ($C_{1-3}$)alkyl, ($C_{3-6}$)cycloalkyl, ($C_1$)fluoroalkyl, or cyano;

or a salt of such a compound.

4. A compound according to claim 1, wherein $R^1$ represents ($C_{2-6}$)alkyl;

($C_{1-4}$)fluoroalkyl;

($C_{1-3}$)fluoroalkoxy;

($C_{3-6}$)cycloalkyl wherein said ($C_{3-6}$)cycloalkyl optionally contains one ring oxygen atom; wherein said ($C_{3-6}$)cycloalkyl is mono-substituted with fluoro or ($C_{1-3}$)fluoroalkyl, or di-substituted with fluoro; or ($C_{3-6}$)cycloalkyl-oxy- wherein said ($C_{3-6}$)cycloalkyl optionally contains one ring oxygen atom; wherein said ($C_{3-6}$)cycloalkyl is unsubstituted, or di-substituted with fluoro;

and $(R^4)_n$ represents one optional substituent selected from ($C_{1-4}$)alkyl, or halogen;

or a salt of such a compound.

5. A compound according to claim 1, wherein the fragment

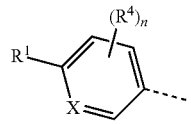

represents 4-isopropyl-phenyl, 4-dimethylamino-phenyl, 4-trifluoromethyl-phenyl, 4-tert.-butyl-phenyl, 4-(1-methoxy-ethyl)-phenyl, 4-(cyclopropyl-oxy)-phenyl, 4-(oxetan-3-yl)-phenyl, 4-(3-fluoro-oxetan-3-yl)-phenyl, 4-(cyclobutyl-oxy)-phenyl, 4-(3-methyl-oxetan-3-yl)-phenyl, 4-(1-cyano-cyclopropyl)-phenyl, 4-(1-cyano-1-methyl-ethyl)-phenyl, 4-(pentafluoro-sulfanyl)-phenyl, 3-methyl-4-(2,2,2-trifluoroethoxy)-phenyl, 4-(3-methoxy-oxetan-3-yl)-phenyl, 4-(oxetan-3-yl-methoxy)-phenyl, 4-(2-trifluoromethyl-cyclopropyl)-phenyl, 4-(1-trifluoromethyl-cyclopropyl)-phenyl, 4-((3-fluoro-oxetan-3-yl)-methoxy)-phenyl, 4-((3-methyl-oxetan-3-yl)-methoxy)-phenyl, 4-(3,3-difluoro-cyclobutyl-oxy)-phenyl, 4-(2,2,2-trifluoro-1,1-dimethyl-ethyl)-phenyl, 4-((3,3-difluoro-cyclobutyl)-methoxy)-phenyl, 4-((3,3-difluoro-1-methyl-cyclobutyl)-methoxy)-phenyl; 2-(pyrrolidin-1-yl)-pyridin-5-yl, 2-(cyclopropyl(methyl)amino)-pyridin-5-yl, 2-(diethylamino)-pyridin-5-yl, 3-fluoro-2-(pyrrolidin-1-yl)-pyridin-5-yl, 2-((cyclopropylmethyl)-methyl-amino)-pyridin-5-yl, 2-(3,3-difluoro-pyrrolidin-1-yl)-pyridin-5-yl; 3,3-dimethyl-2-oxo-2,3-dihydro-1H-indol-5-yl, 1,3,3-trimethyl-2-oxo-2,3-dihydro-1H-indol-5-yl, 1-methyl-1H-pyrazolo[3,4-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1,3-dimethyl-1H-indazol-5-yl, 1-propyl-1H-indazol-5-yl, 1-isopropyl-1H-indazol-5-yl, 1-butyl-1H-indazol-5-yl, 3-butyl-1H-indazol-5-yl, 3-trifluoromethyl-1H-indazol-5-yl, 3-cyclopropyl-1H-indazol-5-yl, 3-cyclopropyl-1-methyl-1H-indazol-5-yl, 1-methyl-1H-indol-5-yl, 2-methyl-1H-indol-5-yl, 1,3-dimethyl-1H-indol-5-yl, or 1,3-dimethyl-1H-indol-6-yl;

or a salt of such a compound.

6. A compound according to claim 1, wherein
Y represents a ring carbon or a nitrogen atom;
$R^2$ represents $(C_{1-4})$alkyl; $(C_{1-4})$alkoxy; $(C_{1-3})$fluoroalkyl; $(C_{1-3})$fluoroalkoxy; $(C_{1-3})$alkoxy-$(C_{2-3})$alkoxy; halogen; or cyano; and
$(R^5)_m$ represents one or two optional substituents independently selected from $(C_{1-4})$alkyl; $(C_{1-4})$alkoxy; halogen; cyano; $(C_{1-3})$fluoroalkyl; and $(C_{1-3})$fluoroalkoxy;

or a salt of such a compound.

7. A compound according to claim 1, wherein
Y represents a ring nitrogen atom; and
$R^2$ represents cyano; and
$(R^5)_m$ is absent; or
Y represents a ring carbon atom; and
$R^2$ represents $(C_{1-4})$alkyl; $(C_{1-4})$alkoxy; $(C_{1-3})$fluoroalkoxy; $(C_{1-3})$alkoxy-$(C_{2-3})$alkoxy; halogen; or cyano; and
$(R^5)_m$ represents one or two optional substituents independently selected from $(C_{1-4})$alkyl; $(C_{1-4})$alkoxy; halogen; and cyano;

or a salt of such a compound.

8. A compound according to claim 1, wherein the fragment

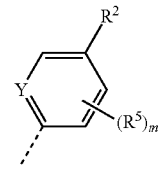

represents 4-fluorophenyl, 4-methylphenyl, 4-fluoro-3-cyano-phenyl, 3,4-difluorophenyl, 3,5-difluoro-4-methoxy-phenyl, 3-fluoro-4-methoxy-phenyl, 4-cyano-3-fluoro-phenyl, 4-cyano-3-methyl-phenyl, 3-cyano-4-methyl-phenyl, 4-methoxyphenyl, 4-ethoxyphenyl, 3,4-dimethoxyphenyl, 4-fluoro-3-methoxy-phenyl; 3,4-difluoro-5-methoxy-phenyl, 3-cyano-4-methoxy-phenyl, 4-cyano-3-methoxy-phenyl, 4-cyano-3-fluoro-5-methoxy-phenyl, 4-cyanophenyl, 4-(2-methoxy-ethoxy)-phenyl, 4-difluoromethoxy-phenyl, 4-trifluoromethoxy-phenyl, 3-fluoro-4-difluoromethoxy-phenyl; 3-fluoro-4-trifluoromethoxy-phenyl; or 5-cyano-pyridin-2-yl;

or a salt of such a compound.

9. A compound according to claim 1 selected from the group consisting of N-[2-(4-Fluoro-benzyl)-2H-[1,2,3]triazol-4-yl]-2-(4-isopropyl-phenyl)-acetamide;
2-(4-Dimethylamino-phenyl)-N-[2-(4-fluoro-benzyl)-2H-[1,2,3]triazol-4-yl]-acetamide; N-[2-(3,4-Difluoro-benzyl)-2H-[1,2,3]triazol-4-yl]-2-(4-isopropyl-phenyl)-acetamide;
N-[2-(3,4-Difluoro-benzyl)-2H-[1,2,3]triazol-4-yl]-2-(1-methyl-1H-indazol-5-yl)-acetamide;
N-[2-(3,4-Difluoro-benzyl)-2H-[1,2,3]triazol-4-yl]-2-(1-methyl-1H-indol-5-yl)-acetamide;
N-[2-(3,4-Difluoro-benzyl)-2H-[1,2,3]triazol-4-yl]-2-(1H-indol-6-yl)-acetamide;
2-(4-Cyclobutoxy-phenyl)-N-[2-(3,4-difluoro-benzyl)-2H-[1,2,3]triazol-4-yl]-acetamide;
2-(4-Cyclopropoxy-phenyl)-N-[2-(3,4-difluoro-benzyl)-2H-[1,2,3]triazol-4-yl]-acetamide;
2-[6-(Cyclopropyl(methyl)amino)-pyridin-3-yl]-N-[2-(3,4-difluoro-benzyl)-2H-[1,2,3]triazol-4-yl]-acetamide;
2-[6-(Cyclopropylmethyl-methyl-amino)-pyridin-3-yl]-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-[4-(1-methoxy-ethyl)-phenyl]-acetamide;
N-[2-(3,4-Difluoro-benzyl)-2H-[1,2,3]triazol-4-yl]-2-[4-(3-fluoro-oxetan-3-yl)-phenyl]-acetamide;
N-[2-(3,4-Difluoro-benzyl)-2H-[1,2,3]triazol-4-yl]-2-(1H-indol-5-yl)-acetamide;
2-(6-Diethylamino-pyridin-3-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-[6-(3,3-difluoro-pyrrolidin-1-yl)-pyridin-3-yl]-acetamide;
N-[2-(3,4-Difluoro-benzyl)-2H-[1,2,3]triazol-4-yl]-2-(6-pyrrolidin-1-yl-pyridin-3-yl)-acetamide;
N-[2-(3,4-Difluoro-benzyl)-2H-[1,2,3]triazol-4-yl]-2-(1,3,3-trimethyl-2-oxo-2,3-dihydro-1H-indol-5-yl)-acetamide;
N-[2-(3,4-Difluoro-benzyl)-2H-[1,2,3]triazol-4-yl]-2-[4-(3-methoxy-oxetan-3-yl)-phenyl]-acetamide;
N-[2-(3,4-Difluoro-benzyl)-2H-[1,2,3]triazol-4-yl]-2-(3,3-dimethyl-2-oxo-2,3-dihydro-1H-indol-5-yl)-acetamide;
N-[2-(3,4-Difluoro-benzyl)-2H-[1,2,3]triazol-4-yl]-2-[4-(3-methyl-oxetan-3-yl)-phenyl]-acetamide;

N-[2-(3,4-Difluoro-benzyl)-2H-[1,2,3]triazol-4-yl]-2-(4-oxetan-3-yl-phenyl)-acetamide; 2-(4-Isopropyl-phenyl)-N-[2-(4-methyl-benzyl)-2H-[1,2,3]triazol-4-yl]-acetamide;
2-(4-Isopropyl-phenyl)-N-[2-(4-methoxy-benzyl)-2H-[1,2,3]triazol-4-yl]-acetamide; N-[2-(4-Cyano-benzyl)-2H-[1,2,3]triazol-4-yl]-2-(4-isopropyl-phenyl)-acetamide;
N-[2-(3,4-Difluoro-benzyl)-2H-[1,2,3]triazol-4-yl]-2-(1-ethyl-1H-indazol-5-yl)-acetamide;
N-[2-(3,4-Difluoro-benzyl)-2H-[1,2,3]triazol-4-yl]-2-(1,3-dimethyl-1H-indazol-5-yl)-acetamide;
2-(3-Cyclopropyl-1H-indazol-5-yl)-N-[2-(3,4-difluoro-benzyl)-2H-[1,2,3]triazol-4-yl]-acetamide;
2-(1-Butyl-1H-indazol-5-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-(2-methyl-1H-indol-5-yl)-acetamide;
2-(3-Butyl-1H-indazol-5-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-(1-isopropyl-1H-indazol-5-yl)-acetamide;
N-[2-(3,4-Difluoro-benzyl)-2H-[1,2,3]triazol-4-yl]-2-(1-propyl-1H-indazol-5-yl)-acetamide;
2-(3-Cyclopropyl-1-methyl-1H-indazol-5-yl)-N-[2-(3,4-difluoro-benzyl)-2H-[1,2,3]triazol-4-yl]-acetamide;
N-[2-(3,4-Difluoro-benzyl)-2H-[1,2,3]triazol-4-yl]-2-(1-methyl-1H-pyrazolo[3,4-b]pyridin-5-yl)-acetamide;
N-[2-(3,4-Difluoro-benzyl)-2H-[1,2,3]triazol-4-yl]-2-(3-trifluoromethyl-1H-indazol-5-yl)-acetamide;
N-[2-(4-Ethoxy-benzyl)-2H-[1,2,3]triazol-4-yl]-2-(1-methyl-1H-indol-5-yl)-acetamide;
2-[6-(3,3-Difluoro-pyrrolidin-1-yl)-pyridin-3-yl]-N-[2-(4-ethoxy-benzyl)-2H-[1,2,3]triazol-4-yl]-acetamide;
N-[2-(4-Ethoxy-benzyl)-2H-[1,2,3]triazol-4-yl]-2-[4-(3-methyl-oxetan-3-yl)-phenyl]-acetamide;
2-(4-tert-Butyl-phenyl)-N-[2-(4-ethoxy-benzyl)-2H-[1,2,3]triazol-4-yl]-acetamide; N-[2-(4-Ethoxy-benzyl)-2H-[1,2,3]triazol-4-yl]-2-(4-isopropyl-phenyl)-acetamide;
N-[2-(4-Ethoxy-benzyl)-2H-[1,2,3]triazol-4-yl]-2-(6-pyrrolidin-1-yl-pyridin-3-yl)-acetamide;
N-[2-(4-Ethoxy-benzyl)-2H-[1,2,3]triazol-4-yl]-2-(1-methyl-1H-indazol-5-yl)-acetamide;
2-(6-Diethylamino-pyridin-3-yl)-N-[2-(3,4-dimethoxy-benzyl)-2H-[1,2,3]triazol-4-yl]-acetamide;
2-[6-(3,3-Difluoro-pyrrolidin-1-yl)-pyridin-3-yl]-N-[2-(3,4-dimethoxy-benzyl)-2H-[1,2,3]triazol-4-yl]-acetamide;
2-(4-tert-Butyl-phenyl)-N-[2-(3,4-dimethoxy-benzyl)-2H-[1,2,3]triazol-4-yl]-acetamide;
N-[2-(3,4-Dimethoxy-benzyl)-2H-[1,2,3]triazol-4-yl]-2-(4-isopropyl-phenyl)-acetamide; N-[2-(3,4-Dimethoxy-benzyl)-2H-[1,2,3]triazol-4-yl]-2-(6-pyrrolidin-1-yl-pyridin-3-yl)-acetamide;
N-[2-(4-Fluoro-benzyl)-2H-[1,2,3]triazol-4-yl]-2-(1-methyl-1H-indol-5-yl)-acetamide;
N-[2-(4-Fluoro-benzyl)-2H-[1,2,3]triazol-4-yl]-2-[4-(3-methyl-oxetan-3-yl)-phenyl]-acetamide;
2-(4-tert-Butyl-phenyl)-N-[2-(4-fluoro-benzyl)-2H-[1,2,3]triazol-4-yl]-acetamide;
N-[2-(4-Fluoro-benzyl)-2H-[1,2,3]triazol-4-yl]-2-(6-pyrrolidin-1-yl-pyridin-3-yl)-acetamide;
N-[2-(4-Fluoro-benzyl)-2H-[1,2,3]triazol-4-yl]-2-(1-methyl-1H-indazol-5-yl)-acetamide;
N-[2-(4-Methoxy-benzyl)-2H-[1,2,3]triazol-4-yl]-2-(1-methyl-1H-indol-5-yl)-acetamide;
2-(6-Diethylamino-pyridin-3-yl)-N-[2-(4-methoxy-benzyl)-2H-[1,2,3]triazol-4-yl]-acetamide; 2-[6-(3,3-Difluoro-pyrrolidin-1-yl)-pyridin-3-yl]-N-[2-(4-methoxy-benzyl)-2H-[1,2,3]triazol-4-yl]-acetamide;
N-[2-(4-Methoxy-benzyl)-2H-[1,2,3]triazol-4-yl]-2-[4-(3-methyl-oxetan-3-yl)-phenyl]-acetamide;
2-(4-tert-Butyl-phenyl)-N-[2-(4-methoxy-benzyl)-2H-[1,2,3]triazol-4-yl]-acetamide;
N-[2-(4-Methoxy-benzyl)-2H-[1,2,3]triazol-4-yl]-2-(6-pyrrolidin-1-yl-pyridin-3-yl)-acetamide;
N-[2-(4-Methoxy-benzyl)-2H-[1,2,3]triazol-4-yl]-2-(1-methyl-1H-indazol-5-yl)-acetamide;
N-[2-(4-Methyl-benzyl)-2H-[1,2,3]triazol-4-yl]-2-(1-methyl-1H-indol-5-yl)-acetamide;
2-[6-(3,3-Difluoro-pyrrolidin-1-yl)-pyridin-3-yl]-N-[2-(4-methyl-benzyl)-2H-[1,2,3]triazol-4-yl]-acetamide;
2-(4-tert-Butyl-phenyl)-N-[2-(4-methyl-benzyl)-2H-[1,2,3]triazol-4-yl]-acetamide;
N-[2-(4-Methyl-benzyl)-2H-[1,2,3]triazol-4-yl]-2-[4-(3-methyl-oxetan-3-yl)-phenyl]-acetamide;
N-[2-(4-Methyl-benzyl)-2H-[1,2,3]triazol-4-yl]-2-(6-pyrrolidin-1-yl-pyridin-3-yl)-acetamide;
N-[2-(4-Methyl-benzyl)-2H-[1,2,3]triazol-4-yl]-2-(1-methyl-1H-indazol-5-yl)-acetamide;
N-[2-(4-Cyano-3-fluoro-benzyl)-2H-[1,2,3]triazol-4-yl]-2-(1-methyl-1H-indol-5-yl)-acetamide;
N-[2-(4-Cyano-3-fluoro-benzyl)-2H-[1,2,3]triazol-4-yl]-2-[6-(3,3-difluoro-pyrrolidin-1-yl)-pyridin-3-yl]-acetamide;
N-[2-(4-Cyano-3-fluoro-benzyl)-2H-[1,2,3]triazol-4-yl]-2-[4-(3-methyl-oxetan-3-yl)-phenyl]-acetamide;
2-(4-tert-Butyl-phenyl)-N-[2-(4-cyano-3-fluoro-benzyl)-2H-[1,2,3]triazol-4-yl]-acetamide;
N-[2-(4-Cyano-3-fluoro-benzyl)-2H-[1,2,3]triazol-4-yl]-2-(4-isopropyl-phenyl)-acetamide; N-[2-(4-Cyano-3-fluoro-benzyl)-2H-[1,2,3]triazol-4-yl]-2-(6-pyrrolidin-1-yl-pyridin-3-yl)-acetamide;
N-[2-(4-Cyano-3-fluoro-benzyl)-2H-[1,2,3]triazol-4-yl]-2-(1-methyl-1H-indazol-5-yl)-acetamide;
N-[2-(3,5-Difluoro-4-methoxy-benzyl)-2H-[1,2,3]triazol-4-yl]-2-(1-methyl-1H-indol-5-yl)-acetamide;
N-[2-(3,5-Difluoro-4-methoxy-benzyl)-2H-[1,2,3]triazol-4-yl]-2-[4-(3-methyl-oxetan-3-yl)-phenyl]-acetamide;
2-(4-tert-Butyl-phenyl)-N-[2-(3,5-difluoro-4-methoxy-benzyl)-2H-[1,2,3]triazol-4-yl]-acetamide;
N-[2-(3,5-Difluoro-4-methoxy-benzyl)-2H-[1,2,3]triazol-4-yl]-2-(4-isopropyl-phenyl)-acetamide;
N-[2-(3,5-Difluoro-4-methoxy-benzyl)-2H-[1,2,3]triazol-4-yl]-2-(6-pyrrolidin-1-yl-pyridin-3-yl)-acetamide;
N-[2-(3,5-Difluoro-4-methoxy-benzyl)-2H-[1,2,3]triazol-4-yl]-2-(1-methyl-1H-indazol-5-yl)-acetamide;
2-(4-tert-Butyl-phenyl)-N-{2-[4-(2-methoxy-ethoxy)-benzyl]-2H-[1,2,3]triazol-4-yl}-acetamide;
N-{2-[4-(2-Methoxy-ethoxy)-benzyl]-2H-[1,2,3]triazol-4-yl}-2-(1-methyl-1H-indol-5-yl)-acetamide;
2-(4-tert-Butyl-phenyl)-N-[2-(4-difluoromethoxy-benzyl)-2H-[1,2,3]triazol-4-yl]-acetamide; N-[2-(4-Difluoromethoxy-benzyl)-2H-[1,2,3]triazol-4-yl]-2-(1-methyl-1H-indol-5-yl)-acetamide;
2-(4-tert-Butyl-phenyl)-N-[2-(4-trifluoromethoxy-benzyl)-2H-[1,2,3]triazol-4-yl]-acetamide; 2-(1-Methyl-1H-indol-5-yl)-N-[2-(4-trifluoromethoxy-benzyl)-2H-[1,2,3]triazol-4-yl]-acetamide;
2-(1-Methyl-1H-indazol-5-yl)-N-[2-(4-trifluoromethoxy-benzyl)-2H-[1,2,3]triazol-4-yl]-acetamide;

2-[4-(3-Methyl-oxetan-3-yl)-phenyl]-N-[2-(4-trifluoromethoxy-benzyl)-2H-[1,2,3]triazol-4-yl]-acetamide;
2-[6-(3,3-Difluoro-pyrrolidin-1-yl)-pyridin-3-yl]-N-[2-(4-fluoro-benzyl)-2H-[1,2,3]triazol-4-yl]-acetamide;
2-(6-Diethylamino-pyridin-3-yl)-N-[2-(4-fluoro-benzyl)-2H-[1,2,3]triazol-4-yl]-acetamide; 2-(4-tert-Butyl-phenyl)-N-[2-(4-cyano-benzyl)-2H-[1,2,3]triazol-4-yl]-acetamide;
N-[2-(4-Cyano-benzyl)-2H-[1,2,3]triazol-4-yl]-2-[6-(3,3-difluoro-pyrrolidin-1-yl)-pyridin-3-yl]-acetamide;
N-[2-(4-Cyano-benzyl)-2H-[1,2,3]triazol-4-yl]-2-(6-pyrrolidin-1-yl-pyridin-3-yl)-acetamide;
N-[2-(4-Cyano-benzyl)-2H-[1,2,3]triazol-4-yl]-2-(1-methyl-1H-indol-5-yl)-acetamide;
N-[2-(4-Cyano-benzyl)-2H-[1,2,3]triazol-4-yl]-2-(1,3-dimethyl-1H-indol-5-yl)-acetamide;
N-[2-(4-Cyano-benzyl)-2H-[1,2,3]triazol-4-yl]-2-(1-methyl-1H-indazol-6-yl)-acetamide;
N-[2-(4-Cyano-benzyl)-2H-[1,2,3]triazol-4-yl]-2-(1,3-dimethyl-1H-indazol-5-yl)-acetamide;
N-[2-(4-Cyano-benzyl)-2H-[1,2,3]triazol-4-yl]-2-(1-ethyl-1H-indazol-5-yl)-acetamide;
N-[2-(4-Cyano-benzyl)-2H-[1,2,3]triazol-4-yl]-2-(1-propyl-1H-indazol-5-yl)-acetamide;
N-[2-(4-Cyano-3-fluoro-benzyl)-2H-[1,2,3]triazol-4-yl]-2-(1,3-dimethyl-1H-indol-6-yl)-acetamide;
N-[2-(4-Cyano-benzyl)-2H-[1,2,3]triazol-4-yl]-2-(1,3-dimethyl-1H-indol-6-yl)-acetamide;
N-[2-(4-Fluoro-3-methoxy-benzyl)-2H-[1,2,3]triazol-4-yl]-2-[4-(oxetan-3-ylmethoxy)-phenyl]-acetamide;
N-[2-(4-Fluoro-3-methoxy-benzyl)-2H-[1,2,3]triazol-4-yl]-2-(1-methyl-1H-indazol-6-yl)-acetamide;
N-[2-(4-Fluoro-3-methoxy-benzyl)-2H-[1,2,3]triazol-4-yl]-2-[4-(3-methoxy-oxetan-3-yl)-phenyl]-acetamide;
2-[4-(3,3-Difluoro-cyclobutylmethoxy)-phenyl]-N-[2-(4-fluoro-3-methoxy-benzyl)-2H-[1,2,3]triazol-4-yl]-acetamide;
N-[2-(4-Fluoro-3-methoxy-benzyl)-2H-[1,2,3]triazol-4-yl]-2-[4-(3-methyl-oxetan-3-ylmethoxy)-phenyl]-acetamide;
N-[2-(4-Fluoro-3-methoxy-benzyl)-2H-[1,2,3]triazol-4-yl]-2-[4-(1-trifluoromethyl-cyclopropyl)-phenyl]-acetamide;
2-[4-(3,3-Difluoro-cyclobutoxy)-phenyl]-N-[2-(4-fluoro-3-methoxy-benzyl)-2H-[1,2,3]triazol-4-yl]-acetamide;
2-[6-(3,3-Difluoro-pyrrolidin-1-yl)-pyridin-3-yl]-N-[2-(4-fluoro-3-methoxy-benzyl)-2H-[1,2,3]triazol-4-yl]-acetamide;
N-[2-(4-Fluoro-3-methoxy-benzyl)-2H-[1,2,3]triazol-4-yl]-2-[4-(3-fluoro-oxetan-3-yl)-phenyl]-acetamide;
2-(1-Ethyl-1H-indazol-5-yl)-N-[2-(4-fluoro-3-methoxy-benzyl)-2H-[1,2,3]triazol-4-yl]-acetamide;
2-(1,3-Dimethyl-1H-indol-5-yl)-N-[2-(4-fluoro-3-methoxy-benzyl)-2H-[1,2,3]triazol-4-yl]-acetamide;
2-(4-tert-Butyl-phenyl)-N-[2-(4-fluoro-3-methoxy-benzyl)-2H-[1,2,3]triazol-4-yl]-acetamide;
N-[2-(3-Fluoro-4-methoxy-benzyl)-2H-[1,2,3]triazol-4-yl]-2-[4-(oxetan-3-ylmethoxy)-phenyl]-acetamide;
N-[2-(3-Fluoro-4-methoxy-benzyl)-2H-[1,2,3]triazol-4-yl]-2-(1-methyl-1H-indazol-6-yl)-acetamide;
N-[2-(3-Fluoro-4-methoxy-benzyl)-2H-[1,2,3]triazol-4-yl]-2-[4-(3-methoxy-oxetan-3-yl)-phenyl]-acetamide;
N-[2-(3-Fluoro-4-methoxy-benzyl)-2H-[1,2,3]triazol-4-yl]-2-[4-(3-methyl-oxetan-3-ylmethoxy)-phenyl]-acetamide;
N-[2-(3-Fluoro-4-methoxy-benzyl)-2H-[1,2,3]triazol-4-yl]-2-[4-(1-trifluoromethyl-cyclopropyl)-phenyl]-acetamide;
2-[4-(3,3-Difluoro-cyclobutoxy)-phenyl]-N-[2-(3-fluoro-4-methoxy-benzyl)-2H-[1,2,3]triazol-4-yl]-acetamide;
2-[6-(3,3-Difluoro-pyrrolidin-1-yl)-pyridin-3-yl]-N-[2-(3-fluoro-4-methoxy-benzyl)-2H-[1,2,3]triazol-4-yl]-acetamide;
N-[2-(3-Fluoro-4-methoxy-benzyl)-2H-[1,2,3]triazol-4-yl]-2-[4-(3-fluoro-oxetan-3-yl)-phenyl]-acetamide;
2-(1-Ethyl-H-indazol-5-yl)-N-[2-(3-fluoro-4-methoxy-benzyl)-2H-[1,2,3]triazol-4-yl]-acetamide;
2-(1,3-Dimethyl-1H-indol-5-yl)-N-[2-(3-fluoro-4-methoxy-benzyl)-2H-[1,2,3]triazol-4-yl]-acetamide;
2-(4-tert-Butyl-phenyl)-N-[2-(3-fluoro-4-methoxy-benzyl)-2H-[1,2,3]triazol-4-yl]-acetamide; N-[2-(4-Cyano-3-fluoro-benzyl)-2H-[1,2,3]triazol-4-yl]-2-[4-(oxetan-3-ylmethoxy)-phenyl]-acetamide;
N-[2-(4-Cyano-3-fluoro-benzyl)-2H-[1,2,3]triazol-4-yl]-2-(1-methyl-1H-indazol-6-yl)-acetamide;
N-[2-(4-Cyano-3-fluoro-benzyl)-2H-[1,2,3]triazol-4-yl]-2-[4-(3-methoxy-oxetan-3-yl)-phenyl]-acetamide;
N-[2-(4-Cyano-3-fluoro-benzyl)-2H-[1,2,3]triazol-4-yl]-2-[4-(3,3-difluoro-cyclobutylmethoxy)-phenyl]-acetamide;
N-[2-(4-Cyano-3-fluoro-benzyl)-2H-[1,2,3]triazol-4-yl]-2-[4-(3-methyl-oxetan-3-ylmethoxy)-phenyl]-acetamide;
N-[2-(4-Cyano-3-fluoro-benzyl)-2H-[1,2,3]triazol-4-yl]-2-[4-(1-trifluoromethyl-cyclopropyl)-phenyl]-acetamide;
N-[2-(4-Cyano-3-fluoro-benzyl)-2H-[1,2,3]triazol-4-yl]-2-[4-(3,3-difluoro-cyclobutoxy)-phenyl]-acetamide;
N-[2-(4-Cyano-3-fluoro-benzyl)-2H-[1,2,3]triazol-4-yl]-2-[4-(3-fluoro-oxetan-3-yl)-phenyl]-acetamide;
N-[2-(4-Cyano-3-fluoro-benzyl)-2H-[1,2,3]triazol-4-yl]-2-(1-ethyl-1H-indazol-5-yl)-acetamide
N-[2-(4-Cyano-3-fluoro-benzyl)-2H-[1,2,3]triazol-4-yl]-2-(1,3-dimethyl-1H-indol-5-yl)-acetamide;
N-[2-(3,5-Difluoro-4-methoxy-benzyl)-2H-[1,2,3]triazol-4-yl]-2-[4-(oxetan-3-ylmethoxy)-phenyl]-acetamide;
N-[2-(3,5-Difluoro-4-methoxy-benzyl)-2H-[1,2,3]triazol-4-yl]-2-(1-methyl-1H-indazol-6-yl)-acetamide;
N-[2-(3,5-Difluoro-4-methoxy-benzyl)-2H-[1,2,3]triazol-4-yl]-2-[4-(3-methoxy-oxetan-3-yl)-phenyl]-acetamide;
N-[2-(3,5-Difluoro-4-methoxy-benzyl)-2H-[1,2,3]triazol-4-yl]-2-[4-(3-methyl-oxetan-3-ylmethoxy)-phenyl]-acetamide;
N-[2-(3,5-Difluoro-4-methoxy-benzyl)-2H-[1,2,3]triazol-4-yl]-2-[4-(1-trifluoromethyl-cyclopropyl)-phenyl]-acetamide;
2-[4-(3,3-Difluoro-cyclobutoxy)-phenyl]-N-[2-(3,5-difluoro-4-methoxy-benzyl)-2H-[1,2,3]triazol-4-yl]-acetamide;
N-[2-(3,5-Difluoro-4-methoxy-benzyl)-2H-[1,2,3]triazol-4-yl]-2-[6-(3,3-difluoro-pyrrolidin-1-yl)-pyridin-3-yl]-acetamide;
N-[2-(3,5-Difluoro-4-methoxy-benzyl)-2H-[1,2,3]triazol-4-yl]-2-[4-(3-fluoro-oxetan-3-yl)-phenyl]-acetamide;
N-[2-(3,5-Difluoro-4-methoxy-benzyl)-2H-[1,2,3]triazol-4-yl]-2-(1-ethyl-1H-indazol-5-yl)-acetamide;
N-[2-(3,5-Difluoro-4-methoxy-benzyl)-2H-[1,2,3]triazol-4-yl]-2-(1,3-dimethyl-1H-indol-5-yl)-acetamide;

N-[2-(4-Fluoro-3-methoxy-benzyl)-2H-[1,2,3]triazol-4-yl]-2-(1-methyl-1H-indazol-5-yl)-acetamide;
N-[2-(3-Fluoro-4-methoxy-benzyl)-2H-[1,2,3]triazol-4-yl]-2-(1-methyl-1H-indazol-5-yl)-acetamide;
N-[2-(4-Fluoro-3-methoxy-benzyl)-2H-[1,2,3]triazol-4-yl]-2-(4-isopropyl-phenyl)-acetamide; N-[2-(3-Fluoro-4-methoxy-benzyl)-2H-[1,2,3]triazol-4-yl]-2-(4-isopropyl-phenyl)-acetamide; N-[2-(4-Fluoro-3-methoxy-benzyl)-2H-[1,2,3]triazol-4-yl]-2-(6-pyrrolidin-1-yl-pyridin-3-yl)-acetamide;
N-[2-(3-Fluoro-4-methoxy-benzyl)-2H-[1,2,3]triazol-4-yl]-2-(6-pyrrolidin-1-yl-pyridin-3-yl)-acetamide;
2-[4-(Cyano-dimethyl-methyl)-phenyl]-N-[2-(4-cyano-3-fluoro-benzyl)-2H-[1,2,3]triazol-4-yl]-acetamide;
2-(4-tert-Butyl-phenyl)-N-[2-(4-cyano-3-fluoro-5-methoxy-benzyl)-2H-[1,2,3]triazol-4-yl]-acetamide;
N-[2-(4-Cyano-3-fluoro-benzyl)-2H-[1,2,3]triazol-4-yl]-2-(4-trifluoromethyl-phenyl)-acetamide; N-[2-(4-Cyano-3-fluoro-benzyl)-2H-[1,2,3]triazol-4-yl]-2-(5-fluoro-6-pyrrolidin-1-yl-pyridin-3-yl)-acetamide;
2-(4-tert-Butyl-phenyl)-N-[2-(4-cyano-3-methyl-benzyl)-2H-[1,2,3]triazol-4-yl]-acetamide;
N-[2-(4-Cyano-3-methyl-benzyl)-2H-[1,2,3]triazol-4-yl]-2-(1-methyl-1H-indazol-6-yl)-acetamide;
N-[2-(4-Cyano-3-methyl-benzyl)-2H-[1,2,3]triazol-4-yl]-2-(1-methyl-1H-indazol-5-yl)-acetamide;
N-[2-(4-Cyano-3-methyl-benzyl)-2H-[1,2,3]triazol-4-yl]-2-(4-isopropyl-phenyl)-acetamide; N-[2-(4-Cyano-3-methyl-benzyl)-2H-[1,2,3]triazol-4-yl]-2-[4-(3,3-difluoro-cyclobutoxy)-phenyl]-acetamide;
N-[2-(4-Cyano-3-methyl-benzyl)-2H-[1,2,3]triazol-4-yl]-2-[6-(3,3-difluoro-pyrrolidin-1-yl)-pyridin-3-yl]-acetamide;
N-[2-(4-Cyano-3-methyl-benzyl)-2H-[1,2,3]triazol-4-yl]-2-(1-ethyl-1H-indazol-5-yl)-acetamide;
N-[2-(4-Cyano-3-methyl-benzyl)-2H-[1,2,3]triazol-4-yl]-2-(1,3-dimethyl-1H-indazol-5-yl)-acetamide;
N-[2-(4-Cyano-3-methyl-benzyl)-2H-[1,2,3]triazol-4-yl]-2-(6-pyrrolidin-1-yl-pyridin-3-yl)-acetamide;
N-[2-(4-Cyano-3-methyl-benzyl)-2H-[1,2,3]triazol-4-yl]-2-(1,3-dimethyl-1H-indol-5-yl)-acetamide;
2-(4-tert-Butyl-phenyl)-N-[2-(3-cyano-4-fluoro-benzyl)-2H-[1,2,3]triazol-4-yl]-acetamide;
N-[2-(3-Cyano-4-fluoro-benzyl)-2H-[1,2,3]triazol-4-yl]-2-(1-methyl-1H-indazol-5-yl)-acetamide;
N-[2-(3-Cyano-4-fluoro-benzyl)-2H-[1,2,3]triazol-4-yl]-2-(4-isopropyl-phenyl)-acetamide;
N-[2-(4-Cyano-3-fluoro-benzyl)-2H-[1,2,3]triazol-4-yl]-2-[4-(3-fluoro-oxetan-3-ylmethoxy)-phenyl]-acetamide;
N-[2-(4-Cyano-3-fluoro-benzyl)-2H-[1,2,3]triazol-4-yl]-2-[4-(3,3-difluoro-1-methyl-cyclobutylmethoxy)-phenyl]-acetamide;
N-[2-(4-Cyano-3-fluoro-benzyl)-2H-[1,2,3]triazol-4-yl]-2-(1,3-dimethyl-1H-indazol-5-yl)-acetamide;
2-(4-tert-Butyl-phenyl)-N-[2-(4-difluoromethoxy-3-fluoro-benzyl)-2H-[1,2,3]triazol-4-yl]-acetamide;
N-[2-(4-Difluoromethoxy-3-fluoro-benzyl)-2H-[1,2,3]triazol-4-yl]-2-(1-methyl-1H-indazol-5-yl)-acetamide;
N-[2-(4-Difluoromethoxy-3-fluoro-benzyl)-2H-[1,2,3]triazol-4-yl]-2-(4-isopropyl-phenyl)-acetamide;
N-[2-(4-Difluoromethoxy-3-fluoro-benzyl)-2H-[1,2,3]triazol-4-yl]-2-[4-(1-trifluoromethyl-cyclopropyl)-phenyl]-acetamide;
N-[2-(4-Difluoromethoxy-3-fluoro-benzyl)-2H-[1,2,3]triazol-4-yl]-2-[6-(3,3-difluoro-pyrrolidin-1-yl)-pyridin-3-yl]-acetamide;
N-[2-(4-Difluoromethoxy-3-fluoro-benzyl)-2H-[1,2,3]triazol-4-yl]-2-(6-pyrrolidin-1-yl-pyridin-3-yl)-acetamide;
2-(4-tert-Butyl-phenyl)-N-[2-(3-fluoro-4-trifluoromethoxy-benzyl)-2H-[1,2,3]triazol-4-yl]-acetamide;
N-[2-(3-Fluoro-4-trifluoromethoxy-benzyl)-2H-[1,2,3]triazol-4-yl]-2-(1-methyl-1H-indazol-6-yl)-acetamide;
N-[2-(3-Fluoro-4-trifluoromethoxy-benzyl)-2H-[1,2,3]triazol-4-yl]-2-(1-methyl-1H-indazol-5-yl)-acetamide;
N-[2-(3-Fluoro-4-trifluoromethoxy-benzyl)-2H-[1,2,3]triazol-4-yl]-2-(4-isopropyl-phenyl)-acetamide;
N-[2-(3-Fluoro-4-trifluoromethoxy-benzyl)-2H-[1,2,3]triazol-4-yl]-2-[4-(1-trifluoromethyl-cyclopropyl)-phenyl]-acetamide;
2-[6-(3,3-Difluoro-pyrrolidin-1-yl)-pyridin-3-yl]-N-[2-(3-fluoro-4-trifluoromethoxy-benzyl)-2H-[1,2,3]triazol-4-yl]-acetamide;
2-(1-Ethyl-1H-indazol-5-yl)-N-[2-(3-fluoro-4-trifluoromethoxy-benzyl)-2H-[1,2,3]triazol-4-yl]-acetamide;
2-(1,3-Dimethyl-1H-indazol-5-yl)-N-[2-(3-fluoro-4-trifluoromethoxy-benzyl)-2H-[1,2,3]triazol-4-yl]-acetamide;
N-[2-(3-Fluoro-4-trifluoromethoxy-benzyl)-2H-[1,2,3]triazol-4-yl]-2-(6-pyrrolidin-1-yl-pyridin-3-yl)-acetamide;
N-[2-(4-Cyano-benzyl)-2H-[1,2,3]triazol-4-yl]-2-[4-(3-methyl-oxetan-3-ylmethoxy)-phenyl]-acetamide;
N-[2-(4-Cyano-benzyl)-2H-[1,2,3]triazol-4-yl]-2-[4-(3-fluoro-oxetan-3-ylmethoxy)-phenyl]-acetamide;
N-[2-(4-Cyano-benzyl)-2H-[1,2,3]triazol-4-yl]-2-[4-(1-trifluoromethyl-cyclopropyl)-phenyl]-acetamide;
N-[2-(4-Cyano-benzyl)-2H-[1,2,3]triazol-4-yl]-2-[4-(3,3-difluoro-cyclobutoxy)-phenyl]-acetamide;
N-[2-(4-Cyano-benzyl)-2H-[1,2,3]triazol-4-yl]-2-[4-(3,3-difluoro-1-methyl-cyclobutylmethoxy)-phenyl]-acetamide;
N-[2-(4-Cyano-benzyl)-2H-[1,2,3]triazol-4-yl]-2-[4-(3-fluoro-oxetan-3-yl)-phenyl]-acetamide;
N-[2-(4-Cyano-3-fluoro-benzyl)-2H-[1,2,3]triazol-4-yl]-2-[3-methyl-4-(2,2,2-trifluoro-ethoxy)-phenyl]-acetamide;
N-[2-(3-Cyano-4-methyl-benzyl)-2H-[1,2,3]triazol-4-yl]-2-[4-(3-fluoro-oxetan-3-ylmethoxy)-phenyl]-acetamide;
N-[2-(3-Cyano-4-methyl-benzyl)-2H-[1,2,3]triazol-4-yl]-2-[4-(3-fluoro-oxetan-3-yl)-phenyl]-acetamide;
2-(4-tert-Butyl-phenyl)-N-[2-(3-cyano-4-methoxy-benzyl)-2H-[1,2,3]triazol-4-yl]-acetamide;
N-[2-(3-Cyano-4-methoxy-benzyl)-2H-[1,2,3]triazol-4-yl]-2-[4-(1-trifluoromethyl-cyclopropyl)-phenyl]-acetamide;
N-[2-(3-Cyano-4-methyl-benzyl)-2H-[1,2,3]triazol-4-yl]-2-(1-methyl-1H-indazol-5-yl)-acetamide;
N-[2-(3-Cyano-4-methoxy-benzyl)-2H-[1,2,3]triazol-4-yl]-2-(4-isopropyl-phenyl)-acetamide;
N-[2-(3-Cyano-4-methyl-benzyl)-2H-[1,2,3]triazol-4-yl]-2-[4-(3-methoxy-oxetan-3-yl)-phenyl]-acetamide;
N-[2-(3-Cyano-4-methoxy-benzyl)-2H-[1,2,3]triazol-4-yl]-2-[6-(3,3-difluoro-pyrrolidin-1-yl)-pyridin-3-yl]-acetamide;
N-[2-(3-Cyano-4-methoxy-benzyl)-2H-[1,2,3]triazol-4-yl]-2-(1-methyl-1H-indazol-5-yl)-acetamide;
N-[2-(3-Cyano-4-methyl-benzyl)-2H-[1,2,3]triazol-4-yl]-2-[4-(3,3-difluoro-cyclobutoxy)-phenyl]-acetamide;
N-[2-(3,4-Difluoro-5-methoxy-benzyl)-2H-[1,2,3]triazol-4-yl]-2-(1,3-dimethyl-1H-indazol-5-yl)-acetamide;

N-[2-(3-Cyano-4-methyl-benzyl)-2H-[1,2,3]triazol-4-yl]-2-[6-(3,3-difluoro-pyrrolidin-1-yl)-pyridin-3-yl]-acetamide;

N-[2-(3,4-Difluoro-5-methoxy-benzyl)-2H-[1,2,3]triazol-4-yl]-2-(1-methyl-1H-indazol-5-yl)-acetamide;

N-[2-(3-Cyano-4-methyl-benzyl)-2H-[1,2,3]triazol-4-yl]-2-(6-pyrrolidin-1-yl-pyridin-3-yl)-acetamide;

N-[2-(3-Cyano-4-methoxy-benzyl)-2H-[1,2,3]triazol-4-yl]-2-[4-(3-fluoro-oxetan-3-yl)-phenyl]-acetamide;

N-[2-(3-Cyano-4-methyl-benzyl)-2H-[1,2,3]triazol-4-yl]-2-(1-methyl-1H-indazol-6-yl)-acetamide;

N-[2-(3-Cyano-4-methyl-benzyl)-2H-[1,2,3]triazol-4-yl]-2-(4-isopropyl-phenyl)-acetamide; 2-(4-tert-Butyl-phenyl)-N-[2-(3-cyano-4-methyl-benzyl)-2H-[1,2,3]triazol-4-yl]-acetamide;

2-(4-tert-Butyl-phenyl)-N-[2-(3,4-difluoro-5-methoxy-benzyl)-2H-[1,2,3]triazol-4-yl]-acetamide;

N-[2-(3,4-Difluoro-5-methoxy-benzyl)-2H-[1,2,3]triazol-4-yl]-2-[6-(3,3-difluoro-pyrrolidin-1-yl)-pyridin-3-yl]-acetamide;

N-[2-(3,4-Difluoro-5-methoxy-benzyl)-2H-[1,2,3]triazol-4-yl]-2-(1-ethyl-1H-indazol-5-yl)-acetamide;

N-[2-(3,4-Difluoro-5-methoxy-benzyl)-2H-[1,2,3]triazol-4-yl]-2-(6-pyrrolidin-1-yl-pyridin-3-yl)-acetamide;

N-[2-(3,4-Difluoro-5-methoxy-benzyl)-2H-[1,2,3]triazol-4-yl]-2-(4-isopropyl-phenyl)-acetamide;

N-[2-(3-Cyano-4-methoxy-benzyl)-2H-[1,2,3]triazol-4-yl]-2-[4-(3,3-difluoro-cyclobutoxy)-phenyl]-acetamide;

N-[2-(3,4-Difluoro-5-methoxy-benzyl)-2H-[1,2,3]triazol-4-yl]-2-[4-(3-fluoro-oxetan-3-yl)-phenyl]-acetamide;

N-[2-(3,4-Difluoro-5-methoxy-benzyl)-2H-[1,2,3]triazol-4-yl]-2-(1-methyl-1H-indazol-6-yl)-acetamide;

N-[2-(3-Cyano-4-methyl-benzyl)-2H-[1,2,3]triazol-4-yl]-2-[4-(1-trifluoromethyl-cyclopropyl)-phenyl]-acetamide;

N-[2-(3,4-Difluoro-5-methoxy-benzyl)-2H-[1,2,3]triazol-4-yl]-2-[4-(1-trifluoromethyl-cyclopropyl)-phenyl]-acetamide;

N-[2-(3,4-Difluoro-5-methoxy-benzyl)-2H-[1,2,3]triazol-4-yl]-2-[4-(3-methoxy-oxetan-3-yl)-phenyl]-acetamide;

N-[2-(3,4-Difluoro-5-methoxy-benzyl)-2H-[1,2,3]triazol-4-yl]-2-[4-(3-fluoro-oxetan-3-ylmethoxy)-phenyl]-acetamide;

2-[4-(3,3-Difluoro-cyclobutoxy)-phenyl]-N-[2-(3,4-difluoro-5-methoxy-benzyl)-2H-[1,2,3]triazol-4-yl]-acetamide;

2-[4-(1-Cyano-cyclopropyl)-phenyl]-N-[2-(4-cyano-3-fluoro-benzyl)-2H-[1,2,3]triazol-4-yl]-acetamide;

N-(2-(4-cyano-3-fluorobenzyl)-2H-1,2,3-triazol-4-yl)-2-(4-(pentafluorosulfanyl)phenyl)acetamide;

N-[2-(4-Cyano-3-methoxy-benzyl)-2H-[1,2,3]triazol-4-yl]-2-[4-(1-trifluoromethyl-cyclopropyl)-phenyl]-acetamide;

N-[2-(4-Cyano-benzyl)-2H-[1,2,3]triazol-4-yl]-2-(1-methyl-1H-indazol-5-yl)-acetamide;

N-[2-(4-Cyano-3-methyl-benzyl)-2H-[1,2,3]triazol-4-yl]-2-[4-(3-fluoro-oxetan-3-yl)-phenyl]-acetamide;

N-[2-(3-Cyano-4-methoxy-benzyl)-2H-[1,2,3]triazol-4-yl]-2-(6-pyrrolidin-1-yl-pyridin-3-yl)-acetamide;

N-[2-(4-Cyano-benzyl)-2H-[1,2,3]triazol-4-yl]-2-[4-(3-methoxy-oxetan-3-yl)-phenyl]-acetamide;

N-[2-(4-Cyano-benzyl)-2H-[1,2,3]triazol-4-yl]-2-[4-(3,3-difluoro-cyclobutylmethoxy)-phenyl]-acetamide;

2-(4-tert-Butyl-phenyl)-N-[2-(4-cyano-3-methoxy-benzyl)-2H-[1,2,3]triazol-4-yl]-acetamide;

N-[2-(3,4-Difluoro-5-methoxy-benzyl)-2H-[1,2,3]triazol-4-yl]-2-(1,3-dimethyl-1H-indol-5-yl)-acetamide;

N-[2-(4-Cyano-3-methyl-benzyl)-2H-[1,2,3]triazol-4-yl]-2-[4-(1-trifluoromethyl-cyclopropyl)-phenyl]-acetamide;

N-[2-(5-Cyano-pyridin-2-ylmethyl)-2H-[1,2,3]triazol-4-yl]-2-[3-methyl-4-(2,2,2-trifluoro-ethoxy)-phenyl]-acetamide;

N-[2-(5-Cyano-pyridin-2-ylmethyl)-2H-[1,2,3]triazol-4-yl]-2-(1,3-dimethyl-1H-indol-5-yl)-acetamide;

2-(4-tert-Butyl-phenyl)-N-[2-(5-cyano-pyridin-2-ylmethyl)-2H-[1,2,3]triazol-4-yl]-acetamide; N-[2-(5-Cyano-pyridin-2-ylmethyl)-2H-[1,2,3]triazol-4-yl]-2-[4-(1-trifluoromethyl-cyclopropyl)-phenyl]-acetamide;

N-[2-(5-Cyano-pyridin-2-ylmethyl)-2H-[1,2,3]triazol-4-yl]-2-[4-(3,3-difluoro-cyclobutoxy)-phenyl]-acetamide;

N-[2-(5-Cyano-pyridin-2-ylmethyl)-2H-[1,2,3]triazol-4-yl]-2-(5-fluoro-6-pyrrolidin-1-yl-pyridin-3-yl)-acetamide;

N-[2-(4-Cyano-3-fluoro-benzyl)-2H-[1,2,3]triazol-4-yl]-2-[4-(2,2,2-trifluoro-1,1-dimethyl-ethyl)-phenyl]-acetamide; and N-[2-(4-Cyano-3-fluoro-benzyl)-2H-[1,2,3]triazol-4-yl]-2-[4-((1S*,2S*)-2-trifluoromethyl-cyclopropyl)-phenyl]-acetamide;

or a salt of such a compound.

10. A pharmaceutical composition containing, as active principle, a compound of formula (I) according to claim 1, or a pharmaceutically acceptable salt thereof, and at least one therapeutically inert excipient.

11. A compound of formula (I) according to claim 1, or a pharmaceutically acceptable salt thereof, for use as a medicament.

12. A compound of formula (I) according to claim 1, or a pharmaceutically acceptable salt thereof, for use in the treatment of epilepsy; sleep disorders; sleep disturbances; pain; neurological disorders; cardiovascular disorders; cancer; diabetes; diabetic neuropathy; infertility; and sexual dysfunction.

13. A method of treating a disease comprising administering a pharmaceutically active amount of the compound of formula (I) according to claim 1, or a pharmaceutically acceptable salt thereof, to a subject in need thereof, wherein the disease is selected from epilepsy; sleep disorders; sleep disturbances; pain; neurological disorders; cardiovascular disorders; cancer; diabetes; diabetic neuropathy; infertility; and sexual dysfunction.

* * * * *